(12) United States Patent
Bohme et al.

(10) Patent No.: US 8,771,952 B2
(45) Date of Patent: Jul. 8, 2014

(54) SUBSTANCES AND METHODS FOR A DNA BASED PROFILING ASSAY

(75) Inventors: Manja Bohme, Muglitzal/OT Maxen (DE); Jorg Gabert, Leipzig (DE); Werner Brabetz, Dresden (DE)

(73) Assignee: Qiagen GmbH, Hilden (DE)

( * ) Notice: Subject to any disclaimer, the term of this patent is extended or adjusted under 35 U.S.C. 154(b) by 494 days.

(21) Appl. No.: 12/990,155

(22) PCT Filed: Apr. 24, 2009

(86) PCT No.: PCT/EP2009/003351
§ 371 (c)(1),
(2), (4) Date: Jan. 6, 2011

(87) PCT Pub. No.: WO2009/132860
PCT Pub. Date: Nov. 5, 2009

(65) Prior Publication Data
US 2011/0143347 A1 Jun. 16, 2011

(30) Foreign Application Priority Data

Apr. 28, 2008 (EP) .................................... 08155280

(51) Int. Cl.
*C12Q 1/68* (2006.01)
*C12P 19/34* (2006.01)

(52) U.S. Cl.
USPC ........................... 435/6.12; 435/6.1; 435/6.11

(58) Field of Classification Search
None
See application file for complete search history.

(56) References Cited

U.S. PATENT DOCUMENTS 6,458,537 B1   10/2002   Staub et al.

FOREIGN PATENT DOCUMENTS

| EP | 1319718 A1 * | 6/2003 |
| EP | 1 914 481 | 4/2008 |
| WO | WO 2004/081186 | 9/2004 |

OTHER PUBLICATIONS

Hanson et al., "Comprehensive annotated STR physical map of the human Y chromosome: Forensic implications," Legal Medicine, 2006, vol. 8, pp. 110-120.*
Friis et al., "Typing of 30 insertion/deletions in Danes using the first commercial indel kit-Mentype DIPplex," Forensic Science International, 2012, vol. 6, pp. e72-e74.*
Hayashi et al., "Development of PCR-based allele-specific and InDel marker sets for nine rice blast resistance genes," Theoretical and Applied Genetics, 2006, vol. 113, issue 113, pp. 251-260.*
Paramanik, et al., "Direct Detection of Insertion/Deletion Polymorphisms in an Autosomal Region by Analyzing High-Density Markers in Individual Spermatozoa", Am. J. Hum. Genet., 71:1341-1352, 2002.

Li, et al., "Carotid Remodeling of Hypertensive Subjects and Polymorphism of the Antiotensin-Converting Enzyme Gene", Chinese Medical Journal 2004; 117(1) 49-53.
Seabury, et al., "Comparative PRNP Genotyping of U.S. Cattle Sires for Potential Associate with BSE", Mammalian Genome, vol. 15, pp. 828-833, 2004.
Butler, "Genetics and Genomics of Core Short Tandem Repeat Loci Used in Human Identity Testing", J. Forensic Sci., vol. 51, No. 2, Mar. 2006.
Caldas, et al., "P-23 Autosomal Mini-Indels Markers as a Tool to Improve Analysis on Low Quality Forensic Samples", $22^{nd}$ Congress of the International Society for Forensic Genetics, Aug. 21-25, 2007, Kopenhagen.
Edwards, et al., "Multiplex PCR: Advantages, Development, and Applications", PCR Methods Appl., 3:64-75, 1994.
Henegariu, et al., "Multiplex PCR: Critical Parameters and Step-by-Step Protocol", BioTechniques, 23:504-511, Sep. 1997.
"Mentype® DIPplex/ R&D Prototype", Aug. 2007.
Weber, et al., "Human Diallelic Insertion/D3eletion Polymorphisms", Am. J. Hum. Genet., 71:854-862, 2002.
Bhangale, et al., "Comprehensive Identification and Characterization of Diallelic Insertion-Deletion Polymorphisms in 330 Human Candidate Genes", Human Molecular Genetics, vol. 14, No. 1, pp. 59-69, 2005.
Manaster, et al., "InSNP: A Tool for Automated Detection and Visualization of SNPs and InDels", Human Muation, 26(1) 11-19, 2005.
Mills, et al, "An Initial Map of Insertion and Deletion (INDEL) Variation in the Human Genome", Genome Res. Published Online Aug. 10, 2006.

(Continued)

*Primary Examiner* — Young J Kim
(74) *Attorney, Agent, or Firm* — Fanelli Hang & Kilger PLLC

(57) ABSTRACT

The present invention relates to a DNA profiling assay comprising the following steps, providing a sample to be analyzed, providing reagents, enzyme and primeroligonucleotides which are necessary for simultaneous polymerase chain reaction amplification of at least 20 loci, amplifying the loci, detecting the amplification products, wherein the amplification products and the loci to be amplified are characterized by the following features, each locus to be amplified is characterized by at least one deletion-insertion polymorphism known to be present in the population, wherein the two alleles from each locus differ in size by more than 2 nucleotides and less than 100 nucleotides, a first set of at least two amplification products ranging in size from about 20 nucleotides to about 300 nucleotides stemming from at least two different loci carries a first label, a second set of at least two amplification products ranging in size from about 20 nucleotides to about 300 nucleotides stemming from at least two different loci carries a second label, a third set of at least two amplification products ranging in size from about 20 nucleotides to about 300 nucleotides stemming from at least two different loci carries a third label, label one, label two and label three are each different fluorescent labels which can he differentiated and simultaneously detected by a multi-color detector in combination with, e.g. a DNA sequencing device.

10 Claims, 4 Drawing Sheets

(56) References Cited

OTHER PUBLICATIONS

Li, et al., "SNP Genotyping by Multiplex Amplification ad Microarrays Assay for Forensic Application", Forensic Science International, 162(2006), pp. 74-79.

Jasinska, et al., "Repetitive Sequences that Shape the Human Transcriptome", FEBS Letters, 567(2004), pp. 136-141.

Kwok, "Methods for Genotyping Single Nucleotide Polymorphisms", Annu. Rev. Genomics Hum. Genet., 2:235-258, 2001.

Chamberlain, et al., "Deletion Screening of the Duchenne Muscular Dystropphy Locus Via Multiplex DNA Amplification", Nucleic Acids Research, vol. 16, No. 23, 1988.

Pena; "Public Safety: DNA Determination of Genetic Identity"; pp. 1-15, Jun. 2005.

Bastos-Rodrigues, et al., "The Genetic Structure of Human Populations Studied Through Short Insertion-Deletion Polymorphisms", Annals of Human Genetics, 70,658-665, Mar. 2006.

Weber, et al., "Human Diallelic Insertion/Deletion Polymorphism", Am. J. Hum. Genet., 71:854-862, Apr. 2002.

Bhangale, et al., "Comprehensive identification and characterization of diallelic insertion—deletion polymorphisms in 330 human candidate genes" Human Molecular Genetics, Nov. 2004, vol. 14, No. 1, pp. 59-69.

Akane, el al., "Sex Determination of Forensic Samples by Dual PCR Amplification of an X-Y Homologous Gene", Forensic Science International, 52, pp. 143-148, 1992.

Sullivan, et al., "A Rapid and Quantitative DNA Sex Test: Fluorescence-Based PCR Analysis of X-Y Homologous Gene Amelogenin", Biotechniques, 15(4):636-8, 640-1, Oct. 1993.

Alonso, et al., "Specific Quantification of Human Genomes from Low Copy Number DNA Samples in Forensic and Ancient DNA Studies", Croat. Med. J., 44, 273-250, 2003.

Third Party Observations received by the EPO for EP Patent Application No. 09 73 7904.4, pp. 1-10, Feb. 1, 2012.

Ghebranious, et al., "Human Insertion/Deletion (indel) Polymorhisms", Am. J. Hum. Genet., vol. 71, No. 4 Supplement, p. 461 (2002).

Sanchez, et al., "A Multiplex Assay with 52 Single Nucleotide Polymorphisms for Human Indentification", 52plex (2006).

\* cited by examiner

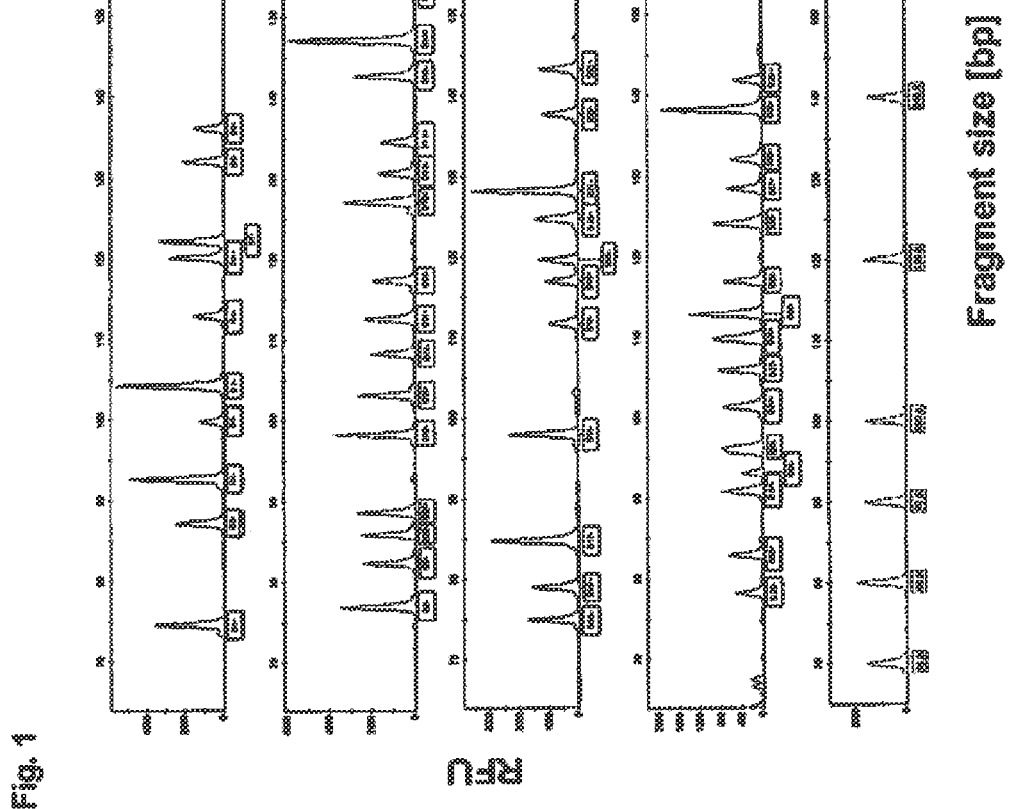

| DIP Locus Name | Seq ID NO. of Allele | | Seq ID NO. of PCR Primer | |
|---|---|---|---|---|
| | Deletion (-DIP) | Insertion (+DIP) | Forward | Reverse |
| DIP NO. 1 | SEQ ID NO. 1 | SEQ ID NO. 2 | SEQ ID NO. 125 | SEQ ID NO. 126 |
| DIP NO. 1 | SEQ ID NO. 1 | SEQ ID NO. 2 | SEQ ID NO. 267 | SEQ ID NO. 268 |
| DIP NO. 2 | SEQ ID NO. 3 | SEQ ID NO. 4 | SEQ ID NO. 127 | SEQ ID NO. 128 |
| DIP NO. 3 | SEQ ID NO. 5 | SEQ ID NO. 6 | SEQ ID NO. 129 | SEQ ID NO. 130 |
| DIP NO. 4 | SEQ ID NO. 7 | SEQ ID NO. 8 | SEQ ID NO. 131 | SEQ ID NO. 132 |
| DIP NO. 5 | SEQ ID NO. 9 | SEQ ID NO. 10 | SEQ ID NO. 133 | SEQ ID NO. 134 |
| DIP NO. 6 | SEQ ID NO. 11 | SEQ ID NO. 12 | SEQ ID NO. 135 | SEQ ID NO. 136 |
| DIP NO. 7 | SEQ ID NO. 13 | SEQ ID NO. 14 | SEQ ID NO. 137 | SEQ ID NO. 138 |
| DIP NO. 8 | SEQ ID NO. 15 | SEQ ID NO. 16 | SEQ ID NO. 139 | SEQ ID NO. 140 |
| DIP NO. 8 | SEQ ID NO. 15 | SEQ ID NO. 16 | SEQ ID NO. 287 | SEQ ID NO. 288 |
| DIP NO. 9 | SEQ ID NO. 17 | SEQ ID NO. 18 | SEQ ID NO. 141 | SEQ ID NO. 142 |
| DIP NO. 10 | SEQ ID NO. 19 | SEQ ID NO. 20 | SEQ ID NO. 143 | SEQ ID NO. 144 |
| DIP NO. 11 | SEQ ID NO. 21 | SEQ ID NO. 22 | SEQ ID NO. 145 | SEQ ID NO. 146 |
| DIP NO. 12 | SEQ ID NO. 23 | SEQ ID NO. 24 | SEQ ID NO. 147 | SEQ ID NO. 148 |
| DIP NO. 13 | SEQ ID NO. 25 | SEQ ID NO. 26 | SEQ ID NO. 149 | SEQ ID NO. 150 |
| DIP NO. 14 | SEQ ID NO. 27 | SEQ ID NO. 28 | SEQ ID NO. 151 | SEQ ID NO. 152 |
| DIP NO. 15 | SEQ ID NO. 29 | SEQ ID NO. 30 | SEQ ID NO. 153 | SEQ ID NO. 154 |
| DIP NO. 15 | SEQ ID NO. 29 | SEQ ID NO. 30 | SEQ ID NO. 281 | SEQ ID NO. 282 |
| DIP NO. 16 | SEQ ID NO. 31 | SEQ ID NO. 32 | SEQ ID NO. 155 | SEQ ID NO. 156 |
| DIP NO. 17 | SEQ ID NO. 33 | SEQ ID NO. 34 | SEQ ID NO. 157 | SEQ ID NO. 158 |
| DIP NO. 17 | SEQ ID NO. 33 | SEQ ID NO. 34 | SEQ ID NO. 273 | SEQ ID NO. 274 |
| DIP NO. 18 | SEQ ID NO. 35 | SEQ ID NO. 36 | SEQ ID NO. 159 | SEQ ID NO. 160 |
| DIP NO. 18 | SEQ ID NO. 35 | SEQ ID NO. 36 | SEQ ID NO. 277 | SEQ ID NO. 278 |
| DIP NO. 19 | SEQ ID NO. 37 | SEQ ID NO. 38 | SEQ ID NO. 161 | SEQ ID NO. 162 |
| DIP NO. 19 | SEQ ID NO. 37 | SEQ ID NO. 38 | SEQ ID NO. | SEQ ID NO. |

FIG. 2

| | | | 278 | 280 |
|---|---|---|---|---|
| DIP NO. 20 | SEQ ID NO. 39 | SEQ ID NO. 40 | SEQ ID NO. 183 | SEQ ID NO. 184 |
| DIP NO. 20 | SEQ ID NO. 39 | SEQ ID NO. 40 | SEQ ID NO. 275 | SEQ ID NO. 276 |
| DIP NO. 21 | SEQ ID NO. 41 | SEQ ID NO. 42 | SEQ ID NO. 165 | SEQ ID NO. 166 |
| DIP NO. 22 | SEQ ID NO. 43 | SEQ ID NO. 44 | SEQ ID NO. 167 | SEQ ID NO. 168 |
| DIP NO. 23 | SEQ ID NO. 45 | SEQ ID NO. 46 | SEQ ID NO. 169 | SEQ ID NO. 170 |
| DIP NO. 24 | SEQ ID NO. 47 | SEQ ID NO. 48 | SEQ ID NO. 171 | SEQ ID NO. 172 |
| DIP NO. 25 | SEQ ID NO. 49 | SEQ ID NO. 50 | SEQ ID NO. 173 | SEQ ID NO. 174 |
| DIP NO. 26 | SEQ ID NO. 51 | SEQ ID NO. 52 | SEQ ID NO. 175 | SEQ ID NO. 176 |
| DIP NO. 27 | SEQ ID NO. 53 | SEQ ID NO. 54 | SEQ ID NO. 177 | SEQ ID NO. 178 |
| DIP NO. 28 | SEQ ID NO. 55 | SEQ ID NO. 56 | SEQ ID NO. 179 | SEQ ID NO. 180 |
| DIP NO. 29 | SEQ ID NO. 57 | SEQ ID NO. 58 | SEQ ID NO. 181 | SEQ ID NO. 182 |
| DIP NO. 29 | SEQ ID NO. 57 | SEQ ID NO. 58 | SEQ ID NO. 271 | SEQ ID NO. 272 |
| DIP NO. 30 | SEQ ID NO. 59 | SEQ ID NO. 60 | SEQ ID NO. 183 | SEQ ID NO. 184 |
| DIP NO. 30 | SEQ ID NO. 59 | SEQ ID NO. 60 | SEQ ID NO. 283 | SEQ ID NO. 284 |
| DIP NO. 31 | SEQ ID NO. 61 | SEQ ID NO. 62 | SEQ ID NO. 185 | SEQ ID NO. 186 |
| DIP NO. 32 | SEQ ID NO. 63 | SEQ ID NO. 64 | SEQ ID NO. 187 | SEQ ID NO. 188 |
| DIP NO. 32 | SEQ ID NO. 63 | SEQ ID NO. 64 | SEQ ID NO. 269 | SEQ ID NO. 270 |
| DIP NO. 33 | SEQ ID NO. 65 | SEQ ID NO. 66 | SEQ ID NO. 189 | SEQ ID NO. 190 |
| DIP NO. 33 | SEQ ID NO. 65 | SEQ ID NO. 66 | SEQ ID NO. 285 | SEQ ID NO. 286 |
| DIP NO. 34 | SEQ ID NO. 67 | SEQ ID NO. 68 | SEQ ID NO. 191 | SEQ ID NO. 192 |
| DIP NO. 35 | SEQ ID NO. 69 | SEQ ID NO. 70 | SEQ ID NO. 193 | SEQ ID NO. 194 |
| DIP NO. 36 | SEQ ID NO. 71 | SEQ ID NO. 72 | SEQ ID NO. 195 | SEQ ID NO. 196 |
| DIP NO. 37 | SEQ ID NO. 73 | SEQ ID NO. 74 | SEQ ID NO. 197 | SEQ ID NO. 198 |
| DIP NO. 38 | SEQ ID NO. 75 | SEQ ID NO. 76 | SEQ ID NO. 199 | SEQ ID NO. 200 |
| DIP NO. 39 | SEQ ID NO. 77 | SEQ ID NO. 78 | SEQ ID NO. 201 | SEQ ID NO. 202 |
| DIP NO. 40 | SEQ ID NO. 79 | SEQ ID NO. 80 | SEQ ID NO. 203 | SEQ ID NO. 204 |
| DIP NO. 41 | SEQ ID NO. 81 | SEQ ID NO. 82 | SEQ ID NO. 205 | SEQ ID NO. 206 |
| DIP NO. 41 | SEQ ID NO. 81 | SEQ ID NO. 82 | SEQ ID NO 251 | SEQ ID NO 252 |
| DIP NO. 42 | SEQ ID NO. 83 | SEQ ID NO. 84 | SEQ ID NO. 207 | SEQ ID NO. 208 |
| DIP NO. 42 | SEQ ID NO. 83 | SEQ ID NO. 84 | SEQ ID NO 253 | SEQ ID NO |

FIG. 2 (continued)

| | | | | 254 |
|---|---|---|---|---|
| DIP NO. 43 | SEQ ID NO. 85 | SEQ ID NO. 86 | SEQ ID NO. 209 | SEQ ID NO. 210 |
| DIP NO. 43 | SEQ ID NO. 85 | SEQ ID NO. 86 | SEQ ID NO 255 | SEQ ID NO 256 |
| DIP NO. 44 | SEQ ID NO. 87 | SEQ ID NO. 88 | SEQ ID NO. 211 | SEQ ID NO. 212 |
| DIP NO. 44 | SEQ ID NO. 87 | SEQ ID NO. 88 | SEQ ID NO 257 | SEQ ID NO 258 |
| DIP NO. 45 | SEQ ID NO. 89 | SEQ ID NO. 90 | SEQ ID NO. 213 | SEQ ID NO. 214 |
| DIP NO. 45 | SEQ ID NO. 89 | SEQ ID NO. 90 | SEQ ID NO 259 | SEQ ID NO 260 |
| DIP NO. 46 | SEQ ID NO. 91 | SEQ ID NO. 92 | SEQ ID NO. 215 | SEQ ID NO. 216 |
| DIP NO. 46 | SEQ ID NO. 91 | SEQ ID NO. 92 | SEQ ID NO 261 | SEQ ID NO 262 |
| DIP NO. 47 | SEQ ID NO. 93 | SEQ ID NO. 94 | SEQ ID NO. 217 | SEQ ID NO. 218 |
| DIP NO. 47 | SEQ ID NO. 93 | SEQ ID NO. 94 | SEQ ID NO 263 | SEQ ID NO 264 |
| DIP NO. 48 | SEQ ID NO. 95 | SEQ ID NO. 96 | SEQ ID NO. 219 | SEQ ID NO. 220 |
| DIP NO. 49 | SEQ ID NO. 97 | SEQ ID NO. 98 | SEQ ID NO. 221 | SEQ ID NO. 222 |
| DIP NO. 50 | SEQ ID NO. 99 | SEQ ID NO. 100 | SEQ ID NO. 223 | SEQ ID NO. 224 |
| DIP NO. 51 | SEQ ID NO. 101 | SEQ ID NO. 102 | SEQ ID NO. 225 | SEQ ID NO. 226 |
| DIP NO. 51 | SEQ ID NO. 101 | SEQ ID NO. 102 | SEQ ID NO 265 | SEQ ID NO 266 |
| DIP NO. 52 | SEQ ID NO. 103 | SEQ ID NO. 104 | SEQ ID NO. 227 | SEQ ID NO. 228 |
| DIP NO. 53 | SEQ ID NO. 105 | SEQ ID NO. 106 | SEQ ID NO. 229 | SEQ ID NO. 230 |
| DIP NO. 54 | SEQ ID NO. 107 | SEQ ID NO. 108 | SEQ ID NO. 231 | SEQ ID NO. 232 |
| DIP NO. 55 | SEQ ID NO. 109 | SEQ ID NO. 110 | SEQ ID NO. 233 | SEQ ID NO. 234 |
| DIP NO. 56 | SEQ ID NO. 111 | SEQ ID NO. 112 | SEQ ID NO. 235 | SEQ ID NO. 236 |
| DIP NO. 57 | SEQ ID NO. 113 | SEQ ID NO. 114 | SEQ ID NO. 237 | SEQ ID NO. 238 |
| DIP NO. 58 | SEQ ID NO. 115 | SEQ ID NO. 116 | SEQ ID NO. 239 | SEQ ID NO. 240 |
| DIP NO. 59 | SEQ ID NO. 117 | SEQ ID NO. 118 | SEQ ID NO. 241 | SEQ ID NO. 242 |
| DIP NO. 60 | SEQ ID NO. 119 | SEQ ID NO. 120 | SEQ ID NO. 243 | SEQ ID NO. 244 |
| DIP NO. 61 | SEQ ID NO. 121 | SEQ ID NO. 122 | SEQ ID NO. 245 | SEQ ID NO. 246 |
| DIP NO. 62 | SEQ ID NO. 123 | SEQ ID NO. 124 | SEQ ID NO. 247 | SEQ ID NO. 248 |
| DIP NO. 63 | SEQ ID NO. 289 | SEQ ID NO. 290 | SEQ ID NO. 249 | SEQ ID NO. 250 |

FIG. 2 (continued)

SEQUENCE LISTING

```
<160> NUMBER OF SEQ ID NOS: 290

<210> SEQ ID NO 1
<211> LENGTH: 501
<212> TYPE: DNA
<213> ORGANISM: Homo sapiens

<400> SEQUENCE: 1
tcaaatgagg aaaacacttc acaccccaca ggttggttgt gaggctggtg taagactaca      60
cacatgaacc tgttttgtaa actgcagatt ggctacatga ctgggtgcag agttatttta     120
atcatgattg ctatttttag ggagataagg tcacttatct gcaaatgggt aagcaccaca     180
tatatgaact ataaactata tccatcctct cccaatgtgt aaattctaac ctgcactcaa     240
aggaaaaaca caaccgaca aatgactata ttttctaagg ctatccagga ctaatatgct      300
gtaaaggaaa gatgcaaaat ttaatcacac atcacacaca tatttataac tagcaaatca     360
gctcttcaca agaaggcata gttggggtta tggtttctag attgatcttt accaatgcag     420
ataaaatgca ctttctttaa ttcggagact gaatgcctgc caatttcagg gtgagtcatc     480
aaagaaggta ataatcttac c                                               501

<210> SEQ ID NO 2
<211> LENGTH: 505
<212> TYPE: DNA
<213> ORGANISM: Homo sapiens

<400> SEQUENCE: 2
tcaaatgagg aaaacacttc acaccccaca ggttggttgt gaggctggtg taagactaca      60
cacatgaacc tgttttgtaa actgcagatt ggctacatga ctgggtgcag agttatttta     120
atcatgattg ctatttttag ggagataagg tcacttatct gcaaatgggt aagcaccaca     180
tatatgaact ataaactata tccatcctct cccaatgtgt aaattctaac ctgcactcaa     240
aggaaaaaca caaacaaacc gacaaatgac tatattttct aaggctatcc aggactaata     300
tgctgtaaag gaaagatgca aaatttaatc acacatcaca cacatatttta taactagcaa    360 atcagctctt cacaagaagg catagttggg gttatggttt ctagattgat ctttaccaat     420
gcagataaaa tgcactttct ttaattcgga gactgaatgc ctgccaattt cagggtgagt     480
catcaaagaa ggtaataatc ttacc                                           505

<210> SEQ ID NO 3
<211> LENGTH: 501
<212> TYPE: DNA
<213> ORGANISM: Homo sapiens

<400> SEQUENCE: 3
tagtttctga tcataagcaa catgcacaca aaagaggaat ctcatgtgtg aatttgtctt      60
ttttttttaa taggaaggat tctgcagcta ccatgcaaag atacttgcat atggtctgtt     120
tacacataga atttattgtc tagccagggc ccattttaaa aagaaaagag aacaaaagga     180
ctaacggcaa tatacaagca caaatgaaca agggctgcat ccttgctgac gaaattgcag     240
taactacaag gaaagtaatt atttcaacag gtatctgaaa taaaagctgg atagacccta     300
```

```
gagaagtgga gtggaattac agtaaaactt attttgaagg aaaaaatatt aagcatctta    360
tagacatata agtatctctg acattctcag ttaagaggtt cttagttgag taagtgatac    420
tggtcctctg ggatcaggtc acagacttac agagtcaaat gcctgtaaca agtatcacac    480
acaacctaaa acactcctgg a                                              501

<210> SEQ ID NO 4
<211> LENGTH: 505
<212> TYPE: DNA
<213> ORGANISM: Homo sapiens

<400> SEQUENCE: 4
tagtttctga tcataagcaa catgcacaca aagaggaat ctcatgtgtg aatttgtctt      60
ttttttttaa taggaaggat tctgcagcta ccatgcaaag atacttgcat atggtctgtt    120
tacacataga atttattgtc tagccagggc ccattttaaa aagaaaagag aacaaaagga    180
ctaacggcaa tatacaagca caaatgaaca agggctgcat ccttgctgac gaaattgcag    240
taactacaag taaggaaagt aattatttca acaggtatct gaaataaaag ctggatagac    300
cctagagaag tggagtggaa ttacagtaaa acttattttg aaggaaaaaa tattaagaca    360
tctatagaca tataagtatc tctgacattc tcagttaaga ggttcttagt tgagtaagtg    420
atactggtcc tctgggatca ggtcacagac ttacagagtc aaatgcctgt aacaagtatc    480
acacacaacc taaaacactc ctgga                                          505

<210> SEQ ID NO 5
<211> LENGTH: 405
<212> TYPE: DNA
<213> ORGANISM: Homo sapiens

<400> SEQUENCE: 5
tgggaaacac atgtgcttcc agaaaaagcc tagatgaatt gaaagtggcc tatttatagg     60
gatttccccc taagtgaaag gattccatga tccgttgaaa ttctgccata tcattttttgg   120 tatttttggt taaactgtct aggagttgag actacagtac agcactatca gtccagtgag    180
ttttttcttc taagagcctc acagaccata gttcagtttt aaaattgtac ttaaaatttt    240 tttccttttgg ttttgttttt taagaatttt attaacatat tatttctttt taaaaataat    300
tttaaattag ggttttttaa aaaattttca cagaaagtgg gtagagatgt tggaagggca    360
atttggctct cttcacttta atccaaacac ctggttttgt aaaag                    405

<210> SEQ ID NO 6
<211> LENGTH: 409
<212> TYPE: DNA
<213> ORGANISM: Homo sapiens

<400> SEQUENCE: 6
tgggaaacac atgtgcttcc agaaaaagcc tagatgaatt gaaagtggcc tatttatagg     60
gatttccccc taagtgaaag gattccatga tccgttgaaa ttctgccata tcattttttgg   120 tatttttggt taaactgtct aggagttgag acgtgctaca gtacagcact atcagtccag    180
tgagtttttt cttctaagag cctcacagac catagttcag ttttaaaatt gtacttaaaa    240
tttttttcct ttggttttgt ttttaaaga atttattaac atattatttc tttttaaaaa     300
taattttaaa ttagggtttt ttaaaaaatt ttcacagaaa gtgggtagag atgttggaag    360
ggcaatttgg ctctcttcac tttaatccaa acacctggtt ttgtaaaag                409
```

<210> SEQ ID NO 7
<211> LENGTH: 501
<212> TYPE: DNA
<213> ORGANISM: Homo sapiens

<400> SEQUENCE: 7

| | | |
|---|---|---|
| ctataaacat tcaagtatgg tatgtgagtg taagttttca tttctctggg attcttgtct | 60 |
| atgaattcaa ctgctgggtt gcgtggtgat tggaagttta gtttattaaa gaaacagtca | 120 |
| ctgtttccca gaaagactat gccattttcc attcccacca gcaatatgtg actcagtttc | 180 |
| cctctgtcct catcaacatg tggtgttttc attatcttgt attttaggca ttctaatagg | 240 |
| acttgtctta gtcttatttg ggctactgta acaaattacc atagactgag tagcttcaca | 300 |
| gaagtttatt tttcacagtt caggggaaag tttaagatct gggtgctggc atggtccatt | 360 |
| tctggtgagg tccaccttct aggctgcaaa cttctgactt cttgttgtag cctcatgtgg | 420 |
| tgaagagcag agaggagaaa caagctctct cgttactata atgagggcac taatctcatt | 480 |
| catgagagct ctgcccttat g | 501 |

<210> SEQ ID NO 8
<211> LENGTH: 512
<212> TYPE: DNA
<213> ORGANISM: Homo sapiens

<400> SEQUENCE: 8

| | | |
|---|---|---|
| ctataaacat tcaagtatgg tatgtgagtg taagttttca tttctctggg attcttgtct | 60 |
| atgaattcaa ctgctgggtt gcgtggtgat tggaagttta gtttattaaa gaaacagtca | 120 |
| ctgtttccca gaaagactat gccattttcc attcccacca gcaatatgtg actcagtttc | 180 |
| cctctgtcct catcaacatg tggtgttttc attatcttgt attttaggca ttctaatagg | 240 |
| acttgtctta ttgggcttat tgtcttattt gggctactgt aacaaattac catagactga | 300 |
| gtagcttcac agaagtttat ttttcacagt tcaggggaaa gtttaagatc tgggtgctgg | 360 |
| catggtccat ttctggtgag gtccaccttc taggctgcaa acttctgact tcttgttgta | 420 |
| gcctcatgtg gtgaagagca gagaggagaa acaagctctc tcgttactat aatgagggca | 480 |
| ctaatctcat tcatgagagc tctgccctta tg | 512 |

<210> SEQ ID NO 9
<211> LENGTH: 505
<212> TYPE: DNA
<213> ORGANISM: Homo sapiens

<400> SEQUENCE: 9

| | | |
|---|---|---|
| tggagaacta tgaagacttc tgtttagcct cacacagagg aaggcagaat aaacaaactg | 60 |
| aaatggccca acaagctac tgggttttc cctagactta gggtaaggaa aaggatcagg | 120 |
| cactgatttg acaaaaaaaa aaaaaaaaa aaaaaaagtg agcatacaga aaatattta | 180 |
| taggacactc tatgccatgc tcctggttca ctgcagatta tcaatcagtg gaaagtgata | 240 |
| gaagcaatgg atcagcagaa tgggtataga ggtaagacag cagttgcagc agcagtggtg | 300 |
| cttggctctg gtagggctgg tggagcaggg ttgctgtatt agaagagtca ggacttgttc | 360 |
| atatgtctgt ctctccctct cccccagatc atagctgaat acccagccct ggactttgca | 420 |
| gataataagt gtagcaaata tttttaaaa catttatcag catcatttaa attattacaa | 480 |
| aagtttataa attgaatcct atata | 505 |

<210> SEQ ID NO 10
<211> LENGTH: 509
<212> TYPE: DNA
<213> ORGANISM: Homo sapiens

<400> SEQUENCE: 10

```
tggagaacta tgaagacttc tgtttagcct cacacagagg aaggcagaat aaacaaactg    60
aaatggccca acaagctac tgggtttttc cctagactta gggtaaggaa aaggatcagg    120
cactgatttg acaaaaaaaa aaaaaaaaa aaaaaagtg agcatacaga aaatatttta    180
taggacactc tatgccatgc tcctggttca ctgcagatta tcaatcagtg gaaagtgata    240
gaagcaatgg aagcatcagc agaatgggta tagaggtaag acagcagttg cagcagcagt    300
ggtgcttggc tctggtaggg ctggtggagc agggttgctg tattagaaga gtcaggactt    360
gttcatatgt ctgtctctcc ctctccccca gatcatagct gaatacccag ccctggactt    420
tgcagataat aagtgtagca atatttttt aaaacattta tcagcatcat ttaaattatt    480
acaaaagttt ataaattgaa tcctatata                                      509
```

<210> SEQ ID NO 11
<211> LENGTH: 501
<212> TYPE: DNA
<213> ORGANISM: Homo sapiens

<400> SEQUENCE: 11

```
taattattcc ccactattga ggcaagacct tcctgagtat cccacccgat agcctgtgat    60
gatgttttc cagcctggct ggtgggaaca ctcactattc ctggccctgt gtgagtaacg    120
agcacttttc tgaaatcctt ttggatggtt ttcccatccc cacagactca caggcatggc    180
tgatccgtat tctccggaat acacaagaga acctcctgca gttccccagc aatctctcct    240
ttggcaactc tgttttgtac tctgtcctgt gactctagcc acgctggcct ccacagactc    300
ttcctccata tccatctcct gacctcagac aacctgatgc gctctgcttg gattcccctc    360
tctgcaccgt ggctttgaaa ctctctcaag acaataagct gtggcagtca agtgtggggc    420
ccacctcgtg tttcctgtct ttcagggtc actgtgattc attgcacgat gtccagtgtc    480
ttcaacactg ttgcttcata t                                              501
```

<210> SEQ ID NO 12
<211> LENGTH: 505
<212> TYPE: DNA
<213> ORGANISM: Homo sapiens

<400> SEQUENCE: 12

```
taattattcc ccactattga ggcaagacct tcctgagtat cccacccgat agcctgtgat    60
gatgttttc cagcctggct ggtgggaaca ctcactattc ctggccctgt gtgagtaacg    120
agcacttttc tgaaatcctt ttggatggtt ttcccatccc cacagactca caggcatggc    180
tgatccgtat tctccggaat acacaagaga acctcctgca gttccccagc aatctctcct    240
ttggcaactc tctttgtttt gtactctgtc ctgtgactct agccacgctg gcctccacag    300
actcttcctc catatccatc tcctgacctc agacaacctg atgcgctctg cttggattcc    360
cctctctgca ccgtggcttt gaaactctct caagacaata agctgtggca gtcaagtgtg    420
ggcccacct cgtgtttcct gtctttcagg ggtcactgtg attcattgca cgatgtccag    480
tgtcttcaac actgttgctt catat                                          505
```

<210> SEQ ID NO 13

```
<211> LENGTH: 501
<212> TYPE: DNA
<213> ORGANISM: Homo sapiens

<400> SEQUENCE: 13
agagaatgaa acagtggttc actggttggg gatagagaaa taaggagatg gaggtcaaag      60
gatacaaaat agcagatgtg tgggatgaac aagtctagag atctaatgta taacatgagg     120
actaaagtta atacaattgt attatattag ggattttttgc taaatgggta gattttagct    180
attcgtcacc aaaacaaagt atgtgagatg acagatatgt tcactggcta aactatgtgt     240
atcccataac accatgtaaa cctcaaatat acataataaa atttatttta atatgtaaat     300
gtaaaaatca ttcttaactt gagggctcta caaaaacagg acagacagga tatggtcagt    360
accaactagc cttagtttgg caacctctgt cctagataat aaaaaaagtg aaaaacagca    420
aacaaataaa actaaacctc tagtgctaca aagaacaat ttgaaatgat catgtcaata     480
ctgaaaaaag agaatggcaa a                                               501

<210> SEQ ID NO 14
<211> LENGTH: 505
<212> TYPE: DNA
<213> ORGANISM: Homo sapiens

<400> SEQUENCE: 14
agagaatgaa acagtggttc actggttggg gatagagaaa taaggagatg gaggtcaaag      60
gatacaaaat agcagatgtg tgggatgaac aagtctagag atctaatgta taacatgagg     120
actaaagtta atacaattgt attatattag ggattttttgc taaatgggta gattttagct    180
attcgtcacc aaaacaaagt atgtgagatg acagatatgt tcactggcta aactatgtgt     240
atcccataac acacaccatg taaacctcaa atatacataa taaaatttat tttaatatgt     300
aaatgtaaaa atcattctta acttgagggc tctacaaaaa caggacagac aggatatggt    360
cagtaccaac tagccttagt ttggcaacct ctgtcctaga taataaaaaa agtgaaaaac    420
agcaaacaaa taaaactaaa cctctagtgc tacaaaagaa caatttgaaa tgatcatgtc    480
aatactgaaa aaagagaatg gcaaa                                           505

<210> SEQ ID NO 15
<211> LENGTH: 505
<212> TYPE: DNA
<213> ORGANISM: Homo sapiens

<400> SEQUENCE: 15
aggatcgtcc tgcaggctcc accagactat caaactgaag ccaccaaaag ccctctcatg      60
tgacttcata cacagatcac ccagcacagt tctgatgata taagctgtca cttatctgca    120
agtgaactga atgtcaagat cagtggtttg tgatcttgcc atctgatgtc agatttagct    180
cacaggagat actcattaaa atcatttagg aagccaaata ggatgtacag caggtcaaaa    240
cccccaccac gaggaaggaa gggaagacat gacccatttt ctgcagactt ttactttagt    300
ttggtattat tctttgagag tcttcaacca ggattacaac tggcttgaat cctgctcatt    360
ctagtgtaag tgtgtaactt gctatgtgat attgtatggt gtggacagca agacaaaagg    420
gcatatttcc aatctctcta caaaagagga actagccaga acagctgcc aaaaatgctg     480 aaacagcctg tgacagtcat cccac                                           505

<210> SEQ ID NO 16
<211> LENGTH: 509
```

<212> TYPE: DNA
<213> ORGANISM: Homo sapiens

<400> SEQUENCE: 16

```
aggatcgtcc tgcaggctcc accagactat caaactgaag ccaccaaaag ccctctcatg    60
tgacttcata cacagatcac ccagcacagt tctgatgata taagctgtca cttatctgca   120
agtgaactga atgtcaagat cagtggtttg tgatcttgcc atctgatgtc agatttagct   180
cacaggagat actcattaaa atcatttagg aagccaaata ggatgtacag caggtcaaaa   240
cccccaccac gaggaaggaa ggaagggaag acatgaccca ttttctgcag acttttactt   300
tagtttggta ttattctttg agagtcttca accaggatta caactggctt gaatcctgct   360
cattctagtg taagtgtgta acttgctatg tgatattgta tggtgtggac agcaagacaa   420
aagggcatat ttccaatctc tctacaaaag aggaactagc cagaaacagc tgccaaaaat   480
gctgaaacag cctgtgacag tcatcccac                                    509
```

<210> SEQ ID NO 17
<211> LENGTH: 501
<212> TYPE: DNA
<213> ORGANISM: Homo sapiens

<400> SEQUENCE: 17

```
aaaaatataa taataatgaa ttaaaaaagg aagtttgatt gcatataacg tataaaatta    60
gagcaatttc ttcctgttgt gtttcacctg ctttgcctgg aaacttgaat ctaagatgtg   120
tgcccaccct accaacgagg aacaatggat cagctggcat cgagggcatt ctttcccaag   180
aaacccagct ttaaaatgtt tccacagtgg gctggattga agtgcatttg aaagcacaac   240
gggttgaatc ctgttttgtt gtccccatcc ctgatgacac agccccactg tgttcttctt   300
attacataaa gggcaccect tctgagtaaa gatgaagtca gggagtttct gtagagcggg   360
cctcccacac tgggccagct ggacggggtg aagcaagggg agctcagggc ctgtctgggg   420
catttaaatg aactgtggga agggctgaga tgaacctggg ccagagaact ttcaagaaca   480
gccagtttgg ccgggcgcgg t                                             501
```

<210> SEQ ID NO 18
<211> LENGTH: 506
<212> TYPE: DNA
<213> ORGANISM: Homo sapiens

<400> SEQUENCE: 18

```
aaaaatataa taataatgaa ttaaaaaagg aagtttgatt gcatataacg tataaaatta    60
gagcaatttc ttcctgttgt gtttcacctg ctttgcctgg aaacttgaat ctaagatgtg   120
tgcccaccct accaacgagg aacaatggat cagctggcat cgagggcatt ctttcccaag   180
aaacccagct ttaaaatgtt tccacagtgg gctggattga agtgcatttg aaagcacaac   240
gggttgaatc ctgttttgtt ttgttgtccc catccctgat gacacagccc cactgtgttc   300
ttcttattac ataaagggca cccttctga gtaaagatga agtcagggag tttctgtaga   360
gcgggcctcc cacactgggc cagctggacg gggtgaagca aggggagctc agggcctgtc   420
tggggcattt aaatgaactg tgggaagggc tgagatgaac ctgggccaga gaactttcaa   480
gaacagccag tttggccggg cgcggt                                       506
```

<210> SEQ ID NO 19
<211> LENGTH: 501
<212> TYPE: DNA

<213> ORGANISM: Homo sapiens

<400> SEQUENCE: 19

```
tgggaccttc gcacactgat gcctccccct ccaccccgaa caggagccta cagagatggt    60
tcatatcatg cctctctttg tgaacatggg cacacaagtg tgagcatata caaatttgct   120
tctggaattt ttgttgaaga gcttagtcgt ccctcataga atgcattatt ttgtcttcag   180
tggctttact tccaggctta tcagggaaga agtggtttga acatcagag ccctaaacaa    240
acaaacaaaa cagaactcag aattcaggct accagtctgg ctgatgcatc tctacacctt   300
caaacaaaga tttaccactt tattcaagtt ttagttatcc ataaatttgt gaaagtaaag   360
tggtggcatt ttaaaactct ctaaaaagga acaaaatgct cttttcaga gcttcaaatg     420
ggcacacgac agaaagaact tctggacatc gacagttcct ccgtgattct tgaagatgga   480
atcaccaagc taaacaccat t                                             501
```

<210> SEQ ID NO 20
<211> LENGTH: 506
<212> TYPE: DNA
<213> ORGANISM: Homo sapiens

<400> SEQUENCE: 20

```
tgggaccttc gcacactgat gcctccccct ccaccccgaa caggagccta cagagatggt    60
tcatatcatg cctctctttg tgaacatggg cacacaagtg tgagcatata caaatttgct   120
tctggaattt ttgttgaaga gcttagtcgt ccctcataga atgcattatt ttgtcttcag   180
tggctttact tccaggctta tcagggaaga agtggtttga acatcagag ccctaaacaa    240
acaaacaaag taaacagaa ctcagaattc aggctaccag tctggctgat gcatctctac    300
accttcaaac aaagatttac cactttattc aagttttagt tatccataaa tttgtgaaag   360
taaagtggtg gcattttaaa actctctaaa aaggaacaaa atgctctttt tcagagcttc   420
aaatgggcac acgacagaaa gaacttctgg acatcgacag ttcctccgtg attcttgaag   480
atggaatcac caagctaaac accatt                                        506
```

<210> SEQ ID NO 21
<211> LENGTH: 501
<212> TYPE: DNA
<213> ORGANISM: Homo sapiens

<400> SEQUENCE: 21

```
taaagccttc tgtaatgtaa acagaaatta cacacgctca catacacagg aaagtgaaca    60
gtctctttga agccccacag ccaatgggat attctgaatt agcaccatac atagaaccag   120
aggaagtttt catagagcat cctgggcaca agttcattt tctgtactta taaggcgatc    180
tgctccgtga gaaagctgcc gtgtagagct ggagttgaga gtcgtgggtt tatcccatca   240
tttacaacta ctgattgcct tttaaaatat gaacacattt attaagaacc acaacaaaac   300
ccattcctga ttaaaggata tcttttctt atcactggcc ctagccagtg attgttcttc    360
aaccaagagc tgggaggagt gctcctaagc aaagattttg gatgcaggaa aggaacactc   420
caatcccaca gggaagacca acagatgtgt attccagaca gacagagcct cactggcaga   480
gcagctggga agacgctgct g                                             501
```

<210> SEQ ID NO 22
<211> LENGTH: 505
<212> TYPE: DNA
<213> ORGANISM: Homo sapiens

<400> SEQUENCE: 22

```
taaagccttc tgtaatgtaa acagaaatta cacacgctca catacacagg aaagtgaaca    60
gtctctttga agccccacag ccaatgggat attctgaatt agcaccatac atagaaccag   120
aggaagtttt catagagcat cctgggcaca agttcatttt tctgtactta taaggcgatc   180
tgctccgtga gaaagctgcc gtgtagagct ggagttgaga gtcgtgggtt tatcccatca   240
tttacaacta ctgattgatt gccttttaaa atatgaacac atttattaag aaccacaaca   300
aaacccattc ctgattaaag gatatctttt tcttatcact ggccctagcc agtgattgtt   360
cttcaaccaa gagctgggag gagtgctcct aagcaaagat tttggatgca ggaaaggaac   420
actccaatcc cacagggaag accaacagat gtgtattcca gacagacaga gcctcactgg   480
cagagcagct gggaagacgc tgctg                                        505
```

<210> SEQ ID NO 23
<211> LENGTH: 501
<212> TYPE: DNA
<213> ORGANISM: Homo sapiens

<400> SEQUENCE: 23

```
gtgctggtct gctcctctgg tcctcttcag ccagcatggg actggtgagg aaaaggttgt    60
gctggactcc tcaccgcctg gctacctgac cttggtgttg agcttcaggt atgccacata   120
gtgtgtcagg agcagccttt ggaaggcacc gctgtagaag gcccaggccg ggatcaggct   180
cagaaagccc gccttaaaca gagagaagca tcagtgttgg ggaggaagga ataacaagta   240
cctcagttca tctttaaaaa tattttttc tgactactaa agtggagccc cagaaccttt    300
tatgtaattg ataaagttta agggtcttgt gacactttct cagctcacaa ggttttctca   360
gacgccaaag tagccagtcc ttttaaactc ctttggacga cctagtacaa tcagccctaa   420
ggattttttt ttctttgaga caaggtcttg ctctgtcacc caggctggag tgcagtggca   480
cgatcacgac ttactgcagc c                                            501
```

<210> SEQ ID NO 24
<211> LENGTH: 510
<212> TYPE: DNA
<213> ORGANISM: Homo sapiens

<400> SEQUENCE: 24

```
gtgctggtct gctcctctgg tcctcttcag ccagcatggg actggtgagg aaaaggttgt    60
gctggactcc tcaccgcctg gctacctgac cttggtgttg agcttcaggt atgccacata   120
gtgtgtcagg agcagccttt ggaaggcacc gctgtagaag gcccaggccg ggatcaggct   180
cagaaagccc gccttaaaca gagagaagca tcagtgttgg ggaggaagga ataacaagta   240
cctcagttca tctttgtggt ctttaaaaat attttttct gactactaaa gtggagcccc    300
agaaccttt atgtaattga taagtttaa gggtcttgtg acactttctc agctcacaag    360
gttttctcag acgccaaagt agccagtcct tttaaactcc tttggacgac ctagtacaat   420
cagccctaag gattttttt tctttgagac aaggtcttgc tctgtcaccc aggctggagt   480
gcagtggcac gatcacgact tactgcagcc                                   510
```

<210> SEQ ID NO 25
<211> LENGTH: 501
<212> TYPE: DNA
<213> ORGANISM: Homo sapiens

<400> SEQUENCE: 25

```
tggttaaact gcattagtaa gcgctcagca aagggctgcc cagcaccata gatgcggccg    60
tagttgaaga ttttggcatg ctcacggctg atgcccacag tagtggctgt cttactgtgt   120
agatcagtgc ccctgctctt cctgccctgc agtgtcatcc acccaaaggc tgtgcagcct   180
ggaagacaag caggagtgag aaaagcagct caggaacatt ctgcccaatg ttcatcagaa   240
ctgtcaatat gctgagggc tgggctgccc aaccccggc tcctgctcac catgcatgcc    300
ggcaaagtgg gcgtctccaa gcacagctgc aatccacagc tcttgggagt ccacatcagc   360
acccacaagg gtgtagccag gtggggcctg caccatggc ttcaactcac tgcctactcg    420
gtcaggctgt gggaagagtg agatacccaa atgagactct tcctacccca ttcctggagc   480
cagagttgac tgagaaagag c                                             501
```

<210> SEQ ID NO 26
<211> LENGTH: 509
<212> TYPE: DNA
<213> ORGANISM: Homo sapiens

<400> SEQUENCE: 26

```
tggttaaact gcattagtaa gcgctcagca aagggctgcc cagcaccata gatgcggccg    60
tagttgaaga ttttggcatg ctcacggctg atgcccacag tagtggctgt cttactgtgt   120
agatcagtgc ccctgctctt cctgccctgc agtgtcatcc acccaaaggc tgtgcagcct   180
ggaagacaag caggagtgag aaaagcagct caggaacatt ctgcccaatg ttcatcagaa   240
ctgtcaatat gcatccatcc tgaggggctg gctgcccca accccggctc ctgctcacca   300
tgcatgccgg caaagtgggc gtctccaagc acagctgcaa tccacagctc ttgggagtcc   360
acatcagcac ccacaagggt gtagccaggt gggcctgca ccatggcttt caactcactg    420
cctactcggt caggctgtgg gaagagtgag atacccaaat gagactcttc ctaccccatt   480
cctggagcca gagttgactg agaaagagc                                      509
```

<210> SEQ ID NO 27
<211> LENGTH: 509
<212> TYPE: DNA
<213> ORGANISM: Homo sapiens

<400> SEQUENCE: 27

```
ctcatttctg ataacacaga ttatggttct gaaagatttt cttataatat tcatgataat    60
tgcctataaa tcaaagtcta gagcctgata atgtatgctt tccccctttcc ttaacctttt   120
ctggttaaga gaagagaaaa ctattttaat gaggagaagg aaccatcaat ggcagagact   180
gaaggatgaa gtttgaaaga ataatgtagg ccaactattg caaatgagat ttggaggact   240
gtgcatgtgg cttgggactc atcatttcat ttggtattca gttttgttct gaggcagaaa   300
atcaattctg ttgaatcatg tgactttggg ataatttata tcagagcaag gataaaggaa   360
atgagcaagc aaggaacaca gttttccttt tttaaaaaat gtgttttggt ttttggtttg   420
acgtgtcacc tcagcaagct acttgccaat agcacaggaa ggaaatggca ccagagaaat   480
atcagacttg gatatgcttc caacagcca                                      509
```

<210> SEQ ID NO 28
<211> LENGTH: 517
<212> TYPE: DNA
<213> ORGANISM: Homo sapiens

<400> SEQUENCE: 28

```
ctcatttctg ataacacaga ttatggttct gaaagatttt cttataatat tcatgataat        60
tgcctataaa tcaaagtcta gagcctgata atgtatgctt tccccttcc ttaacctttt        120 ctggttaaga gaagagaaaa ctattttaat gaggagaagg aaccatcaat ggcagagact       180
gaaggatgaa gtttgaaaga ataatgtagg ccaactattg caaatgagat ttggaggact       240
gtgcatgtgg cctactgact tgggactcat catttcattt ggtattcagt tttgttctga       300
ggcagaaaat caattctgtt gaatcatgtg actttgggat aatttatatc agagcaagga       360 taaggaaat gagcaagcaa ggaacacagt tttccttttt taaaaaatgt gttttggttt        420
ttggtttgac gtgtcacctc agcaagctac ttgccaatag cacaggaagg aaatggcacc       480
agagaaatat cagacttgga tatgcttcca acagcca                                517

<210> SEQ ID NO 29
<211> LENGTH: 501
<212> TYPE: DNA
<213> ORGANISM: Homo sapiens

<400> SEQUENCE: 29
gactctagtt ccacggtggt tgtccactgg taataagtta agaatcaggg gaacgctaca        60
ccacatacac atgtatacac agcacataca catgtacaca cagacacaca cacacacaca       120
cacacacaca cacacacacc gagagagaat tctagtccag gttttgcttt tcagtcctat       180
ttagtagaag ctcaattaat taaaatttgt ttttcctgaa aattatttta gaaaatttaa       240
tttccaagta tacacgtgga aaagaagat atatagaaaa aattaacaat gcttctttga        300
taggattatg aatgattttt attttttct ttatactttg tttaaaattt tctacaaaat        360
tgtatatttt ttaataatta aggaaagaga aatcttttt taaaaaaata catttatttc       420
aaccatattg taacttctgt ttaactccat tgcctaattc caatggaaaa aatgtatcta       480
tctgtagcct tctttggaat a                                                  501

<210> SEQ ID NO 30
<211> LENGTH: 512
<212> TYPE: DNA
<213> ORGANISM: Homo sapiens

<400> SEQUENCE: 30
gactctagtt ccacggtggt tgtccactgg taataagtta agaatcaggg gaacgctaca        60
ccacatacac atgtatacac agcacataca catgtacaca cagacacaca cacacacaca       120
cacacacaca cacacacacc gagagagaat tctagtccag gttttgcttt tcagtcctat       180
ttagtagaag ctcaattaat taaaatttgt ttttcctgaa aattatttta gaaaatttaa       240
tttccaagta tacaatgctt acacacgtgg aaaagaagat atatagaaaa aaattaacaa       300
tgcttctttg ataggattat gaatgatttt tatttttttc tttatacttt gtttaaaatt       360
ttctacaaaa ttgtatattt tttaataatt aaggaaagag aaatcttttt ttaaaaaaat       420
acatttattt caaccatatt gtaacttctg tttaactcca ttgcctaatt ccaatggaaa       480
aaatgtatct atctgtagcc ttctttggaa ta                                      512

<210> SEQ ID NO 31
<211> LENGTH: 501
<212> TYPE: DNA
<213> ORGANISM: Homo sapiens

<400> SEQUENCE: 31
```

```
ccaaggagct gggattacag gtgcatgcca ccactcccag ctaatttttg tattttagt      60 agagacgggg tttcagcatg ttggccatgc tggtcttgaa ttcctgacct caagagatct    120
gcccgccttg gcctcccaaa gtgctggaat tacaggtgtg agccactgca cccagccttc    180
tccttatatt tcttaaccag tcagaatact cctttgttcc tcctaatctc tttaacttca    240
tgcagtcctc taaggaccag tgtgagtctc atatattcca tgaaatagaa tgaacttcct    300
attgtatctg aaattgttcc atttgagttg tagtctgaaa tgaaccactt tcactggaaa    360 atgtggggc aaataattaa ctctgctgag cctatttctg catatgcaaa ataagaataa     420
tttcactaat acctgccctt caacctccc aagatcctag gaaggattgg atatgtgtta    480
taaagttttg gtgagctgtt a                                              501
```

```
<210> SEQ ID NO 32
<211> LENGTH: 505
<212> TYPE: DNA
<213> ORGANISM: Homo sapiens

<400> SEQUENCE: 32
ccaaggagct gggattacag gtgcatgcca ccactcccag ctaatttttg tattttagt      60 agagacgggg tttcagcatg ttggccatgc tggtcttgaa ttcctgacct caagagatct    120
gcccgccttg gcctcccaaa gtgctggaat tacaggtgtg agccactgca cccagccttc    180
tccttatatt tcttaaccag tcagaatact cctttgttcc tcctaatctc tttaacttca    240
tgcagtcctc taaggaagga ccagtgtgag tctcatatat tccatgaaat agaatgaact    300
tcctattgta tctgaaattg ttccatttga gttgtagtct gaaatgaacc actttcactg    360
gaaaatgtgg gggcaaataa ttaactctgc tgagcctatt tctgcatatg caaaataaga    420
ataatttcac taatacctgc cctttcaacc tcccaagatc ctaggaagga ttggatatgt    480
gttataaagt tttggtgagc tgtta                                          505
```

```
<210> SEQ ID NO 33
<211> LENGTH: 501
<212> TYPE: DNA
<213> ORGANISM: Homo sapiens

<400> SEQUENCE: 33
aaggacagcc atggcaaact acttcaaaag cacacagcac tgacaccaca gagtacttca     60
cagttgtatc atttagaggg gtttgtaata ctcacaacct tattacttaa aaatttctag    120
aacactggtg ctgcagggg cttttctctaa agcctatcta gtactgataa agaagaagct    180
gagatctaga gaaatgaaga gtcttactag ggtcataaac ccagtctgct gcagattgaa    240
ccaaaatttc agaggggaca tctctacgtg atgctgagac ctaaaactgg ccatggttac    300
ctagtatcta aagcgatgct gttccgccaa ctctacggag ttccacgaag ggatgtaaag    360 agggtcaac taaattctgt ttcctctatt tcaactgtc cagactataa tttcaagggt    420
tctaaattgt tttatatcta ttcatgtcac taaactttag cttaacaaaa atcctaaagc    480
tatattcttg agaagagaac a                                              501
```

```
<210> SEQ ID NO 34
<211> LENGTH: 519
<212> TYPE: DNA
<213> ORGANISM: Homo sapiens

<400> SEQUENCE: 34
aaggacagcc atggcaaact acttcaaaag cacacagcac tgacaccaca gagtacttca     60
```

```
cagttgtatc atttagaggg gtttgtaata ctcacaacct tattacttaa aaatttctag      120
aacactggtg ctgcagggggg ctttctctaa agcctatcta gtactgataa agaagaagct    180
gagatctaga gaaatgaaga gtcttactag ggtcataaac ccagtctgct gcagattgaa     240
ccaaaatttc atcctattct actctgaatg aggggacatc tctacgtgat gctgagacct    300
aaaactggcc atggttacct agtatctaaa gcgatgctgt tccgccaact ctacggagtt    360
ccacgaaggg atgtaaagag gggtcaacta aattctgttt cctctatttt caactgtcca   420
gactataatt tcaagggttc taaattgttt tatatctatt catgtcacta aactttagct    480
taacaaaaat cctaaagcta tattcttgag aagagaaca                           519
```

```
<210> SEQ ID NO 35
<211> LENGTH: 501
<212> TYPE: DNA
<213> ORGANISM: Homo sapiens

<400> SEQUENCE: 35
ttacaagaag acaaagtacg ccttctcccc taggaattct cttccacagc acctgaaaga    60
ggtaggtagg atggagtgag atgtggattt gaaaaccttg atcggaaaga gctttccttt    120
ctagttaggg ctgcccaatt ccagacaaca tgttttccag gaaaacacac acgcgcgcgc    180
gcacacacac acacacacac acacagacac gcctcttgtg tgctggtcca ttctcttgta    240
accatgtcag gtgaaggaac agccccgagg aaaggggcgc ggggttgtcc agtatccctc    300
tctgcaccta gggcatcgct ccttctccag ccttcactgc ccaaagcccc aggtccctga   360
ggagcaaagg tgatggttct agggcaggag gggaaaaaca gagctcagtg tggaagaaag    420
agaaaactgg aggctaaatg ccaggaaatc accagaggga gagaatggga ggaaagaaag    480
gaacatttcc agttttggaa t                                              501
```

```
<210> SEQ ID NO 36
<211> LENGTH: 512
<212> TYPE: DNA
<213> ORGANISM: Homo sapiens

<400> SEQUENCE: 36
ttacaagaag acaaagtacg ccttctcccc taggaattct cttccacagc acctgaaaga    60
ggtaggtagg atggagtgag atgtggattt gaaaaccttg atcggaaaga gctttccttt    120
ctagttaggg ctgcccaatt ccagacaaca tgttttccag gaaaacacac acgcgcgcgc    180
gcacacacac acacacacac acacagacac gcctcttgtg tgctggtcca ttctcttgta    240
accatgtcag ggaagtctga ggtgaaggaa cagccccgag gaaaggggcg cggggttgtc    300
cagtatccct ctctgcacct agggcatcgc tccttctcca gccttcactg cccaaagccc    360
caggtccctg aggagcaaag gtgatggttc tagggcagga ggggaaaaac agagctcagt    420
gtggaagaaa gagaaaactg gaggctaaat gccaggaaat caccagaggg agagaatggg    480
aggaaagaaa ggaacatttc cagttttgga at                                  512
```

```
<210> SEQ ID NO 37
<211> LENGTH: 501
<212> TYPE: DNA
<213> ORGANISM: Homo sapiens

<400> SEQUENCE: 37
tcaaaaaaaa aaaaaaaact gatgggtgct ggggaggact gatagaactg aatgtgcagg    60
```

```
gctccaaggg catggtgtgt ggttacagga ataagcagtt cggtttcagt ataaatagct      120
atccccagag ccttgcaaag atggaactgg ctgccttgtt cagtagtgag ctccccacca      180
ctggagctgt gaaggcagaa gccggggtgg ggagggcgac tataaagagg attcctgtgt      240
tggttagcag actagaccag ggtcagtgag cttttctat aaagggccag atagtaaata       300
cttgtggctt cgtgaaccag atggtctctg ctgcaactac ccagttctgc cattatagca      360
caaaagcagc tacataggcc ataggtaaat gaatgagaat gactgtgcat aaataaaaat      420
atttatgggc aatgaaattt gaatttcacg taattttcac atatcatgaa atattattct      480
tcttcagctt ttttttttcc c                                                501

<210> SEQ ID NO 38
<211> LENGTH: 506
<212> TYPE: DNA
<213> ORGANISM: Homo sapiens

<400> SEQUENCE: 38
tcaaaaaaaa aaaaaaaact gatgggtgct ggggaggact gatagaactg aatgtgcagg      60
gctccaaggg catggtgtgt ggttacagga ataagcagtt cggtttcagt ataaatagct      120
atccccagag ccttgcaaag atggaactgg ctgccttgtt cagtagtgag ctccccacca      180
ctggagctgt gaaggcagaa gccggggtgg ggagggcgac tataaagagg attcctgtgt      240
tggttagcag agtggactag accagggtca gtgagctttt tctataaagg gccagatagt      300
aaatacttgt ggcttcgtga accagatggt ctctgctgca actacccagt tctgccatta      360
tagcacaaaa gcagctacat aggccatagg taaatgaatg agaatgactg tgcataaata      420
aaaatattta tgggcaatga aatttgaatt tcacgtaatt ttcacatatc atgaaatatt      480
attcttcttc agctttttt tttccc                                            506

<210> SEQ ID NO 39
<211> LENGTH: 506
<212> TYPE: DNA
<213> ORGANISM: Homo sapiens

<400> SEQUENCE: 39
accacattat aacagaagaa tgaaaaataa ctagacagtt cgatataatt attttactc       60 ttttaaaaca cacccatgtt tcccagccat cattttcagc tcgcttcctc catccacctc      120
gcctcatggt ggagcttctg tattggggag gaaaaaaaa atgtcaattt tataacataa       180
tgtatttcta aatgatattt tatttcaata tcaagaaaat gagaaattaa attcaaatgt      240
ccaactgatg aaagtataca atattaagta aacttttct gaagttctcc attctccagc       300
tttacaagtg aaatttgtct ataaaacacc ctcctacaca tgtttaaatt gtaactctta      360
tatttaaaat tcaatagaaa aatatctta tgcattcctg agcaccaatc ctaacattca       420
cttacataaa acaccaaatc caactaacat ggccatgctt actttacttg ttaccattat      480
ataagacaat ctaacaaaac atttcc                                           506

<210> SEQ ID NO 40
<211> LENGTH: 511
<212> TYPE: DNA
<213> ORGANISM: Homo sapiens

<400> SEQUENCE: 40
accacattat aacagaagaa tgaaaaataa ctagacagtt cgatataatt attttactc       60 ttttaaaaca cacccatgtt tcccagccat cattttcagc tcgcttcctc catccacctc      120
```

```
gcctcatggt ggagcttctg tattggggag gaaaaaaaaa atgtcaattt tataacataa    180
tgtatttcta aatgatattt tatttcaata tcaagaaaat gagaaattaa attcaaatgt    240
ccaactgatg aaagtcaagt atacaatatt aagtaaactt tttctgaagt tctccattct    300
ccagctttac aagtgaaatt tgtctataaa cacccctcct acacatgttt aaattgtaac    360
tcttatattt aaaattcaat agaaaaatat ctttatgcat tcctgagcac caatcctaac    420
attcacttac ataaaacacc aaatccaact aacatggcca tgcttacttt acttgttacc    480
attatataag acaatctaac aaaacatttc c                                   511
```

```
<210> SEQ ID NO 41
<211> LENGTH: 501
<212> TYPE: DNA
<213> ORGANISM: Homo sapiens

<400> SEQUENCE: 41
cgaccttgtc cacgttcaca gctttgagcc ccatcaggtc gggcagctgg tcaatgatga     60
cgtcccggtt ggccttgacc ttgtgtaccc gcttgatgct gtggtgctgc caggcggtcc    120
agtagatgaa gtcccccagc agggtgaacc tgaaaatgtg tgggagcttg tccttcagga    180
gggtctgcct cttcgtctca tcgacactga tcgcctgcag aatggcaaag atacaggtct    240
ggatgggcca gggccatgcc aacgagagcc aaccctgacc ctgcctcggg cctgagctgc    300
cccaaacgag acgggttcaa cacccaggag cctcaacttc acctgcacct tgccaggtac    360
cataaaacgc caggtatcac ggctctccag gggtgctgga taaatgacgt tttttctttt    420
cttttttttg agattctgag acagagtctc tccctgttgc ccaggctgga gtgcagtggt    480
gagatctcgg ctcactgcaa c                                              501
```

```
<210> SEQ ID NO 42
<211> LENGTH: 507
<212> TYPE: DNA
<213> ORGANISM: Homo sapiens

<400> SEQUENCE: 42
cgaccttgtc cacgttcaca gctttgagcc ccatcaggtc gggcagctgg tcaatgatga     60
cgtcccggtt ggccttgacc ttgtgtaccc gcttgatgct gtggtgctgc caggcggtcc    120
agtagatgaa gtcccccagc agggtgaacc tgaaaatgtg tgggagcttg tccttcagga    180
gggtctgcct cttcgtctca tcgacactga tcgcctgcag aatggcaaag atacaggtct    240
ggatgggcca gggcaatggc catgccaacg agagccaacc ctgaccctgc ctcgggcctg    300
agctgcccca acgagacggg ttcaacaccc aggagcctca acttcacctg caccttgcc    360 aggtaccata aaacgccagg tatcacggct ctccaggggt gctggataaa tgacgttttt    420
tcttttcttt ttttgagat tctgagacag agtctctccc tgttgcccag gctggagtgc    480
agtggtgaga tctcggctca ctgcaac                                        507
```

```
<210> SEQ ID NO 43
<211> LENGTH: 501
<212> TYPE: DNA
<213> ORGANISM: Homo sapiens

<400> SEQUENCE: 43
tcacacttga aactggataa agttttcgag tatttgatat gcttttggcc attcttaact     60
tttaatttat actgtatatt gacattaact taattgtttt tactgacatt cttaattgct    120
```

```
ttttggaatt cattagctgg tataatacta agtaataaaa tacgttgtgt ttttctaaag      180
gcatctgaaa tagtggagct aaatactaaa actgggataa aaataatggt aattttagct      240
tacaaataaa caaatgtgag gtctctattt tacttatgga agtagaagga catcctcatg      300
taggttctac ctatgtttac ttgattaagt agaaaaaatt attagtttat tctgtagcca      360
aaaataaaat ggtgaaatga ttggtatata ttattgaatg atatatataa tgaatggtat      420
atatattaat gatatactta gataaaattg ttttaaaaat tgagattttg ttcttgacca      480
gcttggccaa catggcgaaa c                                                501

<210> SEQ ID NO 44
<211> LENGTH: 507
<212> TYPE: DNA
<213> ORGANISM: Homo sapiens

<400> SEQUENCE: 44
tcacacttga aactggataa agttttcgag tatttgatat gcttttggcc attcttaact       60
tttaatttat actgtatatt gacattaact taattgtttt tactgacatt cttaattgct      120
ttttggaatt cattagctgg tataatacta agtaataaaa tacgttgtgt ttttctaaag      180
gcatctgaaa tagtggagct aaatactaaa actgggataa aaataatggt aattttagct      240
tacaaataaa gacaaacaaa tgtgaggtct ctattttact tatggaagta gaaggacatc      300
ctcatgtagg ttctacctat gtttacttga ttaagtagaa aaaattatta gtttattctg      360
tagccaaaaa taaatggtg aaatgattgg tatatattat tgaatgatat ataatgaa       420 tggtatatat attaatgata tacttagata aaattgtttt aaaaattgag attttgttct      480
tgaccagctt ggccaacatg gcgaaac                                          507

<210> SEQ ID NO 45
<211> LENGTH: 501
<212> TYPE: DNA
<213> ORGANISM: Homo sapiens

<400> SEQUENCE: 45
gggaggtggg ggtgagcccc tcacagcctt gccctcccc aaggctggca acctgcctcc        60
cattgcccaa gagagagggc agggaacagg ctactgtcct tccctgtgga attgccgaga      120
aatctagcac cttgcatgct ggatctgggc tgcggggagg ctcttttttct ccctggcctc    180 cagtgcccac caggaggatc tgcgcacggt gcacagccca ccagagcact acagccttt      240 attgagtggg gcaagtgctg ggctgtggtc gtgccctgac agcatcttcc ccaggcagcg      300
gctctgtgga ggaggccata ctcccctagt tggccactgg ggccaccacc ctgaccacca      360
ctgtgcccct cattgttact gccttgtgag ataaaaactg attaaaccct tgtggctgtg      420
gttggctgac atggggtctg tgtttcacta actaactaac taactgcagg tggtggtatg      480
agactgtggg aagcagagaa c                                                501

<210> SEQ ID NO 46
<211> LENGTH: 506
<212> TYPE: DNA
<213> ORGANISM: Homo sapiens

<400> SEQUENCE: 46
gggaggtggg ggtgagcccc tcacagcctt gccctcccc aaggctggca acctgcctcc        60
cattgcccaa gagagagggc agggaacagg ctactgtcct tccctgtgga attgccgaga      120
aatctagcac cttgcatgct ggatctgggc tgcggggagg ctcttttttct ccctggcctc    180
```

```
cagtgcccac caggaggatc tgcgcacggt gcacagccca ccagagcact acagccttt     240 attgagtggg gtggggcaag tgctgggctg tggtcgtgcc ctgacagcat cttccccagg    300
cagcggctct gtggaggagg ccatactccc ctagttggcc actggggcca ccaccctgac    360
caccactgtg cccctcattg ttactgcctt gtgagataaa aactgattaa acctttgtgg    420
ctgtggttgg ctgacatggg gtctgtgttt cactaactaa ctaactaact gcaggtggtg    480
gtatgagact gtgggaagca gagaac                                        506

<210> SEQ ID NO 47
<211> LENGTH: 501
<212> TYPE: DNA
<213> ORGANISM: Homo sapiens

<400> SEQUENCE: 47
gcaggtcagt tgtcggttga cttttgcagat ggtcactgtg ctctctcaca tttctcaggc    60
ctgccctgga cagctgggct gactgggctc tggtttactt cgtctctcat catctagcag   120
gccagcctgg gtttgctcac atgactggac aggttttgaa gaaaagttca caaaggctcc   180
ttgaggctta gactcaagaa ttgacattga cacttttgcc actgcctatt ggctaaagcg   240
agtcttaagg ccaaggagta ggggaataga cttcacctcc tgctgggagg aactgcaaag   300
tcatattgca aagaggcata cttacagagg ggaataatgg tggtccttt tataaataac    360 tgttatttat tggcttgaca taagtgtaac tggtaaccac ttcatgcttt tccaagatgg   420
tcctaactac tgcccctcc tattcaattc agattgtcct ggagaaactt aaccaggtgg   480
aggctgacac ccaatcccca c                                             501

<210> SEQ ID NO 48
<211> LENGTH: 512
<212> TYPE: DNA
<213> ORGANISM: Homo sapiens

<400> SEQUENCE: 48
gcaggtcagt tgtcggttga cttttgcagat ggtcactgtg ctctctcaca tttctcaggc    60
ctgccctgga cagctgggct gactgggctc tggtttactt cgtctctcat catctagcag   120
gccagcctgg gtttgctcac atgactggac aggttttgaa gaaaagttca caaaggctcc   180
ttgaggctta gactcaagaa ttgacattga cacttttgcc actgcctatt ggctaaagcg   240
agtcttaagg ccaacctgga ttcaaggagt aggggaatag acttcacctc ctgctgggag   300
gaactgcaaa gtcatattgc aaagaggcat acttacagag gggaataatg gtggtccttt   360
ttataaataa ctgttatttta ttggcttgac ataagtgtaa ctggtaacca cttcatgctt   420
ttccaagatg gtcctaacta ctgcccctc ctattcaatt cagattgtcc tggagaaact   480
taaccaggtg gaggctgaca cccaatcccc ac                                 512

<210> SEQ ID NO 49
<211> LENGTH: 546
<212> TYPE: DNA
<213> ORGANISM: Homo sapiens

<400> SEQUENCE: 49
gatagcacac agtcccaact ggatgggaag gccagaaaac tggtacagcc aggcttagat    60
tgcactccaa atatcaatat atgaatctgg tacattttg ttactggctt aagaatgggc   120
ttttgtgaag gtattgatat gaaccttat agtaggaata tataaatgta tttaaaatat   180
```

```
tggtcaggtg ggtagggtgt tatgtgtatc ttttcaaaga gatcaaagtc aacattagaa      240
gtgaactatc tggcagtaag ctaaattctg ttggaacatc catggaaatt gccagtggca      300
gtaagctaaa ttctgttgga acatccatgg aaattgccag tagacgatcc aacaccctag      360
caaatctctt tatagctcct ttaactcagg aaacacacct tattgtcatg cattatggag      420
atcttggggc tacaaatgaa caagatgaaa atctgcgctt gcaagagcc catactttgc        480 cacagaggtg gtgctatccc ttaggagaag ttctaggaat ctgtggggc atttctctgg        540 tcataa                                                                  546

<210> SEQ ID NO 50
<211> LENGTH: 591
<212> TYPE: DNA
<213> ORGANISM: Homo sapiens

<400> SEQUENCE: 50
gatagcacac agtcccaact ggatgggaag gccagaaaac tggtacagcc aggcttagat        60
tgcactccaa atatcaatat atgaatctgg tacattttg ttactggctt aagaatgggc        120
ttttgtgaag gtattgatat gaacctttat agtaggaata tataaatgta tttaaaatat        180
tggtcaggtg ggtagggtgt tatgtgtatc ttttcaaaga gatcaaagtc aacattagaa        240
gtgaactatc tggcagtaag ctaaattctg ttggaacatc catggaaatt gccagtggca        300
gtaagctaaa ttctgttgga acatccatgg aaattgccag tggcagtaag ctaaattctg        360
ttggaacatc catggaaatt gccagtagac gatccaacac cctagcaaat ctctttatag        420
ctcctttaac tcaggaaaca caccttattg tcatgcatta tggagatctt ggggctacaa        480
atgaacaaga tgaaaatctg cgcttgcaaa gagcccatac tttgccacag aggtggtgct        540
atcccttagg agaagttcta ggaatctgtg gggcatttc tctggtcata a                  591

<210> SEQ ID NO 51
<211> LENGTH: 501
<212> TYPE: DNA
<213> ORGANISM: Homo sapiens

<400> SEQUENCE: 51
tgggaggccg aggcaggcag gtcacttgag gttgggagtt cgacaacagc ctgaccaaca        60
tggagaaacc ctgtctctac taaaaataca aaattagctg ggcgtggtgg tgcatgcctg        120
taatgccagc tactcgggag gctgaggcag gagaatcact taaacctggg aggcggaggt        180
tgcggtgaac caagatagca ccattgcact ccagcctggg caacaagagt gaaactccgt        240
ctcaaaaaga gttcacagtt tctcttttgc tttgattttc ttatctgccg gataacaata        300
gtattttgga aggcaggagg aattgtgaa agaaatgggt tttggggagt ggctgattgg         360
aggcaaatcc aaggacactc attgctggtg tgtgactcca ggcagttact cagcttttcc        420
aagcctcagt ttccttattg taaaacagga ccatggtcta gctagtagca ttcctatggt        480
gagtgaaata atatgtataa a                                                 501

<210> SEQ ID NO 52
<211> LENGTH: 515
<212> TYPE: DNA
<213> ORGANISM: Homo sapiens

<400> SEQUENCE: 52
tgggaggccg aggcaggcag gtcacttgag gttgggagtt cgacaacagc ctgaccaaca        60
tggagaaacc ctgtctctac taaaaataca aaattagctg ggcgtggtgg tgcatgcctg        120
```

```
taatgccagc tactcgggag gctgaggcag gagaatcact taaacctggg aggcggaggt    180
tgcggtgaac caagatagca ccattgcact ccagcctggg caacaagagt gaaactccgt    240
ctcaaaaaga gagagaaagc tgaagttcac agtttctctt ttgctttgat tttcttatct    300
gccggataac aatagtattt tggaaggcag gaggaattgt ggaaagaaat gggttttggg    360
gagtggctga ttggaggcaa atccaaggac actcattgct ggtgtgtgac tccaggcagt    420
tactcagctt ttccaagcct cagtttcctt attgtaaaac aggaccatgg tctagctagt    480
agcattccta tggtgagtga ataatatgt ataaa                                515
```

<210> SEQ ID NO 53
<211> LENGTH: 504
<212> TYPE: DNA
<213> ORGANISM: Homo sapiens

<400> SEQUENCE: 53

```
tcacagacac atacctcatt ttagctctac ttccaaatta cggggactga gacacccact     60
acctaaaatc ctatcgctgt gggaagcccc atttaaaggg gaaaagagga tgaggaggct    120
tttaggattg agatggggaa actgaggtca caggcctgcg ggctcccagt cacaggttgc    180
agagccaagt gagcacccag gtcacatccc atcagcttct acaataggaa atgccaccca    240 gccccgggc gggacaggtg gccactagga gaggggcagg ggtactagac gagaacccgg    300
ctccagagct ggggccatcg gcggtgctgg tgtggttact aatgagaagg taaacacggg    360
ggccacgggt ttcctgggtg aacacttgcc ccacccgctg tgaaacccta tgaaaagcaa    420
tttacttgag actgaagtta tttcagctgc aactggaaaa agagagtagg agttgctggg    480
gggaagtttg cttctaggac ctca                                           504
```

<210> SEQ ID NO 54
<211> LENGTH: 526
<212> TYPE: DNA
<213> ORGANISM: Homo sapiens

<400> SEQUENCE: 54

```
tcacagacac atacctcatt ttagctctac ttccaaatta cggggactga gacacccact     60
acctaaaatc ctatcgctgt gggaagcccc atttaaaggg gaaaagagga tgaggaggct    120
tttaggattg agatggggaa actgaggtca caggcctgcg ggctcccagt cacaggttgc    180
agagccaagt gagcacccag gtcacatccc atcagcttct acaataggaa atgccaccca    240 gccccgggc gggacaggtg gccactagga gagggacagg tggccactag gagaggggca    300
ggggtactag acgagaaccc ggctccagag ctggggccat cggcggtgct ggtgtggtta    360
ctaatgagaa ggtaaacacg ggggccacgg gtttcctggg tgaacacttg ccccacccgc    420
tgtgaaaccc tatgaaaagc aatttacttg agactgaagt tatttcagct gcaactggaa    480
aaagagagta ggagttgctg ggggaagtt tgcttctagg acctca                    526
```

<210> SEQ ID NO 55
<211> LENGTH: 501
<212> TYPE: DNA
<213> ORGANISM: Homo sapiens

<400> SEQUENCE: 55

```
tgccattatg tggcacgtga ctatatatat aaaatatatt ctcaatcttt aatgaacatt     60
tttggaaatc cagtgataac tggtaggttt ccatattcca tagaaagtta ataagaaaa    120
```

| | |
|---|---|
| attaaaggta tagtgacatt gtgtatggtt tctcttcatt tccggaaaat gccaaatttt | 180 |
| atgctacttg tcttttaaa agtcttaatc ttctctcatt atggttacca ccaagagtta | 240 |
| cattacatgt gcaattttga aactaattat aagagttgaa atcaagtat aacaaatcaa | 300 |
| aacattagct ctgctagcgt tccctttcgc aacaccacag aagacacata ttcccctagt | 360 |
| gtccaatttc ctaatatata tgactgaagc aatagcaccc ttgccaaaac actcagtact | 420 |
| caggtgatag acactacgag tactgcttga tttgtgaagc tctctcttaa attcttaagg | 480 |
| atgtgctctg taaaaagatc t | 501 |

<210> SEQ ID NO 56
<211> LENGTH: 509
<212> TYPE: DNA
<213> ORGANISM: Homo sapiens

<400> SEQUENCE: 56

| | |
|---|---|
| tgccattatg tggcacgtga ctatatatat aaaatatatt ctcaatcttt aatgaacatt | 60 |
| tttgaaaatc cagtgataac tggtaggttt ccatattcca tagaaagtta ataagaaaa | 120 |
| attaaaggta tagtgacatt gtgtatggtt tctcttcatt tccggaaaat gccaaatttt | 180 |
| atgctacttg tcttttaaa agtcttaatc ttctctcatt atggttacca ccaagagtta | 240 |
| cattacatgt gattaaatac aattttgaaa ctaattataa gagttgaaaa tcaagtataa | 300 |
| caaatcaaaa cattagctct gctagcgttt cctttcgcaa caccacagaa gacacatatt | 360 |
| cccctagtgt ccaatttcct aatatatatg actgaagcaa tagcacccttt gccaaaacac | 420 |
| tcagtactca ggtgatagac actacgagta ctgcttgatt tgtgaagctc tctcttaaat | 480 |
| tcttaaggat gtgctctgta aaaagatct | 509 |

<210> SEQ ID NO 57
<211> LENGTH: 516
<212> TYPE: DNA
<213> ORGANISM: Homo sapiens

<400> SEQUENCE: 57

| | |
|---|---|
| ctcctcaagt tctagccgca ttgcagggag gagtgggaga ggggcctgaa gaagactcca | 60 |
| gtggaacagc cacactctct ccccttctg ctggatggtc caactggcca cctgcctgaa | 120 |
| aatgagagcc tagagatcac ctacagccaa tccaggaaga ataacataga accccgggcc | 180 |
| agggaagcgg tctggaagtc agggtgctgg ccccacccc ctagctcctt cctgaggggc | 240 |
| tttgctcctg ccacttttgc tgggatgagc tcagaggtac cctgcaaaga gtgtgggaaa | 300 |
| atagaccttt tgaggaagaa attggagaag ggggacccag ctctgaaagc ctctctctct | 360 |
| ccactgggct gcattgcttg gcggtagctg tgactctgga cttaagggag gtcagaggga | 420 |
| ggaagggcaa gaatttggag ctgggtagag ggaaagctca tgacctgttc acaggctcta | 480 |
| ggacttacaa ctctgcttct atgtgtactc tggaca | 516 |

<210> SEQ ID NO 58
<211> LENGTH: 531
<212> TYPE: DNA
<213> ORGANISM: Homo sapiens

<400> SEQUENCE: 58

| | |
|---|---|
| ctcctcaagt tctagccgca ttgcagggag gagtgggaga ggggcctgaa gaagactcca | 60 |
| gtggaacagc cacactctct ccccttctg ctggatggtc caactggcca cctgcctgaa | 120 |
| aatgagagcc tagagatcac ctacagccaa tccaggaaga ataacataga accccgggcc | 180 |

```
agggaagcgg tctggaagtc agggtgctgg ccccaccccc ctagctcctt cctgaggggc    240
tttgctcctg cggtgcccag tcctgccact tttgctggga tgagctcaga ggtaccctgc    300
aaagagtgtg ggaaaataga ccttttgagg aagaaattgg agaaggggga cccagctctg    360
aaagcctctc tctctccact gggctgcatt gcttggcggt agctgtgact ctggacttaa    420
gggaggtcag agggaggaag ggcaagaatt tggagctggg tagagggaaa gctcatgacc    480
tgttcacagg ctctaggact tacaactctg cttctatgtg tactctggac a             531
```

<210> SEQ ID NO 59  
<211> LENGTH: 521  
<212> TYPE: DNA  
<213> ORGANISM: Homo sapiens

<400> SEQUENCE: 59

```
agggtactgg agccagatca caatgagcct tgaaagccaa gcttaaccag ttaatgaaag    60
acgatcattt gcttttcaga gacatagacc ctgatttgct tcctgataga taatgagtac    120
attaacttct ggcttagtaa gtgtcactta gttaaccaca ttactgcact gattcactaa    180
atgaacttcc attacctgac ttacttgccc aaaagaaaac atatcattca taaatctaat    240
aacaatttta atcccatttt tgtttagga tctaaagggt acctttagat tgttgctgaa     300
ttaccaagga atatcttgca tggtgagaaa aatcaaactc tagccctcaa ccctaaatct    360
cctagacttg aggagtttgt tccttggctt tgtccccagg tcatagtccc tcaataaaca    420
cttgttgagt ttggggtata accataaact atcaatgaat taagcaactg agctaggagc    480
cttgagcatt tctataagga caacttata gggcctggta a                         521
```

<210> SEQ ID NO 60  
<211> LENGTH: 539  
<212> TYPE: DNA  
<213> ORGANISM: Homo sapiens

<400> SEQUENCE: 60

```
agggtactgg agccagatca caatgagcct tgaaagccaa gcttaaccag ttaatgaaag    60
acgatcattt gcttttcaga gacatagacc ctgatttgct tcctgataga taatgagtac    120
attaacttct ggcttagtaa gtgtcactta gttaaccaca ttactgcact gattcactaa    180
atgaacttcc attacctgac ttacttgccc aaaagaaaac atatcattca taaatctaat    240
aacaatttta atcccatttt tgtttagga tcccattttt gtttaggatc taaagggtac     300
ctttagattg ttgctgaatt accaaggaat atcttgcatg gtgagaaaaa tcaaactcta    360
gccctcaacc ctaaatctcc tagacttgag gagtttgttc cttggctttg tccccaggtc    420
atagtccctc aataaacact tgttgagttt ggggtataac cataaactat caatgaatta    480
agcaactgag ctaggagcct tgagcatttc tataaggaac aacttatagg gcctggtaa    539
```

<210> SEQ ID NO 61  
<211> LENGTH: 501  
<212> TYPE: DNA  
<213> ORGANISM: Homo sapiens  
<220> FEATURE:  
<221> NAME/KEY: misc_feature  
<222> LOCATION: (272)..(272)  
<223> OTHER INFORMATION: n is a, c, g, or t

<400> SEQUENCE: 61

```
tttttaaagt agcttcagtc tcctttaatg tgaacaattg catactgact taatctcttc    60
```

```
ctctctcttc tcttccttca ctctctccct tcctctctct ttctattctc ctcccctcct    120
ccctgtaaaa gctaccacct catcctgggc accctggtta tatcaacttc agctatgagg    180
taatttttct ctttactaat tttgaccatt gtttgcgtta acaatgccct gggctctgta    240
aagaatagtg tgttgattct ttatcccaga tngtttctca agtggtcctg attttacagt    300
tcctaccacc agcttcccag tttaagctct gatggttggc ctcaagcctg tgtcgtccca    360
gcagcctccc gcctggccac tctgactcag tctgtcctcc taaatatggc cgtaagctta    420
cccatcatga accactactc agggaggctc catgataggg caaaaagtaa actctgacca    480
gcttggttct aacccagcta g                                              501

<210> SEQ ID NO 62
<211> LENGTH: 506
<212> TYPE: DNA
<213> ORGANISM: Homo sapiens

<400> SEQUENCE: 62
tttttaaagt agcttcagtc tcctttaatg tgaacaattg catactgact taatctcttc     60
ctctctcttc tcttccttca ctctctccct tcctctctct ttctattctc ctcccctcct    120
ccctgtaaaa gctaccacct catcctgggc accctggtta tatcaacttc agctatgagg    180
taatttttct ctttactaat tttgaccatt gtttgcgtta acaatgccct gggctctgta    240
aagaatagtg tgttgattct ttatcccaga taaagtggtt tctcaagtgg tcctgatttt    300
acagttccta ccaccagctt cccagtttaa gctctgatgg ttggcctcaa gcctgtgtcg    360
tcccagcagc ctcccgcctg ccactctga ctcagtctgt cctcctaaat atggccgtaa    420
gcttacccat catgaaccac tactcaggga ggctccatga tagggcaaaa agtaaactct    480
gaccagcttg gttctaaccc agctag                                        506

<210> SEQ ID NO 63
<211> LENGTH: 500
<212> TYPE: DNA
<213> ORGANISM: Homo sapiens

<400> SEQUENCE: 63
atacttgcct cctagcatat aagaaaagat gaagaatgtg tgtgatggat gtaaacacag     60
tgcctgtcac acaggaagca cccaacaaat ttttaccttc ttctttcttt tgtagaactc    120
acattctcag gctatcaatg ttgacaggac tgcattagtg agtctatatt tcctactgca    180
tcagtgagtt tctatattgg atgaaagtaa attaaatcaa atgggttcta atatcttttt    240
ctcttaaggt gcttacccct ttgaagtggt accagagcat aaggccaccg gtatgtagac    300
attttgttcc ttattccctg aaaatattag gcatgcatta aaattcccat attaagtgaa    360
atatcatgtc tactccacat gcagacatta atgggaaatt tagtttgtaa aaaatcatat    420
ctgtgtacac agttacaaat ttttgcaaag gaaaaatgaa taaatattc ctatagccat    480 aatggcaaag aaaacactgc                                               500

<210> SEQ ID NO 64
<211> LENGTH: 503
<212> TYPE: DNA
<213> ORGANISM: Homo sapiens

<400> SEQUENCE: 64
atacttgcct cctagcatat aagaaaagat gaagaatgtg tgtgatggat gtaaacacag     60
tgcctgtcac acaggaagca cccaacaaat ttttaccttc ttctttcttt tgtagaactc    120
```

```
acattctcag gctatcaatg ttgacaggac tgcattagtg agtctatatt tcctactgca    180
tcagtgagtt tctatattgg atgaaagtaa attaaatcaa atgggttcta atatctttt     240 ctcttaaggt gcttacccct ttgaagtggt accagagcat gataaggcca ccggtatgta    300
gacattttgt tccttattcc ctgaaaatat taggcatgca ttaaaattcc catattaagt    360
gaaatatcat gtctactcca catgcagaca ttaatgggaa atttagtttg taaaaaatca    420
tatctgtgta cacagttaca aattttgca  aggaaaaat gaataaaata ttcctatagc     480
cataatggca aagaaaacac tgc                                            503
```

<210> SEQ ID NO 65
<211> LENGTH: 501
<212> TYPE: DNA
<213> ORGANISM: Homo sapiens

<400> SEQUENCE: 65

```
cttcattcaa cacacactcc ttgagcatcc actatgtacc aggcatcatg gagggaactt     60
agcatgtggc atacataaaa cgcaaatggt ccttgccttc aagttcatac ttgagtgagc    120
acgcagacaa taataagtga agaaataatt acagcaagta attacaaata atgatcaaag    180
taatgcaaga aagcaagatg acatgtctga ctttgttgct agtttgtcat ttgaatatat    240
aatgggacaa agggcttcta taattaattc tcctataata tataggag   aattatatat    300 gatacataat tcagggctcc tatagtgtaa tcaattctca atattataaa atgaggattt    360
cctgattcaa cttgcaaaaa catgtgaaag taatgagaaa tactgttttc tcttgctgtt    420
cacattcagt ttcctggaaa gccactttg  agagttgtgt ttgctttcaa gaggcctggc    480
ttagagatcc agagggattc c                                              501
```

<210> SEQ ID NO 66
<211> LENGTH: 506
<212> TYPE: DNA
<213> ORGANISM: Homo sapiens

<400> SEQUENCE: 66

```
cttcattcaa cacacactcc ttgagcatcc actatgtacc aggcatcatg gagggaactt     60
agcatgtggc atacataaaa cgcaaatggt ccttgccttc aagttcatac ttgagtgagc    120
acgcagacaa taataagtga agaaataatt acagcaagta attacaaata atgatcaaag    180
taatgcaaga aagcaagatg acatgtctga ctttgttgct agtttgtcat ttgaatatat    240
aatgggacaa ctttcagggc ttctataatt aattctccta atatatat   aggagaatta    300 tatatgatac ataattcagg ctcctatag  tgtaatcaat tctcaatatt ataaaatgag    360
gatttcctga ttcaacttgc aaaaacatgt gaaagtaatg agaaatactg ttttctcttg    420
ctgttcacat tcagtttcct ggaaagccac ttttgagagt tgtgtttgct ttcaagaggc    480
ctggcttaga gatccagagg gattcc                                         506
```

<210> SEQ ID NO 67
<211> LENGTH: 505
<212> TYPE: DNA
<213> ORGANISM: Homo sapiens

<400> SEQUENCE: 67

```
agtcctcacc cttgaattaa ttagtagttt gtaattttgt tttcaatttt gtttgatatt     60
acagatatcg tgccaatact ggttttaat  ttaggtccat tgttgttaga caactttatg    120
```

```
tgacttgaat ccctttaaat ttattgggac ttgtattatg gcactgaatg taaccgttgt    180
tcaatgtttt gtatgcactt gaaagaatta ttcatttgct attttttgggt gttattagat    240 gtttgggtat ttttaggaat taattagatc aggttggttg gtggtgttaa gttttctata    300
ttcttgctta ttttctgtct acttctttta aaagtgactg ataatgtatt aaaatcaaga    360
actgtaattc tatatttgtc ttacttctcc ttgaagtaat atcagacatt acttcatgta    420
ttttgagtct ttgttaatta ggtgtaaaac attaagcttt gacatgctct cttgatgagc    480
tgacctcttt ttcactatga aatga                                          505
```

```
<210> SEQ ID NO 68
<211> LENGTH: 509
<212> TYPE: DNA
<213> ORGANISM: Homo sapiens

<400> SEQUENCE: 68
agtcctcacc cttgaattaa ttagtagttt gtaattttgt tttcaatttt gtttgatatt    60
acagatatcg tgccaatact ggttttaat ttaggtccat tgttgttaga caactttatg    120
tgacttgaat ccctttaaat ttattgggac ttgtattatg gcactgaatg taaccgttgt    180
tcaatgtttt gtatgcactt gaaagaatta ttcatttgct attttttgggt gttattagat    240 gtttgggtat taattttag gaattaatta gatcaggttg gttggtggtg ttaagttttc    300
tatattcttg cttattttct gtctacttct tttaaaagtg actgataatg tattaaaatc    360
aagaactgta attctatatt tgtcttactt ctccttgaag taatatcaga cattacttca    420 tgtatttga gtctttgtta attaggtgta aacattaag ctttgacatg ctctcttgat    480
gagctgacct cttttcact atgaaatga                                       509
```

```
<210> SEQ ID NO 69
<211> LENGTH: 501
<212> TYPE: DNA
<213> ORGANISM: Homo sapiens

<400> SEQUENCE: 69
atccctctag gagatacttc ctttaacata tcaaatgttc aaatatgatc ctcctgtgag    60
tgatccttct tgctgaccta agttcattat ttgtccatgc tcagtatctt aaatagaata    120
ttgcttggtt ttcattctgt tttcagtttt gagaaagttc acataatatt aaatcatcac    180
taatttaggc acaaacctga tcttctttta tgttccattt taatcctaat attatgctag    240
tatctctgtc cagttaaacc taaacctaat tgtgatgaat tttgcctgta attcacacat    300
tccccacatg aaatcccctt gtgatgaagg ataggatatg atcaatatcc atatatcata    360
catatcaaga tcaaacccat gttcatcaca tttcagaatt ttaaagtggc acctctcatt    420
atttgaatga attcaataat atttctatat tcatatagag atagatttca aaagtagata    480
ggaaacacac gtgggccacc t                                              501
```

```
<210> SEQ ID NO 70
<211> LENGTH: 505
<212> TYPE: DNA
<213> ORGANISM: Homo sapiens

<400> SEQUENCE: 70
atccctctag gagatacttc ctttaacata tcaaatgttc aaatatgatc ctcctgtgag    60
tgatccttct tgctgaccta agttcattat ttgtccatgc tcagtatctt aaatagaata    120
ttgcttggtt ttcattctgt tttcagtttt gagaaagttc acataatatt aaatcatcac    180
```

```
taatttaggc acaaacctga tcttcttttta tgttccattt taatcctaat attatgctag    240
tatctctgtc cagtcagtta aacctaaacc taattgtgat gaattttgcc tgtaattcac    300
acattcccca catgaaatcc ccttgtgatg aaggatagga tatgatcaat atccatatat    360
catacatatc aagatcaaac ccatgttcat cacatttcag aattttaaag tggcacctct    420
cattatttga atgaattcaa taatatttct atattcatat agagatagat ttcaaaagta    480
gataggaaac acacgtgggc cacct                                         505

<210> SEQ ID NO 71
<211> LENGTH: 501
<212> TYPE: DNA
<213> ORGANISM: Homo sapiens

<400> SEQUENCE: 71
tccagtccag ccagttgctg agatggggag caacgcaagg gaagcagcag ggttgtaccg     60
aatgaggttt ctctgtgttt tccacatttc cttgcttccc ggtcaaaggg gggcagccct    120
tccttatttt atgcctttct actcgtagcc tcattgcttc ctcctgattc ggatagtact    180
tttcacataa tgcaagaaaa acgaacaaaa agccaaacaa taaacccaaa ctgttgcatt    240
ttggcacaag tgtaatcata ataactagag atttcttggc tttggattgg aaggagggaa    300
gtcactctag agcaggttgg aatagaaaat actgataatt ggatataaaa ataaagaatg    360
gtctcattac atttttaaca gtggtattta ggattgactc aaagaagaaa gcttcctcta    420
ctttaagttc cttgccttgg atatctcaaa attacaaagg tttcctggca gaagtttgcc    480
acattttgca gggaatttat a                                             501

<210> SEQ ID NO 72
<211> LENGTH: 508
<212> TYPE: DNA
<213> ORGANISM: Homo sapiens

<400> SEQUENCE: 72
tccagtccag ccagttgctg agatggggag caacgcaagg gaagcagcag ggttgtaccg     60
aatgaggttt ctctgtgttt tccacatttc cttgcttccc ggtcaaaggg gggcagccct    120
tccttatttt atgcctttct actcgtagcc tcattgcttc ctcctgattc ggatagtact    180
tttcacataa tgcaagaaaa acgaacaaaa agccaaacaa taaacccaaa ctgttgcatt    240
ttggcacaag gaattagtgt aatcataata actagagatt tcttggcttt ggattggaag    300
gagggaagtc actctagagc aggttggaat agaaaatact gataattgga tataaaaata    360
aagaatggtc tcattacatt tttaacagtg gtatttagga ttgactcaaa gaagaaagct    420
tcctctactt taagttcctt gccttggata tctcaaaatt acaaaggttt cctggcagaa    480
gtttgccaca ttttgcaggg aatttata                                      508

<210> SEQ ID NO 73
<211> LENGTH: 505
<212> TYPE: DNA
<213> ORGANISM: Homo sapiens

<400> SEQUENCE: 73
tttctgtaga gatgcagttt ttgcgtgttg tccaggctga tctcagattc ctagactcaa     60
accttcttcc tgtgatggcc tcccaaagtg ctgggattac aggtgtgagc catcacacac    120
agcccattga tttagataaa aaccaatacg acatttattc ccaaaagccc attcctaagc    180
```

```
ttcccaattt ccattagtat aaaacttgcc ttctatagag agcatggcct cttgttcttt    240
atcttgagta ttatttctat atcaaagaaa aaatgagatg gagaaagtct agtatcataa    300
gaactactaa ttcattatat tgaggcctat actggaccta tttaggggat aatattaagt    360
aatttaaata atattctgta tagtttccac taccttgtca tattttagtg tcttatttct    420
ctgtttgttt ttccagactc tgacaataaa ggtgtgaatt ctggaagatt ggtagcttgc    480
ataaccactt tgttcttatt cagca                                          505

<210> SEQ ID NO 74
<211> LENGTH: 509
<212> TYPE: DNA
<213> ORGANISM: Homo sapiens

<400> SEQUENCE: 74
tttctgtaga gatgcagttt ttgcgtgttg tccaggctga tctcagattc ctagactcaa     60
accttcttcc tgtgatggcc tcccaaagtg ctgggattac aggtgtgagc catcacacac    120
agcccattga ttttagataa aaccaatacg acatttattc ccaaaagccc attcctaagc    180
ttcccaattt ccattagtat aaaacttgcc ttctatagag agcatggcct cttgttcttt    240
atcttgagta tatgatattt ctatatcaaa gaaaaaatga gatggagaaa gtctagtatc    300
ataagaacta ctaattcatt atattgaggc ctatactgga cctatttagg ggataatatt    360
aagtaattta ataatattc tgtatagttt ccactacctt gtcatatttt agtgtcttat    420
ttctctgttt gttttttccag actctgacaa taaaggtgtg aattctggaa gattggtagc    480
ttgcataacc actttgttct tattcagca                                      509

<210> SEQ ID NO 75
<211> LENGTH: 510
<212> TYPE: DNA
<213> ORGANISM: Homo sapiens

<400> SEQUENCE: 75
tttactgtga tttaagattt tggttactcc ataattgaag cccttggaca agtatgttt     60 actgtgattt aagattttgg ttattcagtc taaactattt aaaattttga ctagcagttt    120
caggggccag tgttactact aaatttggtt aactcacttt taccagagta ccaaaaaaga    180
aaatagctac ttttttacat atgtgtttat agttttgaaa gtgaattgat cactttgttt    240
cttgctctga atcttaattt ttttttcctaa aggaaaaaga taatttactt tttatagagc    300 aaaaattcata agattcttag aaactcctga gaatctgagc taatggcatg ttctaggtta    360
gttgatatat aaactaaatc atacaggaaa ttgtaaaata gatactttgg ttgcatgtaa    420
tttcctagct cttccttacc tgcatactcc ccctccaatg tagttcacca agatatatac    480
tctttcaaat aatttcataa aaagatttta                                    510

<210> SEQ ID NO 76
<211> LENGTH: 515
<212> TYPE: DNA
<213> ORGANISM: Homo sapiens

<400> SEQUENCE: 76
tttactgtga tttaagattt tggttactcc ataattgaag cccttggaca agtatgttt     60 actgtgattt aagattttgg ttattcagtc taaactattt aaaattttga ctagcagttt    120
caggggccag tgttactact aaatttggtt aactcacttt taccagagta ccaaaaaaga    180
aaatagctac ttttttacat atgtgtttat agttttgaaa gtgaattgat cactttgttt    240
```

```
cttgctctga atcttttgta aattttttt  cctaaaggaa aaagataatt tactttttat    300
agagcaaaat tcataagatt cttagaaact cctgagaatc tgagctaatg gcatgttcta    360
ggttagttga tatataaact aaatcataca ggaaattgta aaatagatac tttggttgca    420
tgtaatttcc tagctcttcc ttacctgcat actccccctc caatgtagtt caccaagata    480
tatactcttt caaataattt cataaaaaga tttta                                515

<210> SEQ ID NO 77
<211> LENGTH: 505
<212> TYPE: DNA
<213> ORGANISM: Homo sapiens

<400> SEQUENCE: 77
aaacccagag tcagaatagt acctgatata tgataggcat taaattatgg tagttggtaa     60
agctggctaa tggaaatttt cctatggagg aggatagagg aatagcagcc tctctcttat    120
aaactgagtc atggcactct tctagcaagt attttttgctg gcctgtttat cttctaaagg    180
gatgtgctga aaaaaaatgg gtcatttagg gattagagta atgtaagtaa tctgatgaaa    240
tttaccactt ctagttattt ccttgtttat gaactacaga atccgattac cctgaaattc    300
ttcttatatt ctaaaagctg tctctaatgt tgcacatcag cttccagggc cagcttctag    360
gttagctgat gcagtcacca gagctagata ccaggaatta ttagcaagc ttcatttcaa     420 gctctgcctc tactgtttaa agtaatctct gtggcttctg gcaagaccac agatctctct    480
gagactcagt ttttttaatc tgtta                                         505

<210> SEQ ID NO 78
<211> LENGTH: 509
<212> TYPE: DNA
<213> ORGANISM: Homo sapiens

<400> SEQUENCE: 78
aaacccagag tcagaatagt acctgatata tgataggcat taaattatgg tagttggtaa     60
agctggctaa tggaaatttt cctatggagg aggatagagg aatagcagcc tctctcttat    120
aaactgagtc atggcactct tctagcaagt attttttgctg gcctgtttat cttctaaagg    180
gatgtgctga aaaaaaatgg gtcatttagg gattagagta atgtaagtaa tctgatgaaa    240
tttaccactt ctagttagtt atttccttgt ttatgaacta cagaatccga ttaccctgaa    300
attcttctta tattctaaaa gctgtctcta atgttgcaca tcagcttcca gggccagctt    360
ctaggttagc tgatgcagtc accagagcta gataccagga attaattagc aagcttcatt    420
tcaagctctg cctctactgt ttaaagtaat ctctgtggct tctggcaaga ccacagatct    480
ctctgagact cagttttttt aatctgtta                                      509

<210> SEQ ID NO 79
<211> LENGTH: 502
<212> TYPE: DNA
<213> ORGANISM: Homo sapiens

<400> SEQUENCE: 79
gccaccatgc ccagctaatt tttgtatttt taataaagat ggggtttcac taggttgggc     60
aggctggtct tgaacgcctg acctcagatg atccacctgc ctcggcctcc caaagtgctg    120
ggattacagg cgtgagccac cacgtctggc tgaaacctgt cactcttaca catcagagaa    180
atcctaaacc ccatgtgaat agtgtggttg gccataattt atatgcctta tatcaaatgt    240
```

```
cottatgaat ttacataaaa tttattcttt catttttata gtctgttcgg cacttgaagt    300
actccttgtt taagaaatca ctactgggca gtgtttcgga taatggaata gtaactctct    360
gggatgtaaa tagtcagagt ccataccata actttgacag tgtacacaaa gctccagcgt    420
caggcatctg ttttctcct gtcaatgaat tgctctttgt aaccataggc ttggataaaa     480
gaatcatcct ctatgacact tc                                             502
```

<210> SEQ ID NO 80
<211> LENGTH: 510
<212> TYPE: DNA
<213> ORGANISM: Homo sapiens

<400> SEQUENCE: 80

```
gccaccatgc ccagctaatt tttgtatttt taataaagat ggggtttcac taggttgggc     60
aggctggtct tgaacgcctg acctcagatg atccacctgc ctcggcctcc caaagtgctg    120
ggattacagg cgtgagccac cacgtctggc tgaaacctgt cactcttaca catcagagaa    180
atcctaaacc ccatgtgaat agtgtggttg gccataattt atatggctta tatcaaatgt    240
ccttatgaat gcttataatt acataaaatt tattctttca tttttatagt ctgttcggca    300
cttgaagtac tccttgttta agaaatcact actgggcagt gtttcggata atggaatagt    360
aactctctgg gatgtaaata gtcagagtcc ataccataac tttgacagtg tacacaaagc    420
tccagcgtca ggcatctgtt tttctcctgt caatgaattg ctctttgtaa ccataggctt    480
ggataaaaga atcatcctct atgacacttc                                     510
```

<210> SEQ ID NO 81
<211> LENGTH: 501
<212> TYPE: DNA
<213> ORGANISM: Homo sapiens

<400> SEQUENCE: 81

```
agcagctaaa gtatttaaga cgttagttaa tctagagagc tacagatggg ggaaagggcc     60
tttgcctttc tgggcccgtt tcttcttgtt ctctcggata cttctagttg aagattctgc    120
tgctgtgagt ccgagtttct gtgcatccag aaggcagagg gggtgggtgc gtatgcacag    180
atcatggact catcaagtct ttccaccaag catcttcgtg aggaggatat ccttaagctc    240
cagggaggga agggtacctg aaggctgagc cgtttaaggc cagctgcttc tgctgagtgt    300
ggagcaaggc tgtctctcag tctgtttagc ctctgaaagg ggacccagct gtgctgtggc    360
aggttcaggt caaacacatt cttttcatct cagcacccct gcagaggtag ggcacaaggg    420
gagtcaaaac ctctgcaatt tgttcaagtc aagcaacaat tcacgttggg caattgtggg    480
ataaatgaat tcatatcatt t                                              501
```

<210> SEQ ID NO 82
<211> LENGTH: 503
<212> TYPE: DNA
<213> ORGANISM: Homo sapiens

<400> SEQUENCE: 82

```
agcagctaaa gtatttaaga cgttagttaa tctagagagc tacagatggg ggaaagggcc     60
tttgcctttc tgggcccgtt tcttcttgtt ctctcggata cttctagttg aagattctgc    120
tgctgtgagt ccgagtttct gtgcatccag aaggcagagg gggtgggtgc gtatgcacag    180
atcatggact catcaagtct ttccaccaag catcttcgtg aggaggatat ccttaagctc    240
cagggaggga aggggtacc tgaaggctga gccgtttaag gccagctgct tctgctgagt    300
```
gtggagcaag gctgtctctc agtctgttta gcctctgaaa ggggacccag ctgtgctgtg    360
gcaggttcag gtcaaacaca ttcttttcat ctcagcaccc ctgcagaggt agggcacaag    420
gggagtcaaa acctctgcaa tttgttcaag tcaagcaaca attcacgttg gcaattgtg    480 ggataaatga attcatatca ttt                                            503

<210> SEQ ID NO 83
<211> LENGTH: 501
<212> TYPE: DNA
<213> ORGANISM: Homo sapiens

<400> SEQUENCE: 83
atataattat tgttgctatt ttaattttca atgaaaacaa taatacatgt taatagtggc     60
atatctggaa aatacaaaag tataaagaaa gatctatttc tttatacaga tattttatgt    120
atacataatt tccctactag gctcatatta tacagcagtt gtatatcctg ttcttttga    180 atttcaattt tatctccaat ttcgtaatac tacaaataac acaatcaaat gttctcactt    240
ctaaattttg ttttttttatt actacataat ccttgggaca tatttcaaaa agtgttcata    300
tttagtcaaa gggcattgac aactttttaa actcttgctg agtgtttcaa aattgcttgc    360
tgcaaagttt gcatcatcaa cattttcttc tggtagtgat ttgtaaatgc tggtttcatc    420
catgtctgac tgggctcctc ctctgctttc tgctccccaa actcctgcat atatgtatga    480
gacttatctt ttgccacttt c                                              501

<210> SEQ ID NO 84
<211> LENGTH: 503
<212> TYPE: DNA
<213> ORGANISM: Homo sapiens

<400> SEQUENCE: 84
atataattat tgttgctatt ttaattttca atgaaaacaa taatacatgt taatagtggc     60
atatctggaa aatacaaaag tataaagaaa gatctatttc tttatacaga tattttatgt    120
atacataatt tccctactag gctcatatta tacagcagtt gtatatcctg ttcttttga    180 atttcaattt tatctccaat ttcgtaatac tacaaataac acaatcaaat gttctcactt    240
ctaaattttg ttcttttta ttactacata atccttggga catatttcaa aaagtgttca    300
tatttagtca aagggcattg acaacttttt aaactcttgc tgagtgtttc aaaattgctt    360
gctgcaaagt ttgcatcatc aacatttcct ctggtagtg atttgtaaat gctggtttca    420
tccatgtctg actgggctcc tcctctgctt tctgctcccc aaactcctgc atatatgtat    480
gagacttatc ttttgccact ttc                                            503

<210> SEQ ID NO 85
<211> LENGTH: 501
<212> TYPE: DNA
<213> ORGANISM: Homo sapiens

<400> SEQUENCE: 85
tctagctata agaaggaagt gatcaacagg ctctgaatta acttttccca ttcctgggag     60
aatatccacg gtcttgcttc gtgtggcatt aatcggcaaa tatttatcat tgcctatgtt    120
tgccaagcag ttttctagaa actgatccct tgaaaacata tctcttgagg aatatatcat    180
tctttaaaaa agtggctaag ttactatgtc tgtgaactca gtccagaaag gcccttacaa    240
gagaaaagag agttgtgagc tgacagactt aatgaaatgt gcttaacgta taagtaaatt    300

```
tgtctctgtt tttactcata aaattatcta taaatttcct tatatgttcc tttttacatt     360
ttatgatttt gtgttggttt ttaaaatata tattatttaa ttagaattat tttagtatgg     420
aattccaggt ataaatataa gattattttc gcaatactta accaattatt cctgtgccag     480
ctatcaaata acccacactt t                                               501

<210> SEQ ID NO 86
<211> LENGTH: 504
<212> TYPE: DNA
<213> ORGANISM: Homo sapiens

<400> SEQUENCE: 86
tctagctata agaaggaagt gatcaacagg ctctgaatta acttttccca ttcctgggag     60
aatatccacg gtcttgcttc gtgtggcatt aatcggcaaa tatttatcat tgcctatgtt    120
tgccaagcag ttttctagaa actgatccct tgaaaacata tctcttgagg aatatatcat    180
tctttaaaaa agtggctaag ttactatgtc tgtgaactca gtccagaaag gcccttacaa    240
gagaaaagag agttgttgtg agctgacaga cttaatgaaa tgtgcttaac gtataagtaa    300
atttgtctct gttttttactc ataaaattat ctataaattt ccttatatgt tccttttttac   360 attttatgat tttgtgttgg tttttaaaat atatattatt taattagaat tattttagta    420
tggaattcca ggtataaata taagattatt ttcgcaatac ttaaccaatt attcctgtgc    480
cagctatcaa ataacccaca cttt                                           504

<210> SEQ ID NO 87
<211> LENGTH: 501
<212> TYPE: DNA
<213> ORGANISM: Homo sapiens

<400> SEQUENCE: 87
cagcgatcgc agtagctttg ttctcataga atccccggtg cctagcacag gccttggccc    60
atagtagctg cacagataaa tatttgttgc ttgaatgtct gtaggattct caatctagtc    120
aacttgtata ggctgttgtc ttagacctgg aaccagacca aagcaagctg gcccaacctt    180
ggttgtgtcc taatttggcc atctgactat gaatatgcta acaaatgaca ggcttagcct    240
ccagcatttc cattccttcc ctggagcaag ctcccccacc agcaatcttc ccagccctaa    300
ggcaggtctg tgttgatggg gctagaggcc agaggactgg ttgatctgat cactcaattc    360
cttctgccta acttcagaag cttcttccaa aataagagac cttttttttt ggattttttt    420 tttttttaaga tggagtctta ttctgtcgcc caggctggag tatagtggca cgatctccgc    480
tcactgcaac ttttgcctcc t                                              501

<210> SEQ ID NO 88
<211> LENGTH: 504
<212> TYPE: DNA
<213> ORGANISM: Homo sapiens

<400> SEQUENCE: 88
cagcgatcgc agtagctttg ttctcataga atccccggtg cctagcacag gccttggccc    60
atagtagctg cacagataaa tatttgttgc ttgaatgtct gtaggattct caatctagtc    120
aacttgtata ggctgttgtc ttagacctgg aaccagacca aagcaagctg gcccaacctt    180
ggttgtgtcc taatttggcc atctgactat gaatatgcta acaaatgaca ggcttagcct    240
ccagcatttc ttccattcct tccctggagc aagctccccc accagcaatc ttcccagccc    300
taaggcaggt ctgtgttgat ggggctagag gccagaggac tggttgatct gatcactcaa    360
```

| | |
|---|---|
| ttccttctgc ctaacttcag aagcttcttc caaaataaga gacctttttt tttggatttt | 420 |
| ttttttttta agatggagtc ttattctgtc gcccaggctg gagtatagtg gcacgatctc | 480 |
| cgctcactgc aactttttgcc tcct | 504 |

<210> SEQ ID NO 89
<211> LENGTH: 501
<212> TYPE: DNA
<213> ORGANISM: Homo sapiens

<400> SEQUENCE: 89

| | |
|---|---|
| gaattcatca gcctggtgga aaagtactgg catatggatt aggtttgagt aagctcatta | 60 |
| gaggggcatt attctactga aattatagca ttagatttgt agaatgactt ctattcagcc | 120 |
| aacaagttgg tactccatat ttaatgatca taaatctttg tgtaagctct gcaatttgtg | 180 |
| aaatttcatt agctcattat cctttgtgct tgttgccaaa tactgtcaat gctactttaa | 240 |
| aaacttctcc attccagaac ttacagcccc ggtagtctg gcttggtatt cctgcagcaa | 300 |
| atccatgctc ctaattccat gattcaccct tcaaaccctg ccaccttcat caattctatc | 360 |
| cttaacagta aacactagat atcttatact cattccattc tgctggaact ccacttctta | 420 |
| gaggctatca tgactggtga cttgaagtcc tgtttgtggc cccttaatta cactgatttc | 480 |
| ctaggatggc cacctcttga t | 501 |

<210> SEQ ID NO 90
<211> LENGTH: 504
<212> TYPE: DNA
<213> ORGANISM: Homo sapiens

<400> SEQUENCE: 90

| | |
|---|---|
| gaattcatca gcctggtgga aaagtactgg catatggatt aggtttgagt aagctcatta | 60 |
| gaggggcatt attctactga aattatagca ttagatttgt agaatgactt ctattcagcc | 120 |
| aacaagttgg tactccatat ttaatgatca taaatctttg tgtaagctct gcaatttgtg | 180 |
| aaatttcatt agctcattat cctttgtgct tgttgccaaa tactgtcaat gctactttaa | 240 |
| aaacttctcc ttcattccag aacttacagc cctggtagtt ctggcttggt attcctgcag | 300 |
| caaatccatg ctcctaattc catgattcac ccttcaaacc ctgccacctt catcaattct | 360 |
| atccttaaca gtaaacacta gatatcttat actcattcca ttctgctgga actccacttc | 420 |
| ttagaggcta tcatgactgg tgacttgaag tcctgtttgt ggccccttaa ttacactgat | 480 |
| ttcctaggat ggccacctct tgat | 504 |

<210> SEQ ID NO 91
<211> LENGTH: 501
<212> TYPE: DNA
<213> ORGANISM: Homo sapiens

<400> SEQUENCE: 91

| | |
|---|---|
| gaatagtgcc acaataaaca tacgtgtgca tgcatgtgtc tttatagcag catgatttag | 60 |
| aatccaaaca ttcttataga caagggctcc ttctcctgac gtttctgatc tcattctaaa | 120 |
| acattcaccc agtccactga cctgtactgg gcgctgtgct gggtgccagg cactgctttt | 180 |
| ccatattctt ttctaaactg ctaaaatggg tgattattcc tccaggctct tgctgacac | 240 |
| tgggggaaa ttcttggttt tcacacccct cttaggacgt gtcttccact ctggctttac | 300 |
| ttgttcatag attcatgaaa tcctcaacag agatccttgc aagtgctgag gagatagtgg | 360 |

```
tgaacaaaat agataagatt tctgcttttg taaagtttac attcttctag ggatcgtgtg      420
tccttgattt ggaatgcctg cttagggggg tcatgagggt ataaccctgg tttcctagtt      480
tccagggaat gggttgggtc a                                                501
```

<210> SEQ ID NO 92
<211> LENGTH: 504
<212> TYPE: DNA
<213> ORGANISM: Homo sapiens

<400> SEQUENCE: 92

```
gaatagtgcc acaataaaca tacgtgtgca tgcatgtgtc tttatagcag catgatttag       60
aatccaaaca ttcttataga caagggctcc ttctcctgac gtttctgatc tcattctaaa      120
acattcaccc agtccactga cctgtactgg gcgctgtgct gggtgccagg cactgctttt      180
ccatattctt ttctaaactg ctaaaatggg tgattattcc tccaggctct ttgctgacac      240 tgggggaaa ttcttcttgg ttttcacacc cctcttagga cgtgtcttcc actctggctt      300
tacttgttca tagattcatg aaatcctcaa cagagatcct gcaagtgct gaggagatag       360 tggtgaacaa aatagataag attctgctt ttgtaaagtt tacattcttc tagggatcgt      420
gtgtccttga tttggaatgc ctgcttaggg gggtcatgag ggtataaccc tggtttccta      480
gtttccaggg aatgggttgg gtca                                             504
```

<210> SEQ ID NO 93
<211> LENGTH: 501
<212> TYPE: DNA
<213> ORGANISM: Homo sapiens

<400> SEQUENCE: 93

```
gaaggtacat ggtcacagtc caaaatgttt tatacagctc tcagcctgga aaatgcaact       60
gatgaaaaag gcactgtttc tagaacaaat ggaaaaagaa taaatatgtc atcatttacc      120
ctgcacagct ttgagtaaca ccataggacc ctgtcacacg ttcagggtca atttaaaag      180 cttgagaaga cacagcaagg tgatgtccta gactagccag gctccgaaag gaagagctgt      240
ctgtccctcc taactgtcct ctctctgtca caggtgtcca tgtcactgtt cctctagcag      300
atgtggaaag tggctgctca gtgaggactc agcccccacc aacctgactg agggtcacac      360
gacaccatgg tggaaagtca caagggtaa cgggccaaga gggtgagggg gctccctga      420 cccctgaggac ccctgaggca ctgctgcacc ttccacggat tctgtgtcta gcgttgccct      480
ctttgcagat gccctcgtg g                                                 501
```

<210> SEQ ID NO 94
<211> LENGTH: 505
<212> TYPE: DNA
<213> ORGANISM: Homo sapiens

<400> SEQUENCE: 94

```
gaaggtacat ggtcacagtc caaaatgttt tatacagctc tcagcctgga aaatgcaact       60
gatgaaaaag gcactgtttc tagaacaaat ggaaaaagaa taaatatgtc atcatttacc      120
ctgcacagct ttgagtaaca ccataggacc ctgtcacacg ttcagggtca atttaaaag      180 cttgagaaga cacagcaagg tgatgtccta gactagccag gctccgaaag gaagagctgt      240
ctgtccctcc tcactaactg tcctctctct gtcacaggtg tccatgtcac tgttcctcta      300
gcagatgtgg aaagtggctg ctcagtgagg actcagcccc caccaacctg actgagggtc      360
acacgacacc atggtggaaa gtcacaaagg gtaacgggcc aagagggtga gggggctcc      420
```

```
ctgaccctga ggaccsctga ggcactgctg caccttccac ggattctgtg tctagcgttg    480
ccctctttgc agatgcccct cgtgg                                          505

<210> SEQ ID NO 95
<211> LENGTH: 501
<212> TYPE: DNA
<213> ORGANISM: Homo sapiens

<400> SEQUENCE: 95
caccatctgg aaacaaacta tcatagttca gcgggcaatt ataaaacaaa cattttagtc    60
tgctggccag atcttttta agttgaatac cgaaaaaaaa aatagtgctc cacttcactt   120
agaagtagtt gcaggctgat gagtttggtt tttgttaaca agaacaaga gctagacttt   180 gtcaggaggc agccacctaa ataatgtaat aaatactctt tatagcctag aagaatttgt   240
aaacatttta ctaagttgct aatgaaggtt ttaaacttac aagaacttg atgttgttgt   300 agtatgttat gtcttactgt gtaatgtgtc ttaagataaa acagccttta tataatta    360 ccaaacataa gtgaaattct ttcagatgct taagacttt aaatattaca ttctggtgtt   420
acataatgtc atatcctcct attctacaaa atgacctctc ctctctgtaa aaggtcattc   480
ttgttattaa ttgatgtggt g                                            501

<210> SEQ ID NO 96
<211> LENGTH: 505
<212> TYPE: DNA
<213> ORGANISM: Homo sapiens

<400> SEQUENCE: 96
caccatctgg aaacaaacta tcatagttca gcgggcaatt ataaaacaaa cattttagtc    60
tgctggccag atcttttta agttgaatac cgaaaaaaaa aatagtgctc cacttcactt   120
agaagtagtt gcaggctgat gagtttggtt tttgttaaca agaacaaga gctagacttt   180 gtcaggaggc agccacctaa ataatgtaat aaatactctt tatagcctag aagaatttgt   240
aaacatttta cttattaagt tgctaatgaa ggttttaaac ttacaagaaa cttgatgttg   300
ttgtagtatg ttatgtctta ctgtgtaatg tgtcttaaga taaaacagcc tttatatata   360
attaccaaac ataagtgaaa ttctttcaga tgcttaagac ttttaaatat tacattctgg   420
tgttacataa tgtcatatcc tcctattcta caaaatgacc tctcctctct gtaaaaggtc   480
attcttgtta ttaattgatg tggtg                                        505

<210> SEQ ID NO 97
<211> LENGTH: 501
<212> TYPE: DNA
<213> ORGANISM: Homo sapiens

<400> SEQUENCE: 97
caaagaactg tgttgtgaaa aaagttattc tatccctact cattcatttc ttctgtaaat    60
caggatttta ggtattttttt tccttaaagc tagttatatc tacgtagaag atttctgcat   120
acttctcttt tttgtttgtt tgttttttga agaacaaagt atataaatgc cctctagagt   180
catagacaca gattgaaggt ggcaaggtga gcaaaattgg cattttgtcc cattacccca   240
ttttcctttt tcttttttttt atcctaagca ggagagaagt gatctgcaag tttctcagga   300
tgcttttggg taagagtttc accataaaaa tgtcttcacc cacactcctc ccagtgtcag   360
tgtgccaggt accctgtcac ctttggttga tgtcctgatg gattaagctc tggacagagc   420
```

```
cacacctttg aagaggcttc ttggccagat taacacacca aggaaagtgc ttcagtctag    480
aacatgcccc gtcgctgggg t                                              501

<210> SEQ ID NO 98
<211> LENGTH: 505
<212> TYPE: DNA
<213> ORGANISM: Homo sapiens

<400> SEQUENCE: 98
caaagaactg tgttgtgaaa aaagttattc tatccctact cattcatttc ttctgtaaat     60
caggatttta ggtatttttt tccttaaagc tagttatatc tacgtagaag atttctgcat    120
acttctcttt tttgtttgtt ttgttttttga agaacaaagt atataaatgc cctctagagt    180
catagacaca gattgaaggt ggcaaggtga gcaaaattgg cattttgtcc cattacccca    240
ttttcctttt cttttctttt tttatcccta agcaggagag aagtgatctg caagtttctc    300
aggatgcttt tgggtaagag tttcaccata aaaatgtctt cacccacact cctcccagtg    360
tcagtgtgcc aggtaccctg tcacctttgg ttgatgtcct gatggattaa gctctggaca    420
gagccacacc tttgaagagg cttcttggcc agattaacac accaaggaaa gtgcttcagt    480
ctagaacatg ccccgtcgct ggggt                                           505

<210> SEQ ID NO 99
<211> LENGTH: 501
<212> TYPE: DNA
<213> ORGANISM: Homo sapiens

<400> SEQUENCE: 99
ggcctccctg ggggtctggc cagaaccagc aatgtgagcc ccaagcacag gcagggtccc     60
tcttgaggtg aaggatttac aactggatta tgaatcttaa ggtgttgctt agaaagtgct    120
gcattatatt atttgtgaac ttaatcataa aaatgtatgt ggaaaaaaat gtatgtgggg    180
tgttttgcat cattaaaggg tttgcgttgg gagcgtattc atcaagggtc ccctggcagt    240
gggccacatc ttcccaggga agtgcaaagc cctacaagtg cctccaagct gctgaggagc    300
cgtgctcctc gttcaaaggc acacctactc ccaggtctgc cagtagtccc agcctggcat    360
ccttatgggt ctccctcctt ccctgacatg aaaccagctc cttgtcactc ggagtttggg    420
ggcctgctgc ataatcctca tctccagcca tgtctcctga ccctgtgaca ctcttggttc    480
cacccacaat tccttagggc c                                              501

<210> SEQ ID NO 100
<211> LENGTH: 506
<212> TYPE: DNA
<213> ORGANISM: Homo sapiens

<400> SEQUENCE: 100
ggcctccctg ggggtctggc cagaaccagc aatgtgagcc ccaagcacag gcagggtccc     60
tcttgaggtg aaggatttac aactggatta tgaatcttaa ggtgttgctt agaaagtgct    120
gcattatatt atttgtgaac ttaatcataa aaatgtatgt ggaaaaaaat gtatgtgggg    180
tgttttgcat cattaaaggg tttgcgttgg gagcgtattc atcaagggtc ccctggcagt    240
gggccacatc acatcttccc agggaagtgc aaagccctac aagtgcctcc aagctgctga    300
ggagccgtgc tcctcgttca aaggcacacc tactcccagg tctgccagta gtcccagcct    360
ggcatcctta tgggtctccc tccttccctg acatgaaacc agctccttgt cactcggagt    420
ttgggggcct gctgcataat cctcatctcc agccatgtct cctgaccctg tgacactctt    480
```

```
ggttccaccc acaattcctt agggcc                                          506

<210> SEQ ID NO 101
<211> LENGTH: 501
<212> TYPE: DNA
<213> ORGANISM: Homo sapiens

<400> SEQUENCE: 101
taagaaaaat gatacatctt ccaagttaag tacttcctaa acacacattt aaattaattt     60
ctgcttgaaa cattcacaca ccagatttat ggatcaactg ctctcaacat caacaactag    120
ttgctcaaaa aattttcaaa gtgtgaaacc cttttgttaa aaacaaaagc atcctcaatc    180
tctctaaatt ctgcctttga agctattatt ggatataact gattccaccac attccagatg   240 cacatgtgac cactaacatt tgattatgag ctaattgcta tgtttcctgt tgagcagcag    300
gtgactgaga atcttgacta tacagtttat gatcatcttg ttggctgaaa tgtattcctt   360
tagttggcac aattccattt tccatttctc tctgctgtga tgggggtgtg attttttgaat  420 gtaaatgtga agagtccact gttgaatgat gactaacatc caccttagct aaaatttcat   480
aatacaacaa ataaaacact g                                              501

<210> SEQ ID NO 102
<211> LENGTH: 506
<212> TYPE: DNA
<213> ORGANISM: Homo sapiens

<400> SEQUENCE: 102
taagaaaaat gatacatctt ccaagttaag tacttcctaa acacacattt aaattaattt     60
ctgcttgaaa cattcacaca ccagatttat ggatcaactg ctctcaacat caacaactag    120
ttgctcaaaa aattttcaaa gtgtgaaacc cttttgttaa aaacaaaagc atcctcaatc    180
tctctaaatt ctgcctttga agctattatt ggatataact gattccaccac attccagatg   240 cacatgtgac ctgaccacta acatttgatt atgagctaat tgctatgttt cctgttgagc   300
agcaggtgac tgagaatctt gactatacag tttatgatca tcttgttggc tgaaatgtat   360
tcctttagtt ggcacaattc catttttccat ttctctctgc tgtgatgggg gtgtgatttt  420
tgaatgtaaa tgtgaagagt ccactgttga atgatgacta acatccacct tagctaaaat   480
ttcataatac aacaaataaa acactg                                         506

<210> SEQ ID NO 103
<211> LENGTH: 506
<212> TYPE: DNA
<213> ORGANISM: Homo sapiens

<400> SEQUENCE: 103
taattacaag aacacagaat agttgaaagt aaaggatgga aaaatatacc atgcaaatat     60
taacccttca aaataagctg acacagttac attaatatca atgtatattt taagatgaaa   120
cagttcataa tgataaggag gccaactcaa cagtaatata tcataatctg gaatctatat    180
gtacttgata aaatagcttc aatctatatg tagcaaaaat ggacagaaaa aatagacaaa    240
tacacactca agaaaattcc acacctatct caatagctaa taggacaagc aaccaaaaat   300
cagtgagact aaagatctga gcaacaatta acatatata catatgagac cattgaatct    360
attaggaccg atgacaggta tgttttttca agtgcgcatg ggctatttac caaaattgac   420
cctttgctgg gctctaagct acaatacatt gcaaagatt gaagttattc agagcatacc     480
```

```
ttctagccac agtggaatta aactag                                          506
```

<210> SEQ ID NO 104
<211> LENGTH: 511
<212> TYPE: DNA
<213> ORGANISM: Homo sapiens

<400> SEQUENCE: 104

```
taattacaag aacacagaat agttgaaagt aaaggatgga aaaatatacc atgcaaatat     60
taacccttca aaataagctg acacagttac attaatatca atgtatattt taagatgaaa    120
cagttcataa tgataaggag gccaactcaa cagtaatata tcataatctg gaatctatat    180
gtacttgata aaatagcttc aatctatatg tagcaaaaat ggacagaaaa aatagacaaa    240
tacacactca tagttagaaa attccacacc tatctcaata gctaatagga caagcaacca    300
aaaatcagtg agactaaaga tctgagcaac aattaaacat atatacatat gagaccattg    360
aatctattag gaccgatgac aggtatgttt tttcaagtgc gcatgggcta tttaccaaaa    420
ttgacccttt gctgggctct aagctacaat acattgcaaa agattgaagt tattcagagc    480
ataccttcta gccacagtgg aattaaacta g                                   511
```

<210> SEQ ID NO 105
<211> LENGTH: 501
<212> TYPE: DNA
<213> ORGANISM: Homo sapiens

<400> SEQUENCE: 105

```
ttccaggaat gatgacatct gagttgtgtc tcgaaggagg agtatggaat tcaccaggca     60
gagaaaagga agttcatcac ctgtcttctg atcaggtcac atccccaacc ttccctggct    120
gtcccatcaa attagcttgt ctactgaaag cacactcgtc tgtgggcaga aggcaagcct    180
gcctgcgctt gggcctcaag aaatgttgct tccctatcta cacaacctgg tttgcccacg    240
tgcctcttga taattagaat agaactctag aaggatatta gcatgtcatt tttcaaacct    300
ggtgtaaaag attacagttg gcatacagct cttaaaggtg gcacagaccc aaagagtgag    360
cagcagcagc aaaaaaaaaa aaaaaaaggt tacacttggc agttattttc ttcttgtgct    420
tttctgattt tttttttatt taaacattga acattcactc tttaagcttt ttgtgctttt    480
ctgaattttc tttttatttt a                                              501
```

<210> SEQ ID NO 106
<211> LENGTH: 506
<212> TYPE: DNA
<213> ORGANISM: Homo sapiens

<400> SEQUENCE: 106

```
ttccaggaat gatgacatct gagttgtgtc tcgaaggagg agtatggaat tcaccaggca     60
gagaaaagga agttcatcac ctgtcttctg atcaggtcac atccccaacc ttccctggct    120
gtcccatcaa attagcttgt ctactgaaag cacactcgtc tgtgggcaga aggcaagcct    180
gcctgcgctt gggcctcaag aaatgttgct tccctatcta cacaacctgg tttgcccacg    240
tgcctcttga taagttaatt agaatagaac tctagaagga tattagcatg tcatttttca    300
aacctggtgt aaaagattac agttggcata cagctcttaa aggtggcaca gacccaaaga    360
gtgagcagca gcagcaaaaa aaaaaaaaaa aaggttacac ttggcagtta ttttcttctt    420
gtgcttttct gattttttt ttatttaaac attgaacatt cactctttaa gcttttgtg     480
cttttctgaa ttttcttttt atttaa                                         506
```

<210> SEQ ID NO 107
<211> LENGTH: 501
<212> TYPE: DNA
<213> ORGANISM: Homo sapiens

<400> SEQUENCE: 107

| | | | | | |
|---|---|---|---|---|---|
| gagatgtgta | gttccgccag | gtgtgttgca | cacacatgtc | aagagagcac | ctcctgaacg | 60 |
| cagggacatg | tggcacagct | agggactacg | ttccccgaaa | gccttagcag | cagctcactt | 120 |
| ccacttctgg | gctgaacgtc | ttccctcgca | gtcgcttttg | gtctgctcgg | ccatgtgcag | 180 |
| tgctgagttt | tcgcttcctt | ctgagtggca | cagcgtgggt | acaagcttgg | ctgcgtgcct | 240 |
| ttctccaggt | ttcctgcatg | cagggacaag | tcattctcct | cctgtggctg | ccactagcca | 300 |
| tctgtgtccc | atgcctggga | catcctggac | caggcccctc | ctgccttctg | acctttgcca | 360 |
| gatggcagga | gactgccatc | tcctatcatg | tgacctactg | gacaaagtgc | ggataagttg | 420 |
| aaccatatga | aattgtctaa | gcggggaaac | tccaggtcaa | tgtgtctcct | ttttctgaaa | 480 |
| aaaaaaaaaa | aaaaaaaaaa | a | | | | 501 |

<210> SEQ ID NO 108
<211> LENGTH: 507
<212> TYPE: DNA
<213> ORGANISM: Homo sapiens

<400> SEQUENCE: 108

| | | | | | |
|---|---|---|---|---|---|
| gagatgtgta | gttccgccag | gtgtgttgca | cacacatgtc | aagagagcac | ctcctgaacg | 60 |
| cagggacatg | tggcacagct | agggactacg | ttccccgaaa | gccttagcag | cagctcactt | 120 |
| ccacttctgg | gctgaacgtc | ttccctcgca | gtcgcttttg | gtctgctcgg | ccatgtgcag | 180 |
| tgctgagttt | tcgcttcctt | ctgagtggca | cagcgtgggt | acaagcttgg | ctgcgtgcct | 240 |
| ttctccaggt | ttcctgtcc | tgcatgcagg | gacaagtcat | tctcctcctg | tggctgccac | 300 |
| tagccatctg | tgtcccatgc | ctgggacatc | ctggaccagg | cccctcctgc | cttctgacct | 360 |
| ttgccagatg | gcaggagact | gccatctcct | atcatgtgac | ctactggaca | aagtgcggat | 420 |
| aagttgaacc | atatgaaatt | gtctaagcgg | ggaaactcca | ggtcaatgtg | tctcctttt | 480 |
| ctgaaaaaaa | aaaaaaaaaa | aaaaaaa | | | | 507 |

<210> SEQ ID NO 109
<211> LENGTH: 507
<212> TYPE: DNA
<213> ORGANISM: Homo sapiens

<400> SEQUENCE: 109

| | | | | | |
|---|---|---|---|---|---|
| ggccaagggg | atgtgacatg | ggtcatcaaa | agtgtctgtt | cagggacagc | agatccaaaa | 60 |
| gtcacatgtg | ccaaagaagg | gctcaaatgt | aattctaccc | taaagtcata | cagaataaac | 120 |
| caaatccctc | tcttccacga | aatcttggaa | tatacctgtc | ctatactcta | cagttttaa | 180 |
| gcacactgtg | tcttcacatg | gcatgattat | attctactta | tcaccccagt | ttttttcaca | 240 |
| ttatactgaa | attaaatggc | ataaaaatag | aatacagtac | tctaggaggg | gtcagccaac | 300 |
| caatctgaaa | aagcactatt | gtatagagcg | cttcatggta | ctccagggtt | aggtaaattg | 360 |
| attgttttga | aattcagtga | catagataac | atcatatggc | ttttcatat | tctatttat | 420 |
| tttttgcata | tactcttttt | agttttaca | ttctttaaga | tgactaaaat | atcttcgaat | 480 |
| acaatgctta | acttctagat | atcatct | | | | 507 |

<210> SEQ ID NO 110
<211> LENGTH: 513
<212> TYPE: DNA
<213> ORGANISM: Homo sapiens

<400> SEQUENCE: 110

```
ggccaagggg atgtgacatg ggtcatcaaa agtgtctgtt cagggacagc agatccaaaa      60
gtcacatgtg ccaagaagg gctcaaatgt aattctaccc taaagtcata cagaataaac     120
caaatccctc tcttccacga aatcttggaa tatacctgtc ctatactcta cagttttaa      180
gcacactgtg tcttcacatg gcatgattat attctactta tcaccccagt ttttttcaca    240
ttatactgaa atttgtctta aatggcataa aaatagaata cagtactcta ggaggggtca    300
gccaaccaat ctgaaaaagc actattgtat agagcgcttc atggtactcc agggttaggt    360
aaattgattg ttttgaaatt cagtgacata gataacatca tatggctttt tcatattcta    420
ttttattttt tgcatatact cttttttagtt tttacattct ttaagatgac taaaatatct    480
tcgaatacaa tgcttaactt ctagatatca tct                                 513
```

<210> SEQ ID NO 111
<211> LENGTH: 501
<212> TYPE: DNA
<213> ORGANISM: Homo sapiens

<400> SEQUENCE: 111

```
gcttgaaaag tacttggttt ccaaattaga agaatacttc aaagctaaag tcattaaata     60
tattaatgaa tcatgaaaaa taaatattgg aaaatgtgtt tagtttttaa tgcttgaaaa    120
attttaaagt attacagagt taattataca aagaataat cttgaaaaag gtgagatcag    180
aagttttagg ccatcgtgac aggtcttatt gaaaaaagtt ttgtgaaata ttgattttaa    240
gaaataaaat aatatatctt tgaatataga ataattatga cttatttttct actttactag   300
agtatatttg aaattgaaaa atgcatagta agtattaagg actttata ttgtcagatt     360
taaaaatatt aaaatagaaa taacttgaag cctaagcttt gcaaacaaga gtatctgcta    420
cttattctgc tcagttcctg caccaattca gatcaaggca ggtggtttat ttattaaagt    480
ctggcactaa ttatttgtat a                                              501
```

<210> SEQ ID NO 112
<211> LENGTH: 508
<212> TYPE: DNA
<213> ORGANISM: Homo sapiens

<400> SEQUENCE: 112

```
gcttgaaaag tacttggttt ccaaattaga agaatacttc aaagctaaag tcattaaata     60
tattaatgaa tcatgaaaaa taaatattgg aaaatgtgtt tagtttttaa tgcttgaaaa    120
attttaaagt attacagagt taattataca aagaataat cttgaaaaag gtgagatcag    180
aagttttagg ccatcgtgac aggtcttatt gaaaaaagtt ttgtgaaata ttgattttaa    240
gaaataaaat caatcaaaat atatctttga atatagaata attatgactt attttctact    300
ttactagagt atatttgaaa ttgaaaaatg catagtaagt attaaggata ctttatattg    360
tcagatttaa aaatattaaa atagaaataa cttgaagcct aagctttgca aacaagagta    420
tctgctactt attctgctca gttcctgcac caattcagat caaggcaggt ggtttattta    480
ttaaagtctg gcactaatta tttgtata                                       508
```

```
<210> SEQ ID NO 113
<211> LENGTH: 501
<212> TYPE: DNA
<213> ORGANISM: Homo sapiens

<400> SEQUENCE: 113
gtagctggga ctacaggggc acgccaccat gcctggctaa tttttgcatt tttagtagag      60
atggggtttc accatattgg ccaggctggt ctcaaactcc tgacctcgtg atccgcccgc     120
cttggcctcc caaagtgctg ggattacagg catgagccac cacacccagc tgaatgaaac     180
ttaataggga gttatgagat acagacgttc ctagtaaatt cagagggaga gaaaacaagg     240
gctttgcttt gttctcagtg tagttagtat tagagccacc gttaacagga ctgttttcct     300
attaccttgt ctaatatgca ttgcttcctc tggggaaagt gaaaaactgg aaggatgagg     360
acccaggtga ctaagataag ctggtgatat tgaagggaca aaactttgat ggttggagga     420
acccagcaga gaaagggaaa agataagagc tcttgctaac tcaaaatttt acttggggct     480
gatcctacct gctctcccaa t                                               501

<210> SEQ ID NO 114
<211> LENGTH: 496
<212> TYPE: DNA
<213> ORGANISM: Homo sapiens

<400> SEQUENCE: 114
gtagctggga ctacaggggc acgccaccat gcctggctaa tttttgcatt tttagtagag      60
atggggtttc accatattgg ccaggctggt ctcaaactcc tgacctcgtg atccgcccgc     120
cttggcctcc caaagtgctg ggattacagg catgagccac cacacccagc tgaatgaaac     180
ttaataggga gttatgagat acagacgttc ctagtaaatt cagagggaga gaaaacaagg     240
gctttgttct cagtgtagtt agtattagag ccaccgttaa caggactgtt ttcctattac     300
cttgtctaat atgcattgct tcctctgggg aaagtgaaaa actggaagga tgaggaccca     360
ggtgactaag ataagctggt gatattgaag ggacaaaact ttgatggttg gaggaaccca     420
gcagagaaag ggaaaagata agagctcttg ctaactcaaa attttacttg ggctgatcc     480 tacctgctct cccaat                                                     496

<210> SEQ ID NO 115
<211> LENGTH: 501
<212> TYPE: DNA
<213> ORGANISM: Homo sapiens

<400> SEQUENCE: 115
agcaaggctc atcagtcctc ccaagaccac cagcagagct caagccctgt cacataccc       60 aaaggtcttt cctccccagg cggcacatct ccagccactg ccgacatgtg atgggaagca    120
agtgtcagga atctgaccac ggtcctcag ccagtgctgc ctgattcagg gccccttata     180
tgcaggaatc caggatgtca acacagtcct tcacacacca tatggatcac ttctagcttg    240
gaggaaggaa agagagaagg ttcccatggg cctaaacact gcatatttat gtgcagacac    300
attgcagttg catgttggtg aaaactgagg cccaggtgtc tgcatacaaa cagcaggcct    360
tcctataatt taaagatgtt ggtgaagggt tcagcaagct cagacaatgg aaggatgaaa    420
catggcatgc ggcatgcagt ttgatcaaaa agaaaaacat gtctgccgga cgtggtggct    480
cacgcctgta atcctaacac t                                               501

<210> SEQ ID NO 116
```

<211> LENGTH: 513
<212> TYPE: DNA
<213> ORGANISM: Homo sapiens

<400> SEQUENCE: 116

| | | | | | |
|---|---|---|---|---|---|
| agcaaggctc | atcagtcctc | ccaagaccac | cagcagagct | caagccctgt | cacatacccc | 60 |
| aaaggtcttt | cctccccagg | cggcacatct | ccagccactg | ccgacatgtg | atgggaagca | 120 |
| agtgtcagga | aatctgacca | cggtcctcag | ccagtgctgc | ctgattcagg | gccccttata | 180 |
| tgcaggaatc | caggatgtca | acacagtcct | tcacacacca | tatggatcac | ttctagcttg | 240 |
| gaggaaggaa | cgggagaagg | aaagagagaa | ggttcccatg | ggcctaaaca | ctgcatattt | 300 |
| atgtgcagac | acattgcagt | tgcatgttgg | tgaaaactga | ggcccaggtg | tctgcataca | 360 |
| aacagcaggc | cttcctataa | tttaaagatg | ttggtgaagg | gttcagcaag | ctcagacaat | 420 |
| ggaaggatga | aacatggcat | gcggcatgca | gtttgatcaa | aaagaaaaac | atgtctgccg | 480 |
| gacgtggtgg | ctcacgcctg | taatcctaac | act | | | 513 |

<210> SEQ ID NO 117
<211> LENGTH: 501
<212> TYPE: DNA
<213> ORGANISM: Homo sapiens

<400> SEQUENCE: 117

| | | | | | |
|---|---|---|---|---|---|
| acgagatgaa | tgatggtggc | cctgcctggc | atgaggaaag | tgagaaggga | aaccagcttg | 60 |
| ccagggaaga | gactgagctc | attctaaatc | tgatgcacca | ttcaggcact | cagttggaat | 120 |
| ttaggggagc | tgggggaaat | gcagatgaat | gtgggtgagg | atggcccaaa | agagacatgt | 180 |
| accaggaggt | tcacaccaag | aatgtgacag | gaaaaagcaa | aagacccagc | aataggagga | 240 |
| gggtgaaatc | cttctgtggg | acaaacacca | aggggcagag | gaggcagata | cgagtaaagg | 300 |
| agaagaatcg | cttttatcc | tatattcttc | tgtactgttt | taagtttttt | acgaaaaggc | 360 |
| actcatgtgg | ttctggtaaa | attatacaaa | tgatttcaac | aacaacaaca | acaaagaatt | 420 |
| tgaagtagac | aagaggccca | aaaatataga | tctgagagtc | attgacgcgc | aggtaatagg | 480 |
| tgaagccttg | aaaattaata | t | | | | 501 |

<210> SEQ ID NO 118
<211> LENGTH: 516
<212> TYPE: DNA
<213> ORGANISM: Homo sapiens

<400> SEQUENCE: 118

| | | | | | |
|---|---|---|---|---|---|
| acgagatgaa | tgatggtggc | cctgcctggc | atgaggaaag | tgagaaggga | aaccagcttg | 60 |
| ccagggaaga | gactgagctc | attctaaatc | tgatgcacca | ttcaggcact | cagttggaat | 120 |
| ttaggggagc | tgggggaaat | gcagatgaat | gtgggtgagg | atgcccaaa | agagacatgt | 180 |
| accaggaggt | tcacaccaag | aatgtgacag | gaaaaagcaa | aagacccagc | aataggagga | 240 |
| gggtgaaatc | aactacggca | cgcccttct | gtgggacaaa | caccaagggg | cagaggaggc | 300 |
| agatacgagt | aaaggagaag | aatcgctttt | tatcctatat | tcttctgtac | tgttttaagt | 360 |
| tttttacgaa | aaggcactca | tgtggttctg | gtaaaattat | acaaatgatt | tcaacaacaa | 420 |
| caacaacaaa | gaatttgaag | tagacaagag | gcccaaaaat | atagatctga | gagtcattga | 480 |
| cgcgcaggta | ataggtgaag | ccttgaaaat | taatat | | | 516 |

<210> SEQ ID NO 119
<211> LENGTH: 501

<212> TYPE: DNA
<213> ORGANISM: Homo sapiens

<400> SEQUENCE: 119

```
agtgagtgat ccatctccaa aattccattt tagagtaggg tttccaggat ccatccgatc    60
ccactggctt gtgttcattt tctgaagaca agagatggag ggttgcatgc aggttgctag   120
gggactgctc ctgtgagata cacctgcaaa gaagtgaaga agacaggagt ggaggaaagg   180
caaagggttg agctgacctg ccacacagtt taactgagac ctcagacaac cttctgagaa   240
gctctggagc cattgtatta agacaagatt tttgggcttt taaatgtctg gactttgact   300
gcagggcaca ccatgggaga gagaataacc ttgagtaagg cagtttcctt ttgccaaggg   360
caattcccat gcacaaatca actgtgaacc ttcaaaagct gaaacgctga gcatctgggt   420
aaggaccttg aagagaggac ctaaaaggaa caacaaagga tttcccctt ttcctaattt     480
ctgcctctct gctactcaat c                                             501
```

<210> SEQ ID NO 120
<211> LENGTH: 517
<212> TYPE: DNA
<213> ORGANISM: Homo sapiens

<400> SEQUENCE: 120

```
agtgagtgat ccatctccaa aattccattt tagagtaggg tttccaggat ccatccgatc    60
ccactggctt gtgttcattt tctgaagaca agagatggag ggttgcatgc aggttgctag   120
gggactgctc ctgtgagata cacctgcaaa gaagtgaaga agacaggagt ggaggaaagg   180
caaagggttg agctgacctg ccacacagtt taactgagac ctcagacaac cttctgagaa   240
gctctggagc catgatggtt cttcagaatt gtattaagac aagatttttg gcttttaaa    300
tgtctggact ttgactgcag ggcacaccat gggagagaga ataaccttga gtaaggcagt   360
ttccttttgc caagggcaat cccatgcac aaatcaactg tgaaccttca aaagctgaaa    420
cgctgagcat ctgggtaagg accttgaaga gaggacctaa aaggaacaac aaaggatttc   480
cccttttcc taatttctgc ctctctgcta ctcaatc                             517
```

<210> SEQ ID NO 121
<211> LENGTH: 501
<212> TYPE: DNA
<213> ORGANISM: Homo sapiens

<400> SEQUENCE: 121

```
ccttcaggct cagccccagg gtgctgtgct tcgccaaagt ctagcctgaa tgtgcatgcc    60
atgacaagcg gtcaatgcat ttggtctatt tttgcagggt taaagacaaa gtgttactgt   120
tctcctttaa acaagctaga ctggaccaga ttgtccaccc tggactagct ggcataacag   180
atcctcttgg ctctctgagg gcgccttctc tccatcagag gtcgcacagc accaccttga   240
ttccaggatt agcaatcgcc aactgcgtaa gcccaactgc acatgcaatc atatgacatg   300
tgatcccatg gcaaatgtaa tcaccgctca accaatccca ggtaacggtg ccatgttgct   360
tcccaatcac actgcagcta atttgctcta ttaaccaaag aatgagcaag gctgctgcct   420
tctcttgctt cttgaacact cactgctgct ctgggccggc ctgccttcct acattctcaa   480
tttgaggcaa tgaataatct a                                             501
```

<210> SEQ ID NO 122
<211> LENGTH: 527
<212> TYPE: DNA

<213> ORGANISM: Homo sapiens

<400> SEQUENCE: 122

```
ccttcaggct cagccccagg gtgctgtgct tcgccaaagt ctagcctgaa tgtgcatgcc    60
atgacaagcg gtcaatgcat ttggtctatt tttgcagggt taaagacaaa gtgttactgt   120
tctcctttaa acaagctaga ctggaccaga ttgtccaccc tggactagct ggcataacag   180
atcctcttgg ctctctgagg gcgccttctc tccatcagag gtcgcacagc accaccttga   240
ttccaggatt cttggcacca ccttgattcc aggattagca atcgccaact gcgtaagccc   300
aactgcacat gcaatcatat gacatgtgat cccatggcaa atgtaatcac cgctcaacca   360
atcccaggta acggtgccat gttgcttccc aatcacactg cagctaattt gctctattaa   420
ccaaagaatg agcaaggctg ctgccttctc ttgcttcttg aacactcact gctgctctgg   480
gccggcctgc cttcctacat tctcaatttg aggcaatgaa taatcta              527
```

<210> SEQ ID NO 123
<211> LENGTH: 509
<212> TYPE: DNA
<213> ORGANISM: Homo sapiens

<400> SEQUENCE: 123

```
gccttagcgc tatatggcaa caatcttgtt atatattaag gaaacaggcg tgggcgagga    60
agattatact ccaaagtcgc tggaaaagag catggatttc tgctgtagcg ccttgaaatt   120
tcaacctcca gacttcttac atgaggtaat tcaaggtcat tattctttag gccactgtaa   180
atggctgcag ctcactgaac tgacataaaa ggtgtgcatc atccaaaaa gctttctaag    240
ctaagcttaa gctcggtatt ggtcaaaatg tgctcttctt cttttgctga ggtttcatct   300
atcaatcaat atttcaaaat acttacagct aatgcttact tggagggaga caggaaaggg   360
acaaccttcc atactatttt tcaaattatt tcagacacaa taaatccatc tggaaaaaca   420
tccacttttta caagttctta attcagatct attttgttct taccatgcaa aatagatcaa   480
atgctttttt atatgtgaac tgtacaacc                                    509
```

<210> SEQ ID NO 124
<211> LENGTH: 517
<212> TYPE: DNA
<213> ORGANISM: Homo sapiens

<400> SEQUENCE: 124

```
gccttagcgc tatatggcaa caatcttgtt atatattaag gaaacaggcg tgggcgagga    60
agattatact ccaaagtcgc tggaaaagag catggatttc tgctgtagcg ccttgaaatt   120
tcaacctcca gacttcttac atgaggtaat tcaaggtcat tattctttag gccactgtaa   180
atggctgcag ctcactgaac tgacataaaa ggtgtgcatc atccaaaaa gctttctaag    240
ctaagcttaa gttagttatc tcggtattgg tcaaaatgtg ctcttcttct tttgctgagg   300
tttcatctat caatcaatat ttcaaaatac ttacagctaa tgcttacttg agggagaca    360
ggaaagggac aaccttccat actatttttc aaattatttc agacacaata aatccatctg   420
gaaaaacatc cacttttaca agttcttaat tcagatctat tttgttctta ccatgcaaaa   480
tagatcaaat gctttttat atgtgaactg tacaacc                             517
```

<210> SEQ ID NO 125
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 1 and 2

<400> SEQUENCE: 125
taaattctaa cctgcactca aagg                                              24

<210> SEQ ID NO 126
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 1 and 2

<400> SEQUENCE: 126
ttagtcctgg atagccttag aaaat                                             25

<210> SEQ ID NO 127
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 3 and 4

<400> SEQUENCE: 127
tgctgacgaa attgcagtaa cta                                               23

<210> SEQ ID NO 128
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 3 and 4

<400> SEQUENCE: 128
cacttctcta gggtctatcc agctt                                             25

<210> SEQ ID NO 129
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 5 and 6

<400> SEQUENCE: 129
tccgttgaaa ttctgccata                                                   20

<210> SEQ ID NO 130
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 5 and 6

<400> SEQUENCE: 130
aaactcactg gactgatagt gctg                                              24

<210> SEQ ID NO 131
<211> LENGTH: 21
<212> TYPE: DNA
<213> ORGANISM: Artificial Sequence
<220> FEATURE:

```
<223> OTHER INFORMATION: Description of artificial Sequence: Synthetic
      primer for SEQ ID NOS 7 and 8

<400> SEQUENCE: 131
ccctctgtcc tcatcaacat g                                              21

<210> SEQ ID NO 132
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 7 and 8

<400> SEQUENCE: 132
tggtaatttg ttacagtagc ccaaa                                          25

<210> SEQ ID NO 133
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 9 and 10

<400> SEQUENCE: 133
acactctatg ccatgctcct g                                              21

<210> SEQ ID NO 134
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 9 and 10

<400> SEQUENCE: 134
ctgcaactgc tgtcttacct ct                                             22

<210> SEQ ID NO 135
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 11 and 12

<400> SEQUENCE: 135
gcaatctctc ctttggcaac t                                              21

<210> SEQ ID NO 136
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 11 and 12

<400> SEQUENCE: 136
agagcgcatc aggttgtctg                                                20

<210> SEQ ID NO 137
<211> LENGTH: 25
<212> TYPE: DNA
<213> ORGANISM: Artificial Sequence
<220> FEATURE:
<223> OTHER INFORMATION: Description of artificial Sequence: Synthetic
``` primer for SEQ ID NOS 13 and 14

<400> SEQUENCE: 137
agatgacaga tatgttcact ggcta                                                25

<210> SEQ ID NO 138
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 13 and 14

<400> SEQUENCE: 138
agagccctca agttaagaat gattt                                                25

<210> SEQ ID NO 139
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 15 and 16

<400> SEQUENCE: 139
agtggtttgt gatcttgcca tc                                                   22

<210> SEQ ID NO 140
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 15 and 16

<400> SEQUENCE: 140
aatgggtcat gtcttccctt c                                                    21

<210> SEQ ID NO 141
<211> LENGTH: 19
<212> TYPE: DNA
<213> ORGANISM: Artificial Sequence
<220> FEATURE:
<223> OTHER INFORMATION: Description of artificial Sequence: Synthetic
      primer for SEQ ID NOS 17 and 18

<400> SEQUENCE: 141
ggctggattg aagtgcatt                                                       19

<210> SEQ ID NO 142
<211> LENGTH: 19
<212> TYPE: DNA
<213> ORGANISM: Artificial Sequence
<220> FEATURE:
<223> OTHER INFORMATION: Description of artificial Sequence: Synthetic
      primer for SEQ ID NOS 17 and 18

<400> SEQUENCE: 142
gctgtgtcat cagggatgg                                                       19

<210> SEQ ID NO 143
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 19 and 20

<400> SEQUENCE: 143
acatcagagc cctaaacaaa caa                                           23

<210> SEQ ID NO 144
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 19 and 20

<400> SEQUENCE: 144
agtggtaaat ctttgtttga aggtg                                         25

<210> SEQ ID NO 145
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 21 and 22

<400> SEQUENCE: 145
gttgagagtc gtgggtttat cc                                            22

<210> SEQ ID NO 146
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 21 and 22

<400> SEQUENCE: 146
tatcctttaa tcaggaatgg gttt                                          24

<210> SEQ ID NO 147
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 23 and 24

<400> SEQUENCE: 147
ggaaggaata acaagtacct cagtt                                         25

<210> SEQ ID NO 148
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 23 and 24

<400> SEQUENCE: 148
aaagtgtcac aagaccctta aactt                                         25

<210> SEQ ID NO 149
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 25 and 26

<400> SEQUENCE: 149
ccaatgttca tcagaactgt caata                                              25

<210> SEQ ID NO 150
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 25 and 26

<400> SEQUENCE: 150
gactcccaag agctgtggat t                                                  21

<210> SEQ ID NO 151
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 27 and 28

<400> SEQUENCE: 151
tgaagtttga aagaataatg taggc                                              25

<210> SEQ ID NO 152
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 27 and 28

<400> SEQUENCE: 152
acatgattca acagaattga ttttc                                              25

<210> SEQ ID NO 153
<211> LENGTH: 27
<212> TYPE: DNA
<213> ORGANISM: Artificial Sequence
<220> FEATURE:
<223> OTHER INFORMATION: Description of artificial Sequence: Synthetic
      primer for SEQ ID NOS 29 and 30

<400> SEQUENCE: 153
tcagtcctat ttagtagaag ctcaatt                                            27

<210> SEQ ID NO 154
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 29 and 30

<400> SEQUENCE: 154
gtttaatcct atcaaagaag cattg                                              25

<210> SEQ ID NO 155
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 31 and 32

<400> SEQUENCE: 155
ctcctttgtt cctcctaatc tcttt                                            25

<210> SEQ ID NO 156
<211> LENGTH: 26
<212> TYPE: DNA
<213> ORGANISM: Artificial Sequence
<220> FEATURE:
<223> OTHER INFORMATION: Description of artificial Sequence: Synthetic
      primer for SEQ ID NOS 31 and 32

<400> SEQUENCE: 156
gaatatatga gactcacact ggtcct                                           26

<210> SEQ ID NO 157
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 33 and 34

<400> SEQUENCE: 157
tagggtcata aacccagtct gc                                               22

<210> SEQ ID NO 158
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 33 and 34

<400> SEQUENCE: 158
gttttaggtc tcagcatcac gtag                                             24

<210> SEQ ID NO 159
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 35 and 36

<400> SEQUENCE: 159
gtgctggtcc attctcttgt aa                                               22

<210> SEQ ID NO 160
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 35 and 36

<400> SEQUENCE: 160
ctaggtgcag agagggatac tg                                               22

<210> SEQ ID NO 161
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 37 and 38

<400> SEQUENCE: 161
gagggcgact ataaagagga ttc                                           23

<210> SEQ ID NO 162
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 37 and 38

<400> SEQUENCE: 162
ttcacgaagc cacaagtatt                                               20

<210> SEQ ID NO 163
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 39 and 40

<400> SEQUENCE: 163
aaattaaatt caaatgtcca actg                                          24

<210> SEQ ID NO 164
<211> LENGTH: 28
<212> TYPE: DNA
<213> ORGANISM: Artificial Sequence
<220> FEATURE:
<223> OTHER INFORMATION: Description of artificial Sequence: Synthetic
      primer for SEQ ID NOS 39 and 40

<400> SEQUENCE: 164
tgtgtaggag ggtgttttat agacaaat                                      28

<210> SEQ ID NO 165
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 41 and 42

<400> SEQUENCE: 165
aatggcaaag atacaggtct gg                                            22

<210> SEQ ID NO 166
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 41 and 42

<400> SEQUENCE: 166
aggtgaagtt gaggctcctg                                               20

<210> SEQ ID NO 167
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 43 and 44

<400> SEQUENCE: 167
tttctaaagg catctgaaat agtgg                                         25

<210> SEQ ID NO 168
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 43 and 44

<400> SEQUENCE: 168
cctacatgag gatgtccttc tactt                                           25

<210> SEQ ID NO 169
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 45 and 46

<400> SEQUENCE: 169
agcccaccag agcactacag                                                 20

<210> SEQ ID NO 170
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 45 and 46

<400> SEQUENCE: 170
agatgctgtc agggcacgac                                                 20

<210> SEQ ID NO 171
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 47 and 48

<400> SEQUENCE: 171
tagactcaag aattgacatt gacac                                           25

<210> SEQ ID NO 172
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 47 and 48

<400> SEQUENCE: 172
gaagtctatt cccctactcc ttg                                             23

<210> SEQ ID NO 173
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 49 and 50

<400> SEQUENCE: 173
tgggtagggt gttatgtgta tcttt                                           25

<210> SEQ ID NO 174
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 49 and 50

<400> SEQUENCE: 174
gttccaacag aatttagctt actgc                          25

<210> SEQ ID NO 175
<211> LENGTH: 22
<212> TYPE: DNA
<213> ORGANISM: Artificial Sequence
<220> FEATURE:
<223> OTHER INFORMATION: Description of artificial Sequence: Synthetic primer for SEQ ID NOS 51 and 52

<400> SEQUENCE: 175
aagagtgaaa ctccgtctca aa                             22

<210> SEQ ID NO 176
<211> LENGTH: 26
<212> TYPE: DNA
<213> ORGANISM: Artificial Sequence
<220> FEATURE:
<223> OTHER INFORMATION: Description of artificial Sequence: Synthetic primer for SEQ ID NOS 51 and 52

<400> SEQUENCE: 176
ctgccttcca aaatactatt gttatc                         26

<210> SEQ ID NO 177
<211> LENGTH: 22
<212> TYPE: DNA
<213> ORGANISM: Artificial Sequence
<220> FEATURE:
<223> OTHER INFORMATION: Description of artificial Sequence: Synthetic primer for SEQ ID NOS 53 and 54

<400> SEQUENCE: 177
cacatcccat cagcttctac aa                             22

<210> SEQ ID NO 178
<211> LENGTH: 20
<212> TYPE: DNA
<213> ORGANISM: Artificial Sequence
<220> FEATURE:
<223> OTHER INFORMATION: Description of artificial Sequence: Synthetic primer for SEQ ID NOS 53 and 54

<400> SEQUENCE: 178
gagccgggtt ctcgtctagt                                20

<210> SEQ ID NO 179
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 55 and 56

<400> SEQUENCE: 179
ttaccaccaa gagttacatt acatg                          25

<210> SEQ ID NO 180
<211> LENGTH: 21
<212> TYPE: DNA
<213> ORGANISM: Artificial Sequence
<220> FEATURE:
<223> OTHER INFORMATION: Description of artificial Sequence: Synthetic primer for SEQ ID NOS 55 and 56

<400> SEQUENCE: 180
tgttgcgaaa ggaaacgcta g                                              21

<210> SEQ ID NO 181
<211> LENGTH: 20
<212> TYPE: DNA
<213> ORGANISM: Artificial Sequence
<220> FEATURE:
<223> OTHER INFORMATION: Description of artificial Sequence: Synthetic primer for SEQ ID NOS 57 and 58

<400> SEQUENCE: 181
gaagcggtct ggaagtcagg                                                20

<210> SEQ ID NO 182
<211> LENGTH: 18
<212> TYPE: DNA
<213> ORGANISM: Artificial Sequence
<220> FEATURE:
<223> OTHER INFORMATION: Description of artificial Sequence: Synthetic primer for SEQ ID NOS 57 and 58

<400> SEQUENCE: 182
acactctttg cagggtac                                                  18

<210> SEQ ID NO 183
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 59 and 60

<400> SEQUENCE: 183
ttacttgccc aaaagaaaac atatc                                          25

<210> SEQ ID NO 184
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 59 and 60

<400> SEQUENCE: 184
tgcaagatat tccttggtaa ttcag                                          25

<210> SEQ ID NO 185
<211> LENGTH: 23
<212> TYPE: DNA
<213> ORGANISM: Artificial Sequence
<220> FEATURE:
<223> OTHER INFORMATION: Description of artificial Sequence: Synthetic primer for SEQ ID NOS 61 and 62

<400> SEQUENCE: 185
cctgggctct gtaaagaata gtg                                            23

<210> SEQ ID NO 186

```
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 61 and 62

<400> SEQUENCE: 186
gccaaccatc agcttaaact                                                   20

<210> SEQ ID NO 187
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 63 and 64

<400> SEQUENCE: 187
cgctttgaag tggtaccaga gca                                               23

<210> SEQ ID NO 188
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 63 and 64

<400> SEQUENCE: 188
aatgcatgcc taatattttc aggga                                             25

<210> SEQ ID NO 189
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 65 and 66

<400> SEQUENCE: 189
ctttgttgct agtttgtcat ttgaa                                             25

<210> SEQ ID NO 190
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 65 and 66

<400> SEQUENCE: 190
ttgattacac tataggagcc ctgaa                                             25

<210> SEQ ID NO 191
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 67 and 68

<400> SEQUENCE: 191
agacaacttt atgtgacttg aatcc                                             25

<210> SEQ ID NO 192
<211> LENGTH: 27
```

```
<212> TYPE: DNA
<213> ORGANISM: Artificial Sequence
<220> FEATURE:
<223> OTHER INFORMATION: Description of artificial Sequence: Synthetic
      primer for SEQ ID NOS 67 and 68

<400> SEQUENCE: 192
gcaagaatat agaaaactta acaccac                                      27

<210> SEQ ID NO 193
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 69 and 70

<400> SEQUENCE: 193
ctaatttagg cacaaacctg atct                                         24

<210> SEQ ID NO 194
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 69 and 70

<400> SEQUENCE: 194
attgatcata tcctatcctt catca                                        25

<210> SEQ ID NO 195
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 71 and 72

<400> SEQUENCE: 195
ctcgtagcct cattgcttcc t                                            21

<210> SEQ ID NO 196
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 71 and 72

<400> SEQUENCE: 196
ccaatccaaa gccaagaaat c                                            21

<210> SEQ ID NO 197
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 73 and 74

<400> SEQUENCE: 197
ggcctcttgt tctttatctt gag                                          23

<210> SEQ ID NO 198
<211> LENGTH: 26
<212> TYPE: DNA
```

<213> ORGANISM: Artificial Sequence
<220> FEATURE:
<223> OTHER INFORMATION: Description of artificial Sequence: Synthetic primer for SEQ ID NOS 73 and 74

<400> SEQUENCE: 198
tgatactaga ctttctccat ctcatt                                          26

<210> SEQ ID NO 199
<211> LENGTH: 24
<212> TYPE: DNA
<213> ORGANISM: Artificial Sequence
<220> FEATURE:
<223> OTHER INFORMATION: Description of artificial Sequence: Synthetic primer for SEQ ID NOS 75 and 76

<400> SEQUENCE: 199
atcactttgt ttcttgctct gaat                                            24

<210> SEQ ID NO 200
<211> LENGTH: 24
<212> TYPE: DNA
<213> ORGANISM: Artificial Sequence
<220> FEATURE:
<223> OTHER INFORMATION: Description of artificial Sequence: Synthetic primer for SEQ ID NOS 75 and 76

<400> SEQUENCE: 200
actaacctag aacatgccat tagc                                            24

<210> SEQ ID NO 201
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 77 and 78

<400> SEQUENCE: 201
gtcatggcac tcttctagca agtat                                           25

<210> SEQ ID NO 202
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 77 and 78

<400> SEQUENCE: 202
agggtaatcg gattctgtag ttcat                                           25

<210> SEQ ID NO 203
<211> LENGTH: 25
<212> TYPE: DNA
<213> ORGANISM: Artificial Sequence
<220> FEATURE:
<223> OTHER INFORMATION: Description of artificial Sequence: Synthetic primer for SEQ ID NOS 79 and 80

<400> SEQUENCE: 203
ggcttatatc aaatgtcctt atgaa                                           25

<210> SEQ ID NO 204
<211> LENGTH: 25
<212> TYPE: DNA
<213> ORGANISM: Artificial Sequence

```
<220> FEATURE:
<223> OTHER INFORMATION: Description of artificial Sequence: Synthetic
      primer for SEQ ID NOS 79 and 80

<400> SEQUENCE: 204
tactattcca ttatccgaaa cactg                                            25

<210> SEQ ID NO 205
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 81 and 82

<400> SEQUENCE: 205
ttcaggtacc cccttccctc c                                                21

<210> SEQ ID NO 206
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 81 and 82

<400> SEQUENCE: 206
ccttcaggta cccttccctc c                                                21

<210> SEQ ID NO 207
<211> LENGTH: 19
<212> TYPE: DNA
<213> ORGANISM: Artificial Sequence
<220> FEATURE:
<223> OTHER INFORMATION: Description of artificial Sequence: Synthetic
      primer for SEQ ID NOS 83 and 84

<400> SEQUENCE: 207
aattttgttc tttttatt                                                    19

<210> SEQ ID NO 208
<211> LENGTH: 19
<212> TYPE: DNA
<213> ORGANISM: Artificial Sequence
<220> FEATURE:
<223> OTHER INFORMATION: Description of artificial Sequence: Synthetic
      primer for SEQ ID NOS 83 and 84

<400> SEQUENCE: 208 aaatttgtt tttttatta                                                    19

<210> SEQ ID NO 209
<211> LENGTH: 17
<212> TYPE: DNA
<213> ORGANISM: Artificial Sequence
<220> FEATURE:
<223> OTHER INFORMATION: Description of artificial Sequence: Synthetic
      primer for SEQ ID NOS 85 and 86

<400> SEQUENCE: 209
aagagagttg ttgtgag                                                     17

<210> SEQ ID NO 210
<211> LENGTH: 17
<212> TYPE: DNA
<213> ORGANISM: Artificial Sequence
<220> FEATURE:
```

```
<223> OTHER INFORMATION: Description of artificial Sequence: Synthetic
      primer for SEQ ID NOS 85 and 86

<400> SEQUENCE: 210
agagagttgt gagctga                                                  17

<210> SEQ ID NO 211
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 87 and 88

<400> SEQUENCE: 211
gaaggaatgg aagaaatgct gga                                           23

<210> SEQ ID NO 212
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 87 and 88

<400> SEQUENCE: 212
ggaaggaatg gaaatgctgg ag                                            22

<210> SEQ ID NO 213
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 89 and 90

<400> SEQUENCE: 213
ggaatggagg aggagaagtt                                               20

<210> SEQ ID NO 214
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 89 and 90

<400> SEQUENCE: 214
ctggaatgga ggagaagttt t                                             21

<210> SEQ ID NO 215
<211> LENGTH: 17
<212> TYPE: DNA
<213> ORGANISM: Artificial Sequence
<220> FEATURE:
<223> OTHER INFORMATION: Description of artificial Sequence: Synthetic
      primer for SEQ ID NOS 91 and 92

<400> SEQUENCE: 215
gggaaattct tcttggt                                                  17

<210> SEQ ID NO 216
<211> LENGTH: 17
<212> TYPE: DNA
<213> ORGANISM: Artificial Sequence
<220> FEATURE:
<223> OTHER INFORMATION: Description of artificial Sequence: Synthetic
``` primer for SEQ ID NOS 91 and 92

<400> SEQUENCE: 216
gggaaattct tggtttt                                                        17

<210> SEQ ID NO 217
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 93 and 94

<400> SEQUENCE: 217
accctcctca ctaactgtcc                                                     20

<210> SEQ ID NO 218
<211> LENGTH: 18
<212> TYPE: DNA
<213> ORGANISM: Artificial Sequence
<220> FEATURE:
<223> OTHER INFORMATION: Description of artificial Sequence: Synthetic
      primer for SEQ ID NOS 93 and 94

<400> SEQUENCE: 218
tgtccctcct aactgtcc                                                       18

<210> SEQ ID NO 219
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 95 and 96

<400> SEQUENCE: 219
gcaggctgat gagtttggtt                                                     20

<210> SEQ ID NO 220
<211> LENGTH: 28
<212> TYPE: DNA
<213> ORGANISM: Artificial Sequence
<220> FEATURE:
<223> OTHER INFORMATION: Description of artificial Sequence: Synthetic
      primer for SEQ ID NOS 95 and 96

<400> SEQUENCE: 220
aacatactac aacaacatca agtttctt                                            28

<210> SEQ ID NO 221
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 97 and 98

<400> SEQUENCE: 221
attttgtccc attaccccat tt                                                  22

<210> SEQ ID NO 222
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 97 and 98

<400> SEQUENCE: 222
agatcacttc tctcctgctt aggat                                    25

<210> SEQ ID NO 223
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 99 and 100

<400> SEQUENCE: 223
tttgcatcat taaagggttt gc                                       22

<210> SEQ ID NO 224
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 99 and 100

<400> SEQUENCE: 224
cacttgtagg gctttgcact tc                                       22

<210> SEQ ID NO 225
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 101 and 102

<400> SEQUENCE: 225
tgttagtggt caggtcacat g                                        21

<210> SEQ ID NO 226
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 101 and 102

<400> SEQUENCE: 226
agttagtggt cacatgtgca tc                                       22

<210> SEQ ID NO 227
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 103 and 104

<400> SEQUENCE: 227
taatgataag gaggccaact caa                                      23

<210> SEQ ID NO 228
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 103 and 104

```
<400> SEQUENCE: 228
tttggttgct tgtcctatta gct                                              23

<210> SEQ ID NO 229
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 105 and 106

<400> SEQUENCE: 229
atgttgcttc cctatctaca caac                                             24

<210> SEQ ID NO 230
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 105 and 106

<400> SEQUENCE: 230
gaaaagcaca agaagaaaat aactg                                            25

<210> SEQ ID NO 231
<211> LENGTH: 19
<212> TYPE: DNA
<213> ORGANISM: Artificial Sequence
<220> FEATURE:
<223> OTHER INFORMATION: Description of artificial Sequence: Synthetic
      primer for SEQ ID NOS 107 and 108

<400> SEQUENCE: 231
cacagcgtgg gtacaagct                                                   19

<210> SEQ ID NO 232
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 107 and 108

<400> SEQUENCE: 232
agccacagga ggagaatgac                                                  20

<210> SEQ ID NO 233
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 109 and 110

<400> SEQUENCE: 233
tccctctctt ccacgaaatc t                                                21

<210> SEQ ID NO 234
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 109 and 110

<400> SEQUENCE: 234
```
ttcagattgg ttggctgacc					20

<210> SEQ ID NO 235
<211> LENGTH: 23
<212> TYPE: DNA
<213> ORGANISM: Artificial Sequence
<220> FEATURE:
<223> OTHER INFORMATION: Description of artificial Sequence: Synthetic
      primer for SEQ ID NOS 111 and 112

<400> SEQUENCE: 235
atcgtgacag gtcttattga aaa					23

<210> SEQ ID NO 236
<211> LENGTH: 27
<212> TYPE: DNA
<213> ORGANISM: Artificial Sequence
<220> FEATURE:
<223> OTHER INFORMATION: Description of artificial Sequence: Synthetic
      primer for SEQ ID NOS 111 and 112

<400> SEQUENCE: 236
agcttaggct tcaagttatt tctattt					27

<210> SEQ ID NO 237
<211> LENGTH: 24
<212> TYPE: DNA
<213> ORGANISM: Artificial Sequence
<220> FEATURE:
<223> OTHER INFORMATION: Description of artificial Sequence: Synthetic
      primer for SEQ ID NOS 113 and 114

<400> SEQUENCE: 237
acccagctga atgaaactta atag					24

<210> SEQ ID NO 238
<211> LENGTH: 25
<212> TYPE: DNA
<213> ORGANISM: Artificial Sequence
<220> FEATURE:
<223> OTHER INFORMATION: Description of artificial Sequence: Synthetic
      primer for SEQ ID NOS 113 and 114

<400> SEQUENCE: 238
tgttaacggt ggctctaata ctaac					25

<210> SEQ ID NO 239
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 115 and 116

<400> SEQUENCE: 239
caacacagtc cttcacacac c					21

<210> SEQ ID NO 240
<211> LENGTH: 20
<212> TYPE: DNA
<213> ORGANISM: Artificial Sequence
<220> FEATURE:
<223> OTHER INFORMATION: Description of artificial Sequence: Synthetic
      primer for SEQ ID NOS 115 and 116

<400> SEQUENCE: 240

```
caactgcaat gtgtctgcac                                              20
```

<210> SEQ ID NO 241
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 117 and 118

<400> SEQUENCE: 241

```
aaagacccag caataggagg a                                            21
```

<210> SEQ ID NO 242
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 117 and 118

<400> SEQUENCE: 242

```
ttggtgtttg tcccacagaa g                                            21
```

<210> SEQ ID NO 243
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 119 and 120

<400> SEQUENCE: 243

```
tgagacctca gacaaccttc tg                                           22
```

<210> SEQ ID NO 244
<211> LENGTH: 22
<212> TYPE: DNA
<213> ORGANISM: Artificial Sequence
<220> FEATURE:
<223> OTHER INFORMATION: Description of artificial Sequence: Synthetic
      primer for SEQ ID NOS 119 and 120

<400> SEQUENCE: 244

```
tccagacatt taaaagccca aa                                           22
```

<210> SEQ ID NO 245
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 121 and 122

<400> SEQUENCE: 245

```
gccttctctc catcagaggt c                                            21
```

<210> SEQ ID NO 246
<211> LENGTH: 21
<212> TYPE: DNA
<213> ORGANISM: Artificial Sequence
<220> FEATURE:
<223> OTHER INFORMATION: Description of artificial Sequence: Synthetic
      primer for SEQ ID NOS 121 and 122

<400> SEQUENCE: 246

```
attggttgag cggtgattac a                                            21
```

<210> SEQ ID NO 247
<211> LENGTH: 22
<212> TYPE: DNA
<213> ORGANISM: Artificial Sequence
<220> FEATURE:
<223> OTHER INFORMATION: Description of artificial Sequence: Synthetic primer for SEQ ID NOS 123 and 124

<400> SEQUENCE: 247
ttctttaggc cactgtaaat gg                                              22

<210> SEQ ID NO 248
<211> LENGTH: 24
<212> TYPE: DNA
<213> ORGANISM: Artificial Sequence
<220> FEATURE:
<223> OTHER INFORMATION: Description of artificial Sequence: Synthetic primer for SEQ ID NOS 123 and 124

<400> SEQUENCE: 248
ttgattgata gatgaaacct cagc                                            24

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic primer for DIP 63

<400> SEQUENCE: 249
ctctgtctcc actgggaatg tc                                              22

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic primer for DIP 63

<400> SEQUENCE: 250
atctgttagg cgcactgtgt c                                               21

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic primer for DIP 41

<400> SEQUENCE: 251
cagactgaga gacagccttg                                                 20

<210> SEQ ID NO 252
<211> LENGTH: 20
<212> TYPE: DNA
<213> ORGANISM: Artificial Sequence
<220> FEATURE:
<223> OTHER INFORMATION: Description of Artificial Sequence: Synthetic primer for DIP 41

<400> SEQUENCE: 252
atatccttaa gctccaggga                                                 20

<210> SEQ ID NO 253
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 42

<400> SEQUENCE: 253
tttgaaatat gtcccaagga                                                     20

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for DIP 42

<400> SEQUENCE: 254
tcaattttat ctccaatttc gt                                                  22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for DIP 43

<400> SEQUENCE: 255
gcacatttca ttaagtctgt ca                                                  22

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for DIP 43

<400> SEQUENCE: 256
gtctgtgaac tcagtccaga a                                                   21

<210> SEQ ID NO 257
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 44

<400> SEQUENCE: 257
atcaacacag acctgcctta                                                     20

<210> SEQ ID NO 258
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 44

<400> SEQUENCE: 258
ttggccatct gactatgaat                                                     20

```
<210> SEQ ID NO 259
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 45

<400> SEQUENCE: 259
taccaagcca gaactaccag                                                   20

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 45

<400> SEQUENCE: 260
ttgttgccaa atactgtcaa                                                   20

<210> SEQ ID NO 261
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 46

<400> SEQUENCE: 261
tggaagacac gtcctaagag                                                   20

<210> SEQ ID NO 262
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 46

<400> SEQUENCE: 262
aaatgggtga ttattcctcc                                                   20

<210> SEQ ID NO 263
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 47

<400> SEQUENCE: 263
gaacagtgac atggacacct                                                   20

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 47

<400> SEQUENCE: 264
aagacacagc aaggtgatgt                                                   20

<210> SEQ ID NO 265
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 51

<400> SEQUENCE: 265
agattctcag tcacctgctg                                              20

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 51

<400> SEQUENCE: 266
actgattcac cacattccag                                              20

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for DIP 1

<400> SEQUENCE: 267
taaattctaa cctgcactca aagga                                        25

<210> SEQ ID NO 268
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for DIP 1

<400> SEQUENCE: 268
tacagcatat tagtcctgga tagcc                                        25

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for DIP 32

<400> SEQUENCE: 269
cctttgaagt ggtaccagag ca                                           22

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      primer for DIP 32

<400> SEQUENCE: 270
gcatgcctaa tattttcagg gaa                                          23

<210> SEQ ID NO 271
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      primer for DIP 29

<400> SEQUENCE: 271
agggaagcgg tctggaagt                                                19

<210> SEQ ID NO 272
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for DIP 29

<400> SEQUENCE: 272
cccacactct ttgcagggta                                               20

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for DIP 17

<400> SEQUENCE: 273
ggtcataaac ccagtctgct g                                             21

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for DIP 17

<400> SEQUENCE: 274
gttttaggtc tcagcatcac gtag                                          24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for DIP 20

<400> SEQUENCE: 275
aaattaaatt caaatgtcca actg                                          24

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      primer for DIP 20

<400> SEQUENCE: 276
ttgtaaagct ggagaatgga gaa                                           23

<210> SEQ ID NO 277
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer for DIP 18

<400> SEQUENCE: 277
gtgtgctggt ccattctctt g                                            21

<210> SEQ ID NO 278
<211> LENGTH: 19
<212> TYPE: DNA
<213> ORGANISM: Artificial Sequence
<220> FEATURE:
<223> OTHER INFORMATION: Description of Artificial Sequence: Synthetic
      primer for DIP 18

<400> SEQUENCE: 278
agaaggagcg atgccctag                                               19

<210> SEQ ID NO 279
<211> LENGTH: 26
<212> TYPE: DNA
<213> ORGANISM: Artificial
<220> FEATURE:
<223> OTHER INFORMATION: Description of Artificial Sequence: Synthetic
      primer for DIP 19

<400> SEQUENCE: 279
ctataaagag gattcctgtg ttggtt                                       26

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for DIP 19

<400> SEQUENCE: 280
gttcacgaag ccacaagtat t                                            21

<210> SEQ ID NO 281
<211> LENGTH: 27
<212> TYPE: DNA
<213> ORGANISM: Artificial Sequence
<220> FEATURE:
<223> OTHER INFORMATION: Description of Artificial Sequence: Synthetic
      primer for DIP 15

<400> SEQUENCE: 281
tgcttttcag tcctatttag tagaagc                                      27

<210> SEQ ID NO 282
<211> LENGTH: 27
<212> TYPE: DNA
<213> ORGANISM: Artificial Sequence
<220> FEATURE:
<223> OTHER INFORMATION: Description of Artificial Sequence: Synthetic
      primer for DIP 15

<400> SEQUENCE: 282
tcctatcaaa gaagcattgt taatttt                                      27

<210> SEQ ID NO 283
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer for DIP 30

<400> SEQUENCE: 283
ttacttgccc aaaagaaaac atatc                                               25

<210> SEQ ID NO 284
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for DIP 30

<400> SEQUENCE: 284
atgcaagata ttccttggta attca                                               25

<210> SEQ ID NO 285
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for DIP 33

<400> SEQUENCE: 285
gtctgacttt gttgctagtt tgtca                                               25

<210> SEQ ID NO 286
<211> LENGTH: 25
<212> TYPE: DNA
<213> ORGANISM: Artificial Sequence
<220> FEATURE:
<223> OTHER INFORMATION: Description of Artificial Sequence: Synthetic
      primer for DIP 33

<400> SEQUENCE: 286
ttgattacac tataggagcc ctgaa                                               25

<210> SEQ ID NO 287
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for DIP 8

<400> SEQUENCE: 287
gatcagtggt ttgtgatctt gc                                                  22

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      primer for DIP 8

<400> SEQUENCE: 288
aatgggtcat gtcttccctt c                                                   21

<210> SEQ ID NO 289
<211> LENGTH: 501
<212> TYPE: DNA
<213> ORGANISM: Homo sapiens
```

```
<400> SEQUENCE: 289
atgataagcc caggataatc aacttgctta aggtgatgta accagttctc acacaagcct        60
tctctccaga atattaacac attcatgtga acgtgtgtgt gtaggcatat atcatgtatg       120
tgcacgcatg tccttttact ctgtctccac tgggaatgtc ttaattttca ttagattcca       180
agtaagaatc aaaataatga gaccatgctt tatatattct taaaattatt gcaaacatta       240
tatttacttt aaagtttctg tgacacagtg cgcctaacag atagtgggaa ttttatttat       300
gcataaaatg cactgcataa tgaagtaatt gagtcttcat tttccatatg gcgttctgga       360
cagtttggtt ttgaatgagt tggtaagatt cccaagtggt tgtcacacat gtggctgaga       420
gaaaattaaa gggctggctc tcctcatagt tccttcaggt caagaggaaa gcagctaata       480
ttattgactc ctcaacccaa a                                                 501

<210> SEQ ID NO 290
<211> LENGTH: 506
<212> TYPE: DNA
<213> ORGANISM: Homo sapiens

<400> SEQUENCE: 290
atgataagcc caggataatc aacttgctta aggtgatgta accagttctc acacaagcct        60
tctctccaga atattaacac attcatgtga acgtgtgtgt gtaggcatat atcatgtatg       120
tgcacgcatg tccttttact ctgtctccac tgggaatgtc ttaattttca ttagattcca       180
agtaagaatc aaaataatga gaccatgctt tatatattct taaaattatt gcaaacatta       240
tatttacttt taagtaaagt ttctgtgaca cagtgcgcct aacagatagt gggaatttta       300
tttatgcata aaatgcactg cataatgaag taattgagtc ttcattttcc atatggcgtt       360
ctggacagtt tggttttgaa tgagttggta agattcccaa gtggttgtca cacatgtggc       420
tgagagaaaa ttaaagggct ggctctcctc atagttcctt caggtcaaga ggaaagcagc       480
taatattatt gactcctcaa cccaaa                                            506
```

SUBSTANCES AND METHODS FOR A DNA BASED PROFILING ASSAY

SEQUENCE LISTING

The instant application contains a Sequence Listing which has been submitted via EFS-Web and is hereby incorporated by reference in its entirety. Said ASCII copy, created on Feb. 11, 2011, is named 54BIO1US.txt and is 135,587 byte in size.

FIELD OF THE INVENTION

The present invention is generally directed to the detection of genetic markers in a genomic system. In one particular embodiment of the invention it is specifically directed to the simultaneous amplification of multiple distinct polymorphic genetic loci using the polymerase chain reaction or other amplification systems to determine, preferentially in one reaction, the alleles of each locus contained within the multiplex system. The invention is thus in the field of chemistry and biology, more particular in molecular biology, more particularly human genetics and most particularly in forensics as well as paternity testing.

BACKGROUND OF THE INVENTION

DNA typing is commonly used to identify the parentage of human children and to confirm the linage of horses, dogs and other animals, and agricultural crops. DNA typing is also commonly employed to identify the source of blood, saliva, semen, and other tissue found at a crime scene or other sites requiring identification of human remains. DNA typing is also employed in clinical settings, for example the therapy of certain leukaemia, to determine success or failure of bone marrow transplantation in presence of particular cancerous tissues. DNA typing involves the analysis of alleles of genomic DNA with characteristics of interest, commonly referred to as "markers". Most typing methods in use today are specifically designed to detect and analyse differences in the length and/or sequence of one or more regions of DNA markers known to appear in at least two different forms in the population. Such length and/or sequence variations are referred to as "polymorphism". Any region, i.e. "locus" of DNA in which such variation occurs is referred to as "polymorphic locus".

When speaking about polymorphic DNA sequences one must distinguish in particular between the so called repeated polymorphic DNA sequences and non-repetitive polymorphic elements. In the study of DNA sequences one can distinguish two main types of repeated sequences; tandem repeats and interspersed repeats. Tandem repeats include satellite DNA. Satellite DNA consist of highly repetitive DNA and is so called because repetitions of short DNA sequence tend to produce different frequency of the nucleotides adenine, cytosine, guanine and thymine and thus, have different density from bulk DNA—such that they form a second or a "satellite" band in genomic DNA separated on a density gradient. A mini-satellite is a section of DNA that consists of short series of bases 10 to 100 bp. These occur in more than 1,000 locations in the human genome. Some mini-satellites contain a central (or core) sequence of letters "GGGCAG-GANG" (where N can be any nucleotide) (N=UPAC code for A, C, G, T) or more generally a strand bias. It has been shown that the sequence per se encourage chromosomes to swap DNA. In alternative models, it is the presence of a neighbouring, cis-acting myotic double-strand break hotspot which is the primary cause of minisatellite repeat copy number variations.

Indispersed repetitive DNA is found in all eukaryotic genomes. These sequences propagate themselves by RNA mediated transposition and they have been called retroposons. Such retroposons are substantially larger than the repetitive elements discussed above.

So-called short indispersed nuclear elements (SINEs) are a further class of repetitive DNA elements. A particular type of SINEs are the so-called ALU-sequences. These are about 300 base pairs in length. Therefore, also these elements are not particularly useful for a simple and straight forward profiling assay.

Microsatellites are simple sequence repeats (SSRs) or also short tandem repeats (STRs) or polymorphic loci present in nuclear DNA and organelle DNA that consist of repeating units of 1 to 6 base pairs in length. They are used as molecular markers which have wide-ranging applications in the field of genetics including kinship and population studies. Microsatellites can also be used to study gene dosage (looking for duplications or deletions of a particular genetic region). One common example of microsatellite is $(CA)_n$ repeat, where n is variable between alleles. These markers are often present in high levels of inter- and intraspecific polymorphism. Particularly when tandem repeats number 10 or greater appear. The repeated sequences often simple, consisting of two, three or four nucleotides (di-, tri-, tetranucleotide repeats respectively) and can be repeated 10 to 100 times. CA nucleotide repeats are very frequent in human and other genomes, and are present every few thousand base pairs. As there are often extremely many alleles present at an STR locus, genotypes within pedigrees are often fully informative and the progenitor of a particular allele can often been identified. However, making use of these so-called STRs in genetic assays has the fundamental effect that due to the large variation within the population one may find in extremely high amount of alleles and said alleles when analyzing these on, e.g. in electrophoretic gel system will differ substantially in size.

When using, e.g. RFLP, the theoretical risk of a coincidental match is 1 in 100 billion (100,000,000,000). However, the rate of laboratory error is almost certainly higher than this, and often actual laboratory procedures do not reflect the theory under which the coincidence probabilities were computed. For example, the coincidence probabilities may be calculated based on the probabilities that markers in two samples have bands in precisely the same location, but a laboratory worker may conclude that similar—but not precisely identical—band patterns result from identical genetic samples with some imperfection in the agarose gel. However, in this case, the laboratory worker increases the coincidence risk by expanding the criteria for declaring a match. STRs have the same problem. This is due to the fact that many alleles exist for each locus and this complexity may lead to ambiguous amplification products which are than incorrectly assigned.

Systems containing several loci are called multiplex systems and many such systems containing up to more than 11 separate STR loci have been developed and are commercially available. Although, amplification protocols with STR loci can be designed which produce small products generally from 60 to 500 base pairs (bp) in length and alleles from each locus are often contained within range of less than 100 base pairs. The substantial drawback with using STR loci is that due to the high variability within the population with respect to particular loci certain alleles may have a high number of repeats and thus, result in large amplification products.

Design of these systems is limited, in part, by the difficulty in separating multiple loci in a single gel or capillary. This occurs, because there is spatial compression of fragments of different sizes, especially longer fragments in gels or capillaries, i.e. commonly used means for separation of DNA fragments by those skilled in the art. Although, the analysis of multi-allelic short tandem repeats (STRs) still has the largest impact on forensic genetics and case work, it must be said, that the systems are limited especially for DNA evidences of low quality and quantity. For example degraded DNA samples represent one of the major challenges of the major STR analysis as amplicon sizes within multiplex assays often exceed 200 base pairs. Degraded samples are extremely difficult to amplify.

At the same time focus has been put on so-called single nucleotide polymorphisms (SNPs), however, these SNPs are difficult to analyze because a given system must be able to identify a single nucleotide polymorphic position.

The present invention represents a significant improvement over existing technology, bringing increased power of discrimination, position and throughput the DNA profiling for linkage analysis, criminal justice, paternity testing and other forensic or medical and genetic identification applications. This is in particular due to the fact that the present invention makes use of a combination of a different type of polymorphic markers, i.e. the so-called frequent biallelic deletion-insertion polymorphisms (DIP).

SUMMARY OF THE INVENTION

The present invention relates to a DNA profiling assay comprising the following steps, providing a sample to be analyzed, providing reagents, enzyme and primer-oligonucleotides which are necessary for simultaneous polymerase chain reaction amplification of at least 20 loci, amplifying the loci, detecting the amplification products, wherein the amplification products and the loci to be amplified are characterized by the following features, each locus to be amplified is characterized by at least one deletion-insertion polymorphism known to be present in the population, wherein the two alleles from each locus differ in size by more than 1 nucleotides and less than 100 nucleotides, a first set of at least two amplification products ranging in size from about 20 nucleotides to about 300 nucleotides stemming from at least two different loci carries a first label, a second set of at least two amplification products ranging in size from about 20 nucleotides to about 300 nucleotides stemming from at least two different loci carries a second label, a third set of at least two amplification products ranging in size from about 20 nucleotides to about 300 nucleotides stemming from at least two different loci carries a third label, label one, label two and label three are each different fluorescent labels which can be differentiated and simultaneously detected by a multi-colour detector in combination with a DNA sequencing device.

It is also an object of the present invention to provide a method, a kit, and primers specific for multiplex amplifications comprising specified loci (DIPs).

Herein, the combined probability of identity (CPI) expresses the likelihood of finding two individuals with the same genotype for a certain set of loci in the population. (Kirst M, Cordeiro C M, Rezende G D, Grattapaglia D. Power of microsatellite markers for fingerprinting and parentage analysis in Eucalyptus grandis breeding populations. J Hered. 2005 96:161-166. PMID: 15601907)

Herein, the CPE/Trio (combined probability of paternity exclusion) expresses the likelihood of excluding a parentage when genotypes of both parents are known for a certain set of loci in the population. (Jamieson A, Taylor SCS (1997) Comparisons of three probability formulae for parentage exclusion. *Animal Genetics,* 28, 397-400.)

Herein, an allelic ladder is a standard size marker consisting of amplified alleles from at least one locus using the same PCR primer which are applied to amplify unknown DNA samples. Each DIP has two alleles.

Herein, an allele is a genetic variation associated with a segment of DNA, i.e., one of two or more alternate forms of a DNA sequence occupying the same locus.

Herein, a DNA polymorphism is a condition in which two or more different nucleotide sequences in a DNA sequence coexist in the same interbreeding population.

Herein, a locus or genetic locus is a specific position on a chromosome.

Herein, alleles of a locus are located at identical sites on homologous chromosomes but differ in their DNA sequences at at least one nucleotide position.

Herein, locus-specific primer is a primer that specifically hybridizes with a portion of the stated locus or its complementary strand, at least for one allele of the locus, and does not hybridize efficiently with other DNA sequences under the conditions used in the amplification method. In general, primer refers to a single stranded DNA oligonucleotide which has typically a length between 10 and 40 (15-35; 18-30) nucleotides and which forms after hybridization with a complementary DNA strand a prolongable substrate complex for a DNA polymerase.

Herein, a profiling assay is a pattern of amplified polymorphic DNA markers which is suitable to differentiate individuals of a species, especially human beings. The method is also referred to as "molecular genetic identification pattern" or "genetic fingerprint".

DETAILED DESCRIPTION OF THE INVENTION

The present invention relates to a DNA profiling assay comprising the following steps, providing a sample to be analyzed, providing reagents, enzyme and primer-oligonucleotides which are necessary for simultaneous polymerase chain reaction amplification of at least 20 loci, amplifying the loci, detecting the amplification products, wherein the amplification products and the loci to be amplified are characterized by the following features, each locus to be amplified is characterized by at least one deletion-insertion polymorphism known to be present in the population, wherein the two alleles from each locus differ in size by more than 1 nucleotides and less than 100 nucleotides, a first set of at least two amplification products ranging in size from about 20 nucleotides to about 300 nucleotides stemming from at least two different loci carries a first label, a second set of at least two amplification products ranging in size from about 20 nucleotides to about 300 nucleotides stemming from at least two different loci carries a second label, a third set of at least two amplification products ranging in size from about 20 nucleotides to about 300 nucleotides stemming from at least two different loci carries a third label, label one, label two and label three are each different fluorescent labels which can be differentiated and simultaneously detected by a multi-colour detector of a DNA sequencing device the size difference between two alleles for a given locus is larger than 1 nucleotides and smaller than 100 nucleotides. Ideally, the size difference is larger than 2 and smaller than 80, smaller than 60, smaller than 40, smaller than 30 or smaller than 20 nucleotides. Larger than 3 and smaller than 20 nucleotides is preferred. As can be seen from the experiments performed this size range has unexpected advantages and enables a large multiplex.

The inventors have found that the assay gives significantly better results when a sample is used that comprises degraded DNA, partially degraded DNA, very little DNA, or e.g. inhibitors of the PCR.

The sample to be analyzed may be one of many things, such as isolated DNA, cells, saliva, urine or blood. Other tissues are likewise encompassed.

The DNA may be from human, cat, dog or any other animal.

An "isolated DNA" is either (1) a DNA that contains sequence not identical to that of any naturally occurring sequence, or (2), in the context of a DNA with a naturally-occurring sequence (e.g., a cDNA or genomic DNA), a DNA free of at least one of the genes that flank the gene containing the DNA of interest in the genome of the organism in which the gene containing the DNA of interest naturally occurs. The term therefore includes a recombinant DNA incorporated into a vector, into an autonomously replicating plasmid or virus, or into the genomic DNA of a prokaryote or eukaryote. The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein, mutein, or fragment of a given protein; and a nucleic acid which is a degenerate variant of a cDNA or a naturally occurring nucleic acid. In addition, it includes a recombinant nucleotide sequence that is part of a hybrid gene, i.e., a gene encoding a non-naturally occurring fusion protein. It will be apparent from the foregoing that isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice.

A PCR reaction may consist of 10 to 45 "cycles" of denaturation and synthesis of a DNA molecule. Such methods include, but are not limited to, PCR (as described in U.S. Pat. Nos. 4,683,195 and 4,683,202, which are hereby incorporated by reference), Strand Displacement Amplification ("SDA") (as described in U.S. Pat. No. 5,455,166, which is hereby incorporated by reference), and Nucleic Acid Sequence-Based Amplification ("NASBA") (as described in U.S. Pat. No. 5,409,818, which is hereby incorporated by reference). For example, amplification may be achieved by a rolling circle replication system which may even use a helicase for enhanced efficiency in DNA melting with reduced heat (see Yuzhakou et al., Cell 86:877-886 (1996) and Mok et al., J. Biol. Chem. 262:16558-16565 (1987), which are hereby incorporated by reference).

In a preferred embodiment, the temperature at which denaturation is done in a thermocycling amplification reaction is between about 90° C. to greater than 95° C., more preferably between 92-94° C. Preferred thermocycling amplification methods include polymerase chain reactions involving from about 10 to about 100 cycles, more preferably from about 25 to about 50 cycles, and peak temperatures of from about 90° C. to greater than 95° C., more preferably 92-94° C.

In a preferred embodiment, a PCR reaction is done using a DNA Polymerase I to produce, in exponential quantities relative to the number of reaction steps involved, at least one target nucleic acid sequence, given (a) that the ends of the target sequence are known in sufficient detail that oligonucleotide primers can be synthesized which will hybridize to them and (b) that a small amount of the target sequence is available to initiate the chain reaction. The product of the chain reaction will be a discrete nucleic acid duplex with termini corresponding to the ends of the specific primers employed.

Any source of nucleic acid, in purified or non-purified form, can be utilized as the starting nucleic acid, if it contains or is thought to contain the target nucleic acid sequence desired. Thus, the process may employ, for example, DNA which may be single stranded or double stranded. In addition, a DNA-RNA hybrid which contains one strand of each may be utilized. A mixture of any of these nucleic acids may also be employed, or the nucleic acids produced from a previous amplification reaction using the same or different primers may be so utilized. The nucleic acid amplified is preferably DNA. The target nucleic acid sequence to be amplified may be only a fraction of a larger molecule or can be present initially as a discrete molecule, so that the target sequence constitutes the entire nucleic acid. It is not necessary that the target sequence to be amplified be present initially in a pure form; it may be a minor fraction of a complex mixture or a portion of nucleic acid sequence due to a particular animal which organism might constitute only a very minor fraction of a particular biological sample. The starting nucleic acid may contain more than one desired target nucleic acid sequence which may be the same or different. Therefore, the method is useful not only for producing large amounts of one target nucleic acid sequence, but also for amplifying simultaneously multiple target nucleic acid sequences located on the same or different nucleic acid molecules. This is particularly the case if and when human DNA is amplified in the background of DNA from animals. That may happen at some crime scenes.

The nucleic acid(s) may be obtained from any source and include plasmids and cloned DNA, DNA from any source, including bacteria, yeast, viruses, and higher organisms such as plants or animals. DNA may be extracted from, for example, blood or other fluid, or tissue material such as corionic villi or amniotic cells by a variety of techniques such as that described by Sambrook J, Fritsche E F, Maniatis T. Molecular cloning. A laboratory manual. $2^{nd}$ edition, Cold Spring Harbor Laboratory Press (1989).

The assay makes use of locus-specific primers. The primers are arranged upstream and downstream of the DIP. The primers are ideally about equidistant but are placed such that mispairing is reduced and an ideal melting temperature is achieved. Preferred primers have a length of from about 15-100, more preferably about 20-50, most preferably about 20-40 bases. It is essential that the primers of the method span the region comprising the DIP (deletion-insertion-polymorphism). Especially, the inventers found for highly multiplexed PCR with more than 20 loci, that the annealing temperature of the primers should be between 56-65° C., more preferable between 57-63° C. and most preferable between 59-61° C. In addition, the difference between annealing temperatures of the forward and the reverse primer of one locus specific primer pair as well as between all primers of the multiplex PCR mixture should be less than 4 C. All primers should give assay specific PCRs, e.g. should be human specific in the case of a human forensic or diagnostic multiplex applications. The locus specific primer pairs as well as all primers within the multiplex reaction mixture should not give unspecific side products within PCR or multiplex-PCR. Furthermore, it is very important to avoid DNA sequence self complementarity between all primers of the multiplex reaction mixture to prevent autodimer or heterodimer formations within the PCR or multiplex-PCR.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

The target nucleic acid sequence is amplified by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° C. to 105° C., preferably about 90° C. to about 98° C., still more preferably 93° C. to 95° C., for times ranging from about 1 to 10 minutes. Strand separation may also be induced by an enzyme from the class of enzymes known as helicases or the enzyme RecA, which has helicase activity and is known to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), and techniques for using RecA are reviewed in C. Radding, Ann. Rev. Genetics, 16:405-37 (1982), which is hereby incorporated by reference.

Synthesis can be performed using any suitable method. Generally, it occurs in a buffered aqueous solution. In some preferred embodiments, the buffer pH is about 7.5-9.2 (adjusted at room temperature). Preferably, a molar excess (for cloned nucleic acid, usually about 1000:1 primer:template, and for genomic nucleic acid, usually about $10^6$:1 primer:template) of the two oligonucleotide primers is added to the buffer containing the separated template strands. It is understood, however, that the amount of complementary strand may not be known if the process herein is used for some applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process. Preferred reaction conditions for a PCR are as follows: 20 mM Tris/HCl-buffer (pH 8.8; adjusted at room temperature), 200 µM (40-500 µM) dNTPs, 1-10 (1-4) mM MgCl$_2$, 50 mM KCl, 0.05-2 µM of each oligonucleotide primer, 0.05-0.5% (vol./vol.) Tween 20 and 1-2.5 units Taq DNA polymerase. In some embodiments (analysis of forensic stains, single cells or low copy number (LCN) DNA) Taq DNA polymerases with so called "hot start technology" (U.S. Pat. Nos. 5,587,287; 5,677,152; 6,214,557; 6,183,967) are preferred to avoid non-specific amplification. Furthermore, genetically engineered Taq DNA polymerases which lack 5'→3' exonuclease activity (e.g. EU Pat. No. 0553264, EU Pat. No. 1507002, EU Pat. No. 0395736, EU Pat. No. 0983364) are advantageous in certain applications. The detergent Tween 20 can be replaced by Nonidet P-40 [0.05-0.5% (vol./vol.)] or Triton X-100 [0.05-0.5% (vol./vol.)] or mixtures of these detergents are applied (e.g. Tween 20 together with Nonidet P-40). The monovalent cation K$^+$ can be replaced by NH$_4^+$ (1-20 mM final concentration) or mixtures of both cations are used. Sometimes anions other than chloride like sulfate or acetate are preferred. To persons skilled in the art further additives are known as stabilizers of the DNA polymerase and/or PCR enhancers. Examples of these substances are betain (0.1-2.0 M), trehalose (0.02-2.0 M), sorbitol (0.02-2.0 M, dimethylsulfoxid (up 5% vol./vol.) or tetramethylammoniumchloride (up to 5% vol./vol.). In addition sometimes 200-2000 mg/mL bovine serum albumin (BSA) or gelatine is applied to neutralize the effect of PCR inhibitors derived from impure DNA sample preparations.

Nucleoside triphosphates, preferably dATP, dCTP, dGTP, dTTP and/or dUTP are also added to the synthesis mixture in adequate amounts. The preferred molarity of nucleotides is 40-500 µM, in particular 100-250 µM. While such dNTP concentrations are amenable to the methods of the invention, concentrations higher than 500 µM may be advantageous in some embodiments.

It is preferred that the polymerase according to the invention is selected from the group of genera of *Thermus, Aquifex, Thermotoga, Thermocridis, Hydrogenobacter, Thermosynchecoccus* and *Thermoanaerobacter*.

It is preferred that the polymerase according to the invention is selected from the group of organisms of *Aquifex aeolicus, Aquifex pyogenes, Thermus thermophilus, Thermus aquaticus, Thermotoga neapolitana, Thermus pacificus* and *Thermotoga maritima*.

DNA polymerase I is an enzyme that mediates the process of DNA replication in prokaryotes. Pol I was the first enzyme discovered with polymerase activity, and it is the best characterized enzyme. Although this was the first enzyme to be discovered that had the required polymerase activities, it is not the primary enzyme involved with bacterial DNA replication. Discovered by Arthur Kornberg in 1956, it was the first known DNA polymerase, and was initially characterized in *E. coli*, although it is ubiquitous in prokaryotes. It is often referred to as simply Pool I. In *E. coli* and many other bacteria, the gene which encodes Pol I is known as pol-A. In the present invention it is preferred that the enzyme is a pol-A type polymerase.

It is most preferred that the polymerase is Taq DNA polymerase.

In one embodiment uracil residues are incorporated during the PCR reaction. Uracil DNA glycosylase (uracil-N-glycosylase) is the product of the *Escherichia coli* ung gene, and has been cloned, sequenced and expressed in *E. coli*. Uracil DNA glycosylase (UDG) removes these uracil residues from DNA (single- and double-stranded) without destroying the DNA sugar-phosphodiester backbone, thus preventing its use as a hybridization target or as a template for DNA polymerases.

The resulting abasic sites are susceptible to hydrolytic cleavage at elevated temperatures. Thus, removal of uracil bases is usually accompanied by fragmentation of the DNA. A person skilled in the art knows how to use the Uracil DNA glycosylase in order to avoid contamination. Likewise both the enzyme as well as the uracil nucleotide may be in the inventive kit.

In a preferred embodiment at least 25 loci are amplified simultaneously.

In another embodiment the inventive DIP loci (SEQ IDs disclosed herein) can be amplified and genotyped using allele specific multiplex PCR (U.S. Pat. No. 5,595,890; Newton C R, Graham A, Heptinstall L E, Powell S J, Summers C, Kalsheker N, Smith J C, Markham A F. Analysis of any point mutation in DNA. The amplification refractory mutation system (ARMS). Nucleic Acids Res 17: 2503-2516, 1989). In this case three primers are used for each locus, one locus-specific and two allele-specific. The 3'-ends of the allele-specific primers are located within the DIP sequence in a manner that allele-specific extension products are synthesized by DNA polymerases. Thus, in the case of a heterozygous DNA two different amplicons are produced together with the locus specific primer in one PCR. If the two allele specific amplicons can be electrophoretically distinguished by their size one labelled primer (the locus specific) can be used. If this is not the case one of the allele specific primers can be extended at its 5'-end by an artificial tailing sequence (5'-tailing with nucleotides or mobility modifier) or the two allele specific primers are labelled at their 5'-ends with two different fluorophores.

In a particularly preferred embodiment at least 30 loci are amplified simultaneously.

In a further preferred embodiment at least 40 loci are amplified simultaneously.

In a further preferred embodiment at least 50 loci are amplified simultaneously.

In a particularly preferred embodiment of the profiling assay according to the invention the three sets of amplification products comprise at least six amplification products. For the first time the inventors have demonstrated that it is possible to do a reaction with 30 amplification products, wherein at least three colours are used as label of PCR primers. The inventors have identified this ideal distribution which allows for detection on multiple devices while at the same time allowing for a high a combined probability of identity (CPI).

The inventors have found that this enable the additional use of the fourth colour frequently present in sequencing devices for controls and/or ladders of varying type.

Thus, the surprising fact that it is possible that the at least three sets of amplification products may comprise at least ten amplification products for the first time allows for the use of DIPs in a number sufficiently high to enable a high combined probability of identity (CPI) score at the same time allowing for an extra control lane/dye/label. This makes the use of STRs unnecessary.

The inventors have tested the system using sample from the German population. The system has a combined probability of identity (CPI) of $2.1 \times 10^{-13}$. This is an excellent value an is better than the AmpFISTR Minifilier kit which makes use of 8 STRs (CPI of $8.21 \times 10^{-11}$).

Further the inventors can show the 30 DIPs according to the invention have a CPE/Trio (combined probability of paternity exclusion) of 0,9979205.

Thus in one embodiment of the profiling assay according to the invention the three sets a) to c) of amplification products comprises at least ten amplification products and these display a combined probability of identity (CPI) of $2.1 \times 10^{-13}$ or better and/or a CPE/Trio (combined probability of paternity exclusion) of 0,9979205 or better.

It is preferred that the two alleles from each locus differ in size by more than 1 nucleotides and less than 40 nucleotides.

It is preferred that the two or more amplification products ranging in size from about 20 nucleotides to about 300 nucleotides stemming from at least two different loci carry a fourth label. Likewise of course in a further embodiment 5, 6, 7, or more labels may be used. Four labels are preferred because due to the nucleotide content of DNA most DNA sequencing devices which may used to detect the product are able to detect 4 labels.

The label is preferably a fluorescent dye. Such a dye may be selected from the following group comprising fluorescein-isothiocyanate (FITC), 6-carboxyfluorescein (6-FAM), xanthen, rhodamine, 6-carboxy-2',4',7',4,7-hexachlorofluorescein (HEX), 6-carboxy-4',5'-dichloro-2',7'-dimethodyfluorescein (JOE), N,N,N',N'-tetramethyl-6-carboxyrhodamine (TAMRA), 6-carboxy-X-rhodamine (ROX), 5-carboxyrhodamine-6G (R6G5), 2'-chloro-7'phenyl-1,4-dichloro-6-carboxyfluorescein (VIC), 2'-chloro-5'-fluoro-7',8'-benzo-1,4-dichloro-6-carboxyfluorescein (NED) or PET (proprietary of Applied Biosystems, Foster City, Calif., USA), 6-carboxyrhodamine-6G (RG6), rhodamine 110; coumarine, texas red, Cy3, Cy5, Cy7 and BODIPY dyes.

A preferred combination is, 6-FAM (blue), VIC (green), NED (yellow) when using three colours for labelling PCR oligonucleotides and ROX (red) for the internal length standard. And, optionally, 6-FAM (blue), VIC (green), NED (yellow) and PET (red) are used as PCR primer labels in combination with a LIZ (orange) labelled internal length standard. Table 1 lists further preferred combinations of dye labels used for multiplex PCR in combination with sequencing automates of Applied Biosystems (Foster City, Calif., USA). It should be mentioned that other multi-colour sequencing automates like the CEQ™ 8000 Genetic Analyzer series (Beckmann Coulter, Fullerton, Calif., USA), the MEGABace™ Genotyping System series (GE Healthcare, Buckinghamshire, UK) or the LI-CORE 4300 DNA Analysis System (LI-CORE Biosciences UK, Cambridge, UK) exist or may arise which possess other optical systems and, thus, require other fluorescent dyes and dye combinations. Consequently, embodiments of the present invention which utilize combinations of other fluorophores and are dedicated to other sequencing automates are anytime possible.

U.S. Pat. Nos. 6,734,296, 5,624,800 and WO 2006071568 (which are hereby incorporated by reference) disclose the use of so-called mobility modifiers to increase the degree of multiplexing for subsequent genotyping by capillary gel electrophoresis. Mobility modifiers are defined as covalent non-nucleotide modifications of the 5'-end of primers which decrease the electrophoretic mobility of DNA amplification products, primer extension products or oligo-ligase products. This technology allows to separate DNA fragments from a plurality of amplification products with the same number of nucleotides. In a preferred embodiment different numbers (n=1, 2, 3, . . . ) of hexaethylenglycol moieties are synthesized via standard phosphoramidite chemistry between the 5'-end of the oligonucleotide and the fluorescent label of subsets of the multiplex primers (Grossman P D, Bloch W, Brinson E, Chang C C, Eggerding F A, Fung S, Iovannisci, D M, Woo S, Winn-Deen E S. High-density multiplex detection of nucleic acid sequences: oligonucleotide ligation assay and sequence-coded separation. Nucleic Acids Res 22: 4527-34, 1994).

TABLE 1

Combinations of fluorescent dyes which are compatible with sequencing devices from Applied Biosystems. The abbreviations for the dyes are explained in the text.

| No. of colours | blue | Green | yellow | red | orange |
|---|---|---|---|---|---|
| 4 | 6-FAM | HEX | NED | ROX | |
| 4 | 6-FAM | VIC | NED | ROX | |
| 4 | 6-FAM | TET | HEX | TAMRA | |
| 4 | 6-FAM | JOE | NED | ROX | |

TABLE 1-continued

Combinations of fluorescent dyes which are compatible with sequencing devices from Applied Biosystems. The abbreviations for the dyes are explained in the text.

| No. of colours | blue | Green | yellow | red | orange |
|---|---|---|---|---|---|
| 5 | 6-FAM | VIC | NED | PET | LIZ |
| 5 | 6-FAM | HEX | NED | PET | LIZ |
| 4 | 5/6-FAM | JOE | TMR | ROX | |

In one embodiment the detection step is carried out with a capillary gel electrophoresis device. The detection step may also be carried out on a gel based device.

Following the construction of allelic ladders for individual loci, these may be mixed and loaded for gel electrophoresis at the same time as the loading of amplified samples occurs. Each allelic ladder co-migrates with alleles in the sample from the corresponding locus. The products of the multiplex reactions of the present invention can be evaluated using an internal lane standard, a specialized type of size marker configured to run in the same lane of a polyacrylamide gel or same capillary. The internal lane standard preferably consists of a series of fragments of known length.

The internal lane standard more preferably is labeled with a fluorescent dye which is distinguishable from other dyes in the amplification reaction.

The invention also relates to the use of the DIPs disclosed herein for making an allelic ladder.

Following construction of the internal lane standard, this standard can also be mixed with amplified sample or allelic ladders and loaded for electrophoresis for comparison of migration in different lanes of gel electrophoresis or different capillaries of capillary electrophoresis. Variation in the migration of the internal lane standard indicates variation in the performance of the separation medium. Quantitation of this difference and correlation with the allelic ladders allows correction in the size determination of alleles in unknown samples.

In a further embodiment additionally one or more short tandem repeat sequences (STR) are amplified and/or one or more variable number tandem repeat sequences (VNTR) are amplified and/or one or more single nucleotide polymorphisms (SNP) are amplified. Thus, according to these embodiments the DIPs may be mixed with other polymorphic sequences. STR sequences are preferred.

Often it is important to be able to determine the sex of an individual. Thus, in one embodiment of the profiling assay of any of the previous claims, wherein additionally one or more non recombining invariant X- and/or Y-chromosomal DNA sequences, sex specific short tandem repeat sequences (STR) and/or one or more sex specific variable number tandem repeat sequences (VNTR) are amplified and/or one or more sex specific single nucleotide polymorphisms (SNP) are amplified. A preferred locus is the amelogenin locus of which two paralog copies, AmelX and AmelY, exist which are located within the non recombining regions of the human gonosomes (Akane A. Sex determination by PCR analysis of the X-Y amelogenin gene. Methods Mol Biol, Vol 98, pp 245-249, 1998). Parts of intron 1 of the genes for amelogenin encode DIPs which can be used in sex determination of samples from unknown human origin through the Polymerase Chain Reaction (PCR). For example DNA SEQ ID NO. 61 and SEQ ID NO. 62 are AmelX and AmelY sequences, respectively, which encode a 6 by DIP (−/AAAGTG). Using the primers SEQ ID NO. 185 and SEQ ID NO. 186 a 113 bp fragment of the X-chromosome and a 119 bp Y-chromosome can be amplified and electrophoretically separated. Likewise DNA SEQ ID NO. 63 and SEQ ID NO. 64 are AmelX and AmelY sequences, respectively, which encode a 3 bp DIP (−/GAT). Using the primers SEQ ID NO. 187 and SEQ ID NO. 188 a 83 bp fragment of the X-chromosome and a 86 bp Y-chromosome can be amplified and electrophoretically separated.

The primer pairs for the method according to the invention must fulfil certain criteria. The must hybridize specifically to the desired location. False annealing is very bad for the reaction. A Ta of 50°-68° C. preferred a Ta of 56-65° C. or 57-63° C. are even more and 59-61° C. is most preferred. A GC content of 20-60% GC is preferred. A length of 18-30 by is preferred. Maximal self complementarity of primers and maximal complimentary between all primers in the multiplex-PCR of 3-7 bp is preferred. Furthermore, the selection of appropriate primers for highly multiplexed PCRs always needs empirical optimization to avoid unspecific side products.

In a very preferred embodiment of the profiling assay according to the invention the primer-oligonucleotide pairs are selected from the group of nucleic acid molecules with the following sequences:

a) DIP NO. 1: SEQ ID NO. 125 and SEQ ID NO. 126 or SEQ ID NO. 267 and SEQ ID NO. 268
b) DIP NO. 2: SEQ ID NO. 127 and SEQ ID NO. 128
c) DIP NO. 3: SEQ ID NO. 129 and SEQ ID NO. 130
d) DIP NO. 4: SEQ ID NO. 131 and SEQ ID NO. 132
e) DIP NO. 5: SEQ ID NO. 133 and SEQ ID NO. 134
f) DIP NO. 6: SEQ ID NO. 135 and SEQ ID NO. 136
g) DIP NO. 7: SEQ ID NO. 137 and SEQ ID NO. 138
h) DIP NO. 8: SEQ ID NO. 139 and SEQ ID NO. 140 or SEQ ID NO. 287 and SEQ ID NO. 288
i) DIP NO. 9: SEQ ID NO. 141 and SEQ ID NO. 142
j) DIP NO. 10: SEQ ID NO. 143 and SEQ ID NO. 144
k) DIP NO. 11: SEQ ID NO. 145 and SEQ ID NO. 146
l) DIP NO. 12: SEQ ID NO. 147 and SEQ ID NO. 148
m) DIP NO. 13: SEQ ID NO. 149 and SEQ ID NO. 150
n) DIP NO. 14: SEQ ID NO. 151 and SEQ ID NO. 152
o) DIP NO. 15: SEQ ID NO. 153 and SEQ ID NO. 154 or SEQ ID NO. 281 and SEQ ID NO. 282
p) DIP NO. 16: SEQ ID NO. 155 and SEQ ID NO. 156
q) DIP NO. 17: SEQ ID NO. 157 and SEQ ID NO. 158 or SEQ ID NO. 273 and SEQ ID NO. 274
r) DIP NO. 18: SEQ ID NO. 159 and SEQ ID NO. 160 or SEQ ID NO. 277 and SEQ ID NO. 278
s) DIP NO. 19: SEQ ID NO. 161 and SEQ ID NO. 162 or SEQ ID NO. 279 and SEQ ID NO. 280
t) DIP NO. 20: SEQ ID NO. 163 and SEQ ID NO. 164 or SEQ ID NO. 275 and SEQ ID NO. 276
u) DIP NO. 21: SEQ ID NO. 165 and SEQ ID NO. 166
v) DIP NO. 22: SEQ ID NO. 167 and SEQ ID NO. 168
w) DIP NO. 23: SEQ ID NO. 169 and SEQ ID NO. 170
x) DIP NO. 24: SEQ ID NO. 171 and SEQ ID NO. 172
y) DIP NO. 25: SEQ ID NO. 173 and SEQ ID NO. 174
z) DIP NO. 26: SEQ ID NO. 175 and SEQ ID NO. 176
aa) DIP NO. 27: SEQ ID NO. 177 and SEQ ID NO. 178
ab) DIP NO. 28: SEQ ID NO. 179 and SEQ ID NO. 180
ac) DIP NO. 29: SEQ ID NO. 181 and SEQ ID NO. 182 or SEQ ID NO. 271 and SEQ ID NO. 272
ad) DIP NO. 30: SEQ ID NO. 183 and SEQ ID NO. 184 or SEQ ID NO. 283 and SEQ ID NO. 284
ae) DIP NO. 31: SEQ ID NO. 185 and SEQ ID NO. 186
af) DIP NO. 32: SEQ ID NO. 187 and SEQ ID NO. 188 or SEQ ID NO. 269 and SEQ ID NO. 270
ag) DIP NO. 33: SEQ ID NO. 189 and SEQ ID NO. 190 or SEQ ID NO. 285 and SEQ ID NO. 286 ah) DIP NO. 34: SEQ ID NO. 191 and SEQ ID NO. 191
ai) DIP NO. 35: SEQ ID NO. 193 and SEQ ID NO. 194
aj) DIP NO. 36: SEQ ID NO. 195 and SEQ ID NO. 196
ak) DIP NO. 37: SEQ ID NO. 197 and SEQ ID NO. 198
al) DIP NO. 38: SEQ ID NO. 199 and SEQ ID NO. 200
am) DIP NO. 39: SEQ ID NO. 201 and SEQ ID NO. 202
an) DIP NO. 40: SEQ ID NO. 203 and SEQ ID NO. 204
ao) DIP NO. 41: SEQ ID NO. 205 and SEQ ID NO. 206 or SEQ ID NO. 251 and SEQ ID NO. 252
ap) DIP NO. 42: SEQ ID NO. 207 and SEQ ID NO. 208 or SEQ ID NO. 253 and SEQ ID NO. 254
aq) DIP NO. 43: SEQ ID NO. 209 and SEQ ID NO. 210 or SEQ ID NO. 255 and SEQ ID NO. 256
ar) DIP NO. 44: SEQ ID NO. 211 and SEQ ID NO. 212 or SEQ ID NO. 257 and SEQ ID NO. 258
as) DIP NO. 45: SEQ ID NO. 213 and SEQ ID NO. 214 or SEQ ID NO. 259 and SEQ ID NO. 260
at) DIP NO. 46: SEQ ID NO. 215 and SEQ ID NO. 216 or SEQ ID NO. 261 and SEQ ID NO. 262
au) DIP NO. 47: SEQ ID NO. 217 and SEQ ID NO. 218 or SEQ ID NO. 263 and SEQ ID NO. 264
av) DIP NO. 48: SEQ ID NO. 219 and SEQ ID NO. 220
aw) DIP NO. 49: SEQ ID NO. 221 and SEQ ID NO. 222
ax) DIP NO. 50: SEQ ID NO. 223 and SEQ ID NO. 224
ay) DIP NO. 51: SEQ ID NO. 225 and SEQ ID NO. 226 or SEQ ID NO. 265 and SEQ ID NO. 266
az) DIP NO. 52: SEQ ID NO. 227 and SEQ ID NO. 228
ba) DIP NO. 53: SEQ ID NO. 229 and SEQ ID NO. 230
bb) DIP NO. 54: SEQ ID NO. 231 and SEQ ID NO. 232
bc) DIP NO. 55: SEQ ID NO. 233 and SEQ ID NO. 234
bd) DIP NO. 56: SEQ ID NO. 235 and SEQ ID NO. 236
be) DIP NO. 57: SEQ ID NO. 237 and SEQ ID NO. 238
bf) DIP NO. 58: SEQ ID NO. 239 and SEQ ID NO. 240
bg) DIP NO. 59: SEQ ID NO. 241 and SEQ ID NO. 242
bh) DIP NO. 60: SEQ ID NO. 243 and SEQ ID NO. 244
bi) DIP NO. 61: SEQ ID NO. 245 and SEQ ID NO. 246
bj) DIP NO. 62: SEQ ID NO. 247 and SEQ ID NO. 248
bk) DIP NO. 63: SEQ ID NO. 249 and SEQ ID NO. 250

Preferably at least 4, 5, 6, 7, 8, 9, 10, 11, 12, 13, 14, 15, 16, 17, 18, 19, 20, 21, 22, 23, 24, 25, 26, 27 or more than 30 pairs are selected.

The invention relates to a kit for use in a DNA profiling method comprising at least 3, 4, 5, 6, 7, 8, 9, 10, 11, 12, 13, 14, 15, 16, 17, 18, 19, 20, 21, 22, 23, 24, 25, 26, 27, 28, 29, 30, or more primer pairs for polymerase chain reaction amplification, wherein the primer pairs, consisting of each one up-stream and one down-stream primer, are able to bind a specific DIP sequence according to any one of the sequences selected from the group of, DIP NO. 1:
 SEQ ID NO. 1 wherein the deletion-insertion polymorphism is between nucleotide No. 251 and No. 252,
 SEQ ID NO. 2 wherein the deletion-insertion polymorphism is between nucleotide No. 251 and No. 256,
DIP NO. 2:
 SEQ ID NO. 3 wherein the deletion-insertion polymorphism is between nucleotide No. 250 and No. 251,
 SEQ ID NO. 4 wherein the deletion-insertion polymorphism is between nucleotide No. 250 and No. 255,
DIP NO. 3:
 SEQ ID NO. 5 wherein the deletion-insertion polymorphism is between nucleotide No. 251 and No. 252,
 SEQ ID NO. 6 wherein the deletion-insertion polymorphism is between nucleotide No. 251 and. No. 256,
DIP NO. 4:
 SEQ ID NO. 7 wherein the deletion-insertion polymorphism is between nucleotide No. 250 and No. 251,
 SEQ ID NO. 8 wherein the deletion-insertion polymorphism is between nucleotide No. 250 and No. 262,
DIP NO. 5:
 SEQ ID NO. 9 wherein the deletion-insertion polymorphism is between nucleotide No. 251 and No. 252,
 SEQ ID NO. 10 wherein the deletion-insertion polymorphism is between nucleotide No. 251 and No. 256,
DIP NO. 6:
 SEQ ID NO. 11 wherein the deletion-insertion polymorphism is between nucleotide No. 251 and No. 252,
 SEQ ID NO. 12 wherein the deletion-insertion polymorphism is between nucleotide No. 251 and No. 256,
DIP NO. 7:
 SEQ ID NO. 13 wherein the deletion-insertion polymorphism is between nucleotide No. 251 and No. 252,
 SEQ ID NO. 14 wherein the deletion-insertion polymorphism is between nucleotide No. 251 and No. 256,
DIP NO. 8:
 SEQ ID NO. 15 wherein the deletion-insertion polymorphism is between nucleotide No.251 and No. 252,
 SEQ ID NO. 16 wherein the deletion-insertion polymorphism is between nucleotide No. 251 and No. 256,
DIP NO. 9:
 SEQ ID NO. 17 wherein the deletion-insertion polymorphism is between nucleotide No. 251 and No. 252,
 SEQ ID NO. 18 wherein the deletion-insertion polymorphism is between nucleotide No. 251 and No. 257,
DIP NO. 10:
 SEQ ID NO. 19 wherein the deletion-insertion polymorphism is between nucleotide No. 246 and No. 247,
 SEQ ID NO. 20 wherein the deletion-insertion polymorphism is between nucleotide No. 246 and No. 252,
DIP NO. 11:
 SEQ ID NO. 21 wherein the deletion-insertion polymorphism is between nucleotide No. 251 and No. 252,
 SEQ ID NO. 22 wherein the deletion-insertion polymorphism is between nucleotide No. 251 and No. 256,
DIP NO. 12:
 SEQ ID NO. 23 wherein the deletion-insertion polymorphism is between nucleotide No. 250 and No. 251,
 SEQ ID NO. 24 wherein the deletion-insertion polymorphism is between nucleotide No. 250 and No. 260,
DIP NO. 13:
 SEQ ID NO. 25 wherein the deletion-insertion polymorphism is between nucleotide No. 251 and No. 252,
 SEQ ID NO. 26 wherein the deletion-insertion polymorphism is between nucleotide No. 251 and No. 256,
DIP NO. 14:
 SEQ ID NO. 27 wherein the deletion-insertion polymorphism is between nucleotide No. 251 and No. 252,
 SEQ ID NO. 28 wherein the deletion-insertion polymorphism is between nucleotide No. 251 and No. 260,
DIP NO. 15:
 SEQ ID NO. 29 wherein the deletion-insertion polymorphism is between nucleotide No. 251 and No. 252,
 SEQ ID NO. 30 wherein the deletion-insertion polymorphism is between nucleotide No. 251 and No. 263,
DIP NO. 16:
 SEQ ID NO. 31 wherein the deletion-insertion polymorphism is between nucleotide No. 251 and No. 252,
 SEQ ID NO. 32 wherein the deletion-insertion polymorphism is between nucleotide No. 251 and No. 256,
DIP NO: 17:
 SEQ ID NO. 33 wherein the deletion-insertion polymorphism is between nucleotide No. 251 and No. 252,
 SEQ ID NO. 34 wherein the deletion-insertion polymorphism is between nucleotide No. 251 and No. 270, DIP NO. 18:
- SEQ ID NO. 35 wherein the insertion-deletion polymorphism is between nucleotide No. 251 and No. 252,
- SEQ ID NO. 36 wherein the insertion-deletion polymorphism is between nucleotide No. 251 and No. 263, DIP NO. 19:
- SEQ ID NO. 37 wherein the deletion-insertion polymorphism is between nucleotide No. 251 and No. 252,
- SEQ ID NO. 38 wherein the deletion-insertion polymorphism is between nucleotide No. 251 and No. 257, DIP NO. 20:
- SEQ ID NO. 39 wherein the deletion-insertion polymorphism is between nucleotide No. 251 and No. 252,
- SEQ ID NO. 40 wherein the deletion-insertion polymorphism is between nucleotide No. 251 and No. 257, DIP NO. 21:
- SEQ ID NO. 41 wherein the deletion-insertion polymorphism is between nucleotide No. 251 and No. 252,
- SEQ ID NO. 42 wherein the deletion-insertion polymorphism is between nucleotide No. 251 and No. 258, DIP NO. 22:
- SEQ ID NO. 43 wherein the deletion-insertion polymorphism is between nucleotide No. 250 and No. 251,
- SEQ ID NO. 44 wherein the deletion-insertion polymorphism is between nucleotide No. 250 and No. 257, DIP NO. 23:
- SEQ ID NO. 45 wherein the deletion-insertion polymorphism is between nucleotide No. 251 and No. 252,
- SEQ ID NO. 46 wherein the deletion-insertion polymorphism is between nucleotide No. 251 and No. 257, DIP NO. 24:
- SEQ ID NO. 47 wherein the deletion-insertion polymorphism is between nucleotide No. 251 and No. 252,
- SEQ ID NO. 48 wherein the deletion-insertion polymorphism is between nucleotide No. 251 and No. 263, DIP NO. 25:
- SEQ ID NO. 49 wherein the deletion-insertion polymorphism is between nucleotide No. 250 and No. 251,
- SEQ ID NO. 50 wherein the deletion-insertion polymorphism is between nucleotide No. 250 and No. 296, DIP NO. 26:
- SEQ ID NO. 51 wherein the deletion-insertion polymorphism is between nucleotide No. 251 and No. 252,
- SEQ ID NO. 52 wherein the deletion-insertion polymorphism is between nucleotide No. 251 and No. 266, DIP NO. 27:
- SEQ ID NO. 53 wherein the deletion-insertion polymorphism is between nucleotide No. 250 and No. 251,
- SEQ ID NO. 54 wherein the deletion-insertion polymorphism is between nucleotide No. 250 and No. 273, DIP NO. 28:
- SEQ ID NO. 55 wherein the deletion-insertion polymorphism is between nucleotide No. 251 and No. 252,
- SEQ ID NO. 56 wherein the deletion-insertion polymorphism is between nucleotide No. 251 and No. 260, DIP NO. 29:
- SEQ ID NO. 57 wherein the deletion-insertion polymorphism is between nucleotide No. 251 and No. 252,
- SEQ ID NO. 58 wherein the deletion-insertion polymorphism is between nucleotide No. 251 and No. 267, DIP NO. 30:
- SEQ ID NO. 59 wherein the deletion-insertion polymorphism is between nucleotide No. 251 and No. 252,
- SEQ ID NO. 60 wherein the deletion-insertion polymorphism is between nucleotide No. 251 and No. 270, DIP NO. 31:
- SEQ ID NO. 61 wherein the deletion-insertion polymorphism is between nucleotide No. 271 and No. 272,
- SEQ ID NO. 62 wherein the deletion-insertion polymorphism is between nucleotide No. 271 and No. 278, DIP NO. 32:
- SEQ ID NO. 63 wherein the deletion-insertion polymorphism is between nucleotide No. 280 and No. 281,
- SEQ ID NO. 64 wherein the deletion-insertion polymorphism is between nucleotide No. 280 and No. 284, DIP NO. 33:
- SEQ ID NO. 65 wherein the deletion-insertion polymorphism is between nucleotide No. 250 and No. 251,
- SEQ ID NO. 66 wherein the deletion-insertion polymorphism is between nucleotide No. 250 and No. 256, DIP NO. 34:
- SEQ ID NO. 67 wherein the deletion-insertion polymorphism is between nucleotide No. 251 and No. 252,
- SEQ ID NO. 68 wherein the deletion-insertion polymorphism is between nucleotide No. 251 and No. 256, DIP NO. 35:
- SEQ ID NO. 69 wherein the deletion-insertion polymorphism is between nucleotide No. 250 and No. 251,
- SEQ ID NO. 70 wherein the deletion-insertion polymorphism is between nucleotide No. 250 and No. 255, DIP NO. 36:
- SEQ ID NO. 71 wherein the deletion-insertion polymorphism is between nucleotide No. 250 and No. 251,
- SEQ ID NO. 72 wherein the deletion-insertion polymorphism is between nucleotide No. 250 and No. 258, DIP NO. 37:
- SEQ ID NO. 73 wherein the deletion-insertion polymorphism is between nucleotide No. 251 and No. 252,
- SEQ ID NO. 74 wherein the deletion-insertion polymorphism is between nucleotide No. 251 and No. 256, DIP NO. 38:
- SEQ ID NO. 75 wherein the deletion-insertion polymorphism is between nucleotide No. 255 and No. 256,
- SEQ ID NO. 76 wherein the deletion-insertion polymorphism is between nucleotide No. 255 and No. 261, DIP NO. 39:
- SEQ ID NO. 77 wherein the deletion-insertion polymorphism is between nucleotide No. 251 and No. 252,
- SEQ ID NO. 78 wherein the deletion-insertion polymorphism is between nucleotide No. 251 and No. 256, DIP NO. 40:
- SEQ ID NO. 79 wherein the deletion-insertion polymorphism is between nucleotide No. 250 and No. 251,
- SEQ ID NO. 80 wherein the deletion-insertion polymorphism is between nucleotide No. 250 and No. 259, DIP NO. 41:
- SEQ ID NO. 81 wherein the deletion-insertion polymorphism is between nucleotide No. 251 and No. 252,
- SEQ ID NO. 82 wherein the deletion-insertion polymorphism is between nucleotide No. 251 and No. 254, DIP NO. 42:
- SEQ ID NO. 83 wherein the deletion-insertion polymorphism is between nucleotide No. 251 and No. 252,
- SEQ ID NO. 84 wherein the deletion-insertion polymorphism is between nucleotide No. 251 and No. 254, DIP NO. 43:
- SEQ ID NO. 85 wherein the deletion-insertion polymorphism is between nucleotide No. 251 and No. 252,
- SEQ ID NO. 86 wherein the deletion-insertion polymorphism is between nucleotide No. 251 and No. 255, DIP NO. 44:
  SEQ ID NO. 87 wherein the deletion-insertion polymorphism is between nucleotide No. 250 and No. 251,
  SEQ ID NO. 88 wherein the deletion-insertion polymorphism is between nucleotide No. 250 and No. 254,
DIP NO. 45:
  SEQ ID NO. 89 wherein the deletion-insertion polymorphism is between nucleotide No. 250 and No. 251,
  SEQ ID NO. 90 wherein the deletion-insertion polymorphism is between nucleotide No. 250 and No. 254,
DIP NO. 46:
  SEQ ID NO. 91 wherein the deletion-insertion polymorphism is between nucleotide No. 250 and No. 251,
  SEQ ID NO. 92 wherein the deletion-insertion polymorphism is between nucleotide No. 250 and No. 254,
DIP NO. 47:
  SEQ ID NO. 93 wherein the deletion-insertion polymorphism is between nucleotide No. 251 and No. 252,
  SEQ ID NO. 94 wherein the deletion-insertion polymorphism is between nucleotide No. 251 and No. 256,
DIP NO. 48:
  SEQ ID NO. 95 wherein the deletion-insertion polymorphism is between nucleotide No. 251 and No. 252,
  SEQ ID NO. 96 wherein the deletion-insertion polymorphism is between nucleotide No. 251 and No. 256,
DIP NO. 49:
  SEQ ID NO. 97 wherein the deletion-insertion polymorphism is between nucleotide No. 247 and No. 248,
  SEQ ID NO. 98 wherein the deletion-insertion polymorphism is between nucleotide No. 247 and No. 252,
DIP NO. 50:
  SEQ ID NO. 99 wherein the deletion-insertion polymorphism is between nucleotide No. 250 and No. 251,
  SEQ ID NO. 100 wherein the deletion-insertion polymorphism is between nucleotide No. 250 and No. 256,
DIP NO. 51:
  SEQ ID NO. 101 wherein the deletion-insertion polymorphism is between nucleotide No. 251 and No. 252,
  SEQ ID NO. 102 wherein the deletion-insertion polymorphism is between nucleotide No. 251 and No. 257,
DIP NO. 52:
  SEQ ID NO. 103 wherein the deletion-insertion polymorphism is between nucleotide No. 250 and No. 251,
  SEQ ID NO. 104 wherein the deletion-insertion polymorphism is between nucleotide No. 250 and No. 256,
DIP NO. 53:
  SEQ ID NO. 105 wherein the deletion-insertion polymorphism is between nucleotide No. 250 and No. 251,
  SEQ ID NO. 106 wherein the deletion-insertion polymorphism is between nucleotide No. 250 and No. 256,
DIP NO. 54:
  SEQ ID NO. 107 wherein the deletion-insertion polymorphism is between nucleotide No. 251 and No. 252,
  SEQ ID NO. 108 wherein the deletion-insertion polymorphism is between nucleotide No. 251 and No. 258,
DIP NO. 55:
  SEQ ID NO. 109 wherein the deletion-insertion polymorphism is between nucleotide No. 251 and No. 252,
  SEQ ID NO. 110 wherein the deletion-insertion polymorphism is between nucleotide No. 251 and No. 258,
DIP NO. 56:
  SEQ ID NO. 111 wherein the deletion-insertion polymorphism is between nucleotide No. 250 and No. 251,
  SEQ ID NO. 112 wherein the deletion-insertion polymorphism is between nucleotide No. 250 and No. 258,
DIP NO. 57:
  SEQ ID NO. 113 wherein the deletion-insertion polymorphism is between nucleotide No. 246 and No. 247,
  SEQ ID NO. 114 wherein the deletion-insertion polymorphism is between nucleotide No. 246 and No. 252,
DIP NO. 58:
  SEQ ID NO. 115 wherein the deletion-insertion polymorphism is between nucleotide No. 250 and No. 251,
  SEQ ID NO. 116 wherein the deletion-insertion polymorphism is between nucleotide No. 250 and No. 263,
DIP NO. 59:
  SEQ ID NO. 117 wherein the deletion-insertion polymorphism is between nucleotide No. 250 and No. 251,
  SEQ ID NO. 118 wherein the deletion-insertion polymorphism is between nucleotide No. 250 and No. 266,
DIP NO. 60:
  SEQ ID NO. 119 wherein the deletion-insertion polymorphism is between nucleotide No. 251 and No. 252,
  SEQ ID NO. 120 wherein the deletion-insertion polymorphism is between nucleotide No. 251 and No. 268,
DIP NO. 61:
  SEQ ID NO. 121 wherein the deletion-insertion polymorphism is between nucleotide No. 250 and No. 251,
  SEQ ID NO. 122 wherein the deletion-insertion polymorphism is between nucleotide No. 250 and No. 277,
DIP NO. 62:
  SEQ ID NO. 123 wherein the deletion-insertion polymorphism is between nucleotide No. 251 and No. 252,
  SEQ ID NO. 124 wherein the deletion-insertion polymorphism is between nucleotide No. 251 and No. 260,
DIP NO. 63:
  SEQ ID NO. 289 wherein the deletion-insertion polymorphism is between nucleotide No. 250 and No. 251,
  SEQ ID NO. 290 wherein the deletion-insertion polymorphism is between nucleotide No. 250 and No. 256,
and wherein the primer pairs are each specific for a different DIP sequence.

It is preferred that the kit comprises at least 4, 5, 6, 7, 8, 9, 10, 11, 12, 13, 14, 15, 16, 17, 18, 19, 20, 21, 22, 23, 24, 25, 26, 27 or more than 30 primer pairs.

It is preferred that a kit comprises at least primers for 20, 30 or 40 DIPs and that such a kit comprises primers for DIP number 31 (SEQ ID NO. 61 and 62) and DIP number 32 (SEQ ID NO. 63 and 64) These two DIPs are DIPs on the Y-chromosome and the X-chromosome respectively.

It is preferred that the kit comprises 6, 7, 8, 9, 10, 11, 12, 13, 14, 15, 16, 17, 18, 19, 20, 21, 22, 23, 24, 25, 26, 27, 28, 29, or 30 primer pairs which are each able to bind a different sequence selected from the group disclosed above.

A kit is preferred wherein the primer pairs are selected from the following group of primer pairs:
- a) DIP NO. 1: SEQ ID NO. 125 and SEQ ID NO. 126 or SEQ ID NO. 267 and SEQ ID NO. 268
- b) DIP NO. 2: SEQ ID NO. 127 and SEQ ID NO. 128
- c) DIP NO. 3: SEQ ID NO. 129 and SEQ ID NO. 130
- d) DIP NO. 4: SEQ ID NO. 131 and SEQ ID NO. 132
- e) DIP NO. 5: SEQ ID NO. 133 and SEQ ID NO. 134
- f) DIP NO. 6: SEQ ID NO. 135 and SEQ ID NO. 136
- g) DIP NO. 7: SEQ ID NO. 137 and SEQ ID NO. 138
- h) DIP NO. 8: SEQ ID NO. 139 and SEQ ID NO. 140 or SEQ ID NO. 287 and SEQ ID NO. 288
- i) DIP NO. 9: SEQ ID NO. 141 and SEQ ID NO. 142
- j) DIP NO. 10: SEQ ID NO. 143 and SEQ ID NO. 144
- k) DIP NO. 11: SEQ ID NO. 145 and SEQ ID NO. 146
- l) DIP NO. 12: SEQ ID NO. 147 and SEQ ID NO. 148
- m) DIP NO. 13: SEQ ID NO. 149 and SEQ ID NO. 150
- n) DIP NO. 14: SEQ ID NO. 151 and SEQ ID NO. 152
- o) DIP NO. 15: SEQ ID NO. 153 and SEQ ID NO. 154 or SEQ ID NO. 281 and SEQ ID NO. 282
- p) DIP NO. 16: SEQ ID NO. 155 and SEQ ID NO. 156
- q) DIP NO. 17: SEQ ID NO. 157 and SEQ ID NO. 158 or SEQ ID NO. 273 and SEQ ID NO. 274
- r) DIP NO. 18: SEQ ID NO. 159 and SEQ ID NO. 160 or SEQ ID NO. 277 and SEQ ID NO. 278
- s) DIP NO. 19: SEQ ID NO. 161 and SEQ ID NO. 162 or SEQ ID NO. 279 and SEQ ID NO. 280
- t) DIP NO. 20: SEQ ID NO. 163 and SEQ ID NO. 164 or SEQ ID NO. 275 and SEQ ID NO. 276
- u) DIP NO. 21: SEQ ID NO. 165 and SEQ ID NO. 166
- v) DIP NO. 22: SEQ ID NO. 167 and SEQ ID NO. 168
- w) DIP NO. 23: SEQ ID NO. 169 and SEQ ID NO. 170
- x) DIP NO. 24: SEQ ID NO. 171 and SEQ ID NO. 172
- y) DIP NO. 25: SEQ ID NO. 173 and SEQ ID NO. 174
- z) DIP NO. 26: SEQ ID NO. 175 and SEQ ID NO. 176
- aa) DIP NO. 27: SEQ ID NO. 177 and SEQ ID NO. 178
- ab) DIP NO. 28: SEQ ID NO. 179 and SEQ ID NO. 180
- ac) DIP NO. 29: SEQ ID NO. 181 and SEQ ID NO. 182 or SEQ ID NO. 271 and SEQ ID NO. 272
- ad) DIP NO. 30: SEQ ID NO. 183 and SEQ ID NO. 184 or SEQ ID NO. 283 and SEQ ID NO. 284
- ae) DIP NO. 31: SEQ ID NO. 185 and SEQ ID NO. 186
- af) DIP NO. 32: SEQ ID NO. 187 and SEQ ID NO. 188 or SEQ ID NO. 269 and SEQ ID NO. 270
- ag) DIP NO. 33: SEQ ID NO. 189 and SEQ ID NO. 190 or SEQ ID NO. 285 and SEQ ID NO. 286
- ah) DIP NO. 34: SEQ ID NO. 191 and SEQ ID NO. 191
- ai) DIP NO. 35: SEQ ID NO. 193 and SEQ ID NO. 194
- aj) DIP NO. 36: SEQ ID NO. 195 and SEQ ID NO. 196
- ak) DIP NO. 37: SEQ ID NO. 197 and SEQ ID NO. 198
- al) DIP NO. 38: SEQ ID NO. 199 and SEQ ID NO. 200
- am) DIP NO. 39: SEQ ID NO. 201 and SEQ ID NO. 202
- an) DIP NO. 40: SEQ ID NO. 203 and SEQ ID NO. 204
- ao) DIP NO. 41: SEQ ID NO. 205 and SEQ ID NO. 206 or SEQ ID NO. 251 and SEQ ID NO. 252
- ap) DIP NO. 42: SEQ ID NO. 207 and SEQ ID NO. 208 or SEQ ID NO. 253 and SEQ ID NO. 254
- aq) DIP NO. 43: SEQ ID NO. 209 and SEQ ID NO. 210 or SEQ ID NO. 255 and SEQ ID NO. 256
- ar) DIP NO. 44: SEQ ID NO. 211 and SEQ ID NO. 212 or SEQ ID NO. 257 and SEQ ID NO. 258
- as) DIP NO. 45: SEQ ID NO. 213 and SEQ ID NO. 214 or SEQ ID NO. 259 and SEQ ID NO. 260
- at) DIP NO. 46: SEQ ID NO. 215 and SEQ ID NO. 216 or SEQ ID NO. 261 and SEQ ID NO. 262
- au) DIP NO. 47: SEQ ID NO. 217 and SEQ ID NO. 218 or SEQ ID NO. 263 and SEQ ID NO. 264
- av) DIP NO. 48: SEQ ID NO. 219 and SEQ ID NO. 220
- aw) DIP NO. 49: SEQ ID NO. 221 and SEQ ID NO. 222
- ax) DIP NO. 50: SEQ ID NO. 223 and SEQ ID NO. 224
- ay) DIP NO. 51: SEQ ID NO. 225 and SEQ ID NO. 226 or SEQ ID NO. 265 and SEQ ID NO. 266
- az) DIP NO. 52: SEQ ID NO. 227 and SEQ ID NO. 228
- ba) DIP NO. 53: SEQ ID NO. 229 and SEQ ID NO. 230
- bb) DIP NO. 54: SEQ ID NO. 231 and SEQ ID NO. 232
- bc) DIP NO. 55: SEQ ID NO. 233 and SEQ ID NO. 234
- bd) DIP NO. 56: SEQ ID NO. 235 and SEQ ID NO. 236
- be) DIP NO. 57: SEQ ID NO. 237 and SEQ ID NO. 238
- bf) DIP NO. 58: SEQ ID NO. 239 and SEQ ID NO. 240
- bg) DIP NO. 59: SEQ ID NO. 241 and SEQ ID NO. 242
- bh) DIP NO. 60: SEQ ID NO. 243 and SEQ ID NO. 244
- bi) DIP NO. 61: SEQ ID NO. 245 and SEQ ID NO. 246
- bj) DIP NO. 62: SEQ ID NO. 247 and SEQ ID NO. 248
- bk) DIP NO. 63: SEQ ID NO. 249 and SEQ ID NO. 250

In one embodiment of the invention the invention related to the use of a selection of at least 2, 3, 4, 5, 6, 7, 8, 9, 10, 11, 12, 13, 14, 15, 16, 17, 18, 19, 20, 21, 22, 23, 24, 25, 26, 27, 28, 29, 30 or more sequences selected from the group of:

DIP NO. 1:
  SEQ ID NO. 1 wherein the deletion-insertion polymorphism is between nucleotide No. 251 and No. 252,
  SEQ ID NO. 2 wherein the deletion-insertion polymorphism is between nucleotide No. 251 and No. 256,
DIP NO. 2:
  SEQ ID NO. 3 wherein the deletion-insertion polymorphism is between nucleotide No. 250 and No. 251,
  SEQ ID NO. 4 wherein the deletion-insertion polymorphism is between nucleotide No. 250 and No. 255,
DIP NO. 3:
  SEQ ID NO. 5 wherein the deletion-insertion polymorphism is between nucleotide No. 251 and No. 252,
  SEQ ID NO. 6 wherein the deletion-insertion polymorphism is between nucleotide No. 251 and No. 256,
DIP NO. 4:
  SEQ ID NO. 7 wherein the deletion-insertion polymorphism is between nucleotide No. 250 and No. 251,
  SEQ ID NO. 8 wherein the deletion-insertion polymorphism is between nucleotide No. 250 and No. 262,
DIP NO. 5:
  SEQ ID NO. 9 wherein the deletion-insertion polymorphism is between nucleotide No. 251 and No. 252,
  SEQ ID NO. 10 wherein the deletion-insertion polymorphism is between nucleotide No. 251 and No. 256,
DIP NO. 6:
  SEQ ID NO. 11 wherein the deletion-insertion polymorphism is between nucleotide No. 251 and No. 252,
  SEQ ID NO. 12 wherein the deletion-insertion polymorphism is between nucleotide No. 251 and No. 256,
DIP NO. 7:
  SEQ ID NO. 13 wherein the deletion-insertion polymorphism is between nucleotide No. 251 and No. 252,
  SEQ ID NO. 14 wherein the deletion-insertion polymorphism is between nucleotide No. 251 and No. 256, DIP NO. 8:
- SEQ ID NO. 15 wherein the deletion-insertion polymorphism is between nucleotide No. 251 and No. 252,
- SEQ ID NO. 16 wherein the deletion-insertion polymorphism is between nucleotide No. 251 and No. 256, DIP NO. 9:
- SEQ ID NO. 17 wherein the deletion-insertion polymorphism is between nucleotide No. 251 and No. 252,
- SEQ ID NO. 18 wherein the deletion-insertion polymorphism is between nucleotide No. 251 and No. 257, DIP NO. 10:
- SEQ ID NO. 19 wherein the deletion-insertion polymorphism is between nucleotide No. 246 and No. 247,
- SEQ ID NO. 20 wherein the deletion-insertion polymorphism is between nucleotide No. 246 and No. 252, DIP NO. 11:
- SEQ ID NO. 21 wherein the deletion-insertion polymorphism is between nucleotide No. 251 and No. 252,
- SEQ ID NO. 22 wherein the deletion-insertion polymorphism is between nucleotide No. 251 and No. 256, DIP NO. 12:
- SEQ ID NO. 23 wherein the deletion-insertion polymorphism is between nucleotide No. 250 and No. 251,
- SEQ ID NO. 24 wherein the deletion-insertion polymorphism is between nucleotide No. 250 and No. 260, DIP NO. 13:
- SEQ ID NO. 25 wherein the deletion-insertion polymorphism is between nucleotide No. 251 and No. 252,
- SEQ ID NO. 26 wherein the deletion-insertion polymorphism is between nucleotide No. 251 and No. 256, DIP NO. 14:
- SEQ ID NO. 27 wherein the deletion-insertion polymorphism is between nucleotide No. 251 and No. 252,
- SEQ ID NO. 28 wherein the deletion-insertion polymorphism is between nucleotide No. 251 and No. 260, DIP NO. 15:
- SEQ ID NO. 29 wherein the deletion-insertion polymorphism is between nucleotide No. 251 and No. 252,
- SEQ ID NO. 30 wherein the deletion-insertion polymorphism is between nucleotide No. 251 and No. 263, DIP NO. 16:
- SEQ ID NO. 31 wherein the deletion-insertion polymorphism is between nucleotide No. 251 and No. 252,
- SEQ ID NO. 32 wherein the deletion-insertion polymorphism is between nucleotide No. 251 and No. 256, DIP NO: 17:
- SEQ ID NO. 33 wherein the deletion-insertion polymorphism is between nucleotide No. 251 and No. 252,
- SEQ ID NO. 34 wherein the deletion-insertion polymorphism is between nucleotide No. 251 and No. 270, DIP NO. 18:
- SEQ ID NO. 35 wherein the insertion-deletion polymorphism is between nucleotide No. 251 and No. 252,
- SEQ ID NO. 36 wherein the insertion-deletion polymorphism is between nucleotide No. 251 and No. 263, DIP NO. 19:
- SEQ ID NO. 37 wherein the deletion-insertion polymorphism is between nucleotide No. 251 and No. 252,
- SEQ ID NO. 38 wherein the deletion-insertion polymorphism is between nucleotide No. 251 and No. 257, DIP NO. 20:
- SEQ ID NO. 39 wherein the deletion-insertion polymorphism is between nucleotide No. 251 and No. 252,
- SEQ ID NO. 40 wherein the deletion-insertion polymorphism is between nucleotide No. 251 and No. 257, DIP NO. 21:
- SEQ ID NO. 41 wherein the deletion-insertion polymorphism is between nucleotide No. 251 and No. 252,
- SEQ ID NO. 42 wherein the deletion-insertion polymorphism is between nucleotide No. 251 and No. 258, DIP NO 22:
- SEQ ID NO. 43 wherein the deletion-insertion polymorphism is between nucleotide No. 250 and No. 251,
- SEQ ID NO. 44 wherein the deletion-insertion polymorphism is between nucleotide No. 250 and No. 257, DIP NO. 23:
- SEQ ID NO. 45 wherein the deletion-insertion polymorphism is between nucleotide No. 251 and No. 252,
- SEQ ID NO. 46 wherein the deletion-insertion polymorphism is between nucleotide No. 251 and No. 257, DIP NO. 24:
- SEQ ID NO. 47 wherein the deletion-insertion polymorphism is between nucleotide No. 251 and No. 252,
- SEQ ID NO. 48 wherein the deletion-insertion polymorphism is between nucleotide No. 251 and No. 263, DIP NO. 25:
- SEQ ID NO. 49 wherein the deletion-insertion polymorphism is between nucleotide No. 250 and No. 251,
- SEQ ID NO. 50 wherein the deletion-insertion polymorphism is between nucleotide No. 250 and No. 296, DIP NO. 26:
- SEQ ID NO. 51 wherein the deletion-insertion polymorphism is between nucleotide No. 251 and No. 252,
- SEQ ID NO. 52 wherein the deletion-insertion polymorphism is between nucleotide No. 251 and No. 266, DIP NO 27:
- SEQ ID NO. 53 wherein the deletion-insertion polymorphism is between nucleotide No. 250 and No. 251,
- SEQ ID NO. 54 wherein the deletion-insertion polymorphism is between nucleotide No. 250 and No. 273, DIP NO. 28:
- SEQ ID NO. 55 wherein the deletion-insertion polymorphism is between nucleotide No. 251 and No. 252,
- SEQ ID NO. 56 wherein the deletion-insertion polymorphism is between nucleotide No. 251 and No. 260, DIP NO. 29:
- SEQ ID NO. 57 wherein the deletion-insertion polymorphism is between nucleotide No. 251 and No. 252,
- SEQ ID NO. 58 wherein the deletion-insertion polymorphism is between nucleotide No. 251 and No. 267, DIP NO. 30:
- SEQ ID NO. 59 wherein the deletion-insertion polymorphism is between nucleotide No. 251 and No. 252,
- SEQ ID NO. 60 wherein the deletion-insertion polymorphism is between nucleotide No. 251 and No. 270, DIP NO. 31:
- SEQ ID NO. 61 wherein the deletion-insertion polymorphism is between nucleotide No. 271 and No. 272,
- SEQ ID NO. 62 wherein the deletion-insertion polymorphism is between nucleotide No. 271 and No. 278, DIP NO. 32:
- SEQ ID NO. 63 wherein the deletion-insertion polymorphism is between nucleotide No. 280 and No. 281,
- SEQ ID NO. 64 wherein the deletion-insertion polymorphism is between nucleotide No. 280 and No. 284, DIP NO. 33:
- SEQ ID NO. 65 wherein the deletion-insertion polymorphism is between nucleotide No. 250 and No. 251,
- SEQ ID NO. 66 wherein the deletion-insertion polymorphism is between nucleotide No. 250 and No. 256, DIP NO. 34:
- SEQ ID NO. 67 wherein the deletion-insertion polymorphism is between nucleotide No. 251 and No. 252, SEQ ID NO. 68 wherein the deletion-insertion polymorphism is between nucleotide No. 251 and No. 256, DIP NO. 35:
SEQ ID NO. 69 wherein the deletion-insertion polymorphism is between nucleotide No. 250 and No. 251,
SEQ ID NO. 70 wherein the deletion-insertion polymorphism is between nucleotide No. 250 and No. 255, DIP NO. 36:
SEQ ID NO. 71 wherein the deletion-insertion polymorphism is between nucleotide No. 250 and No. 251,
SEQ ID NO. 72 wherein the deletion-insertion polymorphism is between nucleotide No. 250 and No. 258, DIP NO. 37:
SEQ ID NO. 73 wherein the deletion-insertion polymorphism is between nucleotide No. 251 and No. 252,
SEQ ID NO. 74 wherein the deletion-insertion polymorphism is between nucleotide No. 251 and No. 256, DIP NO. 38:
SEQ ID NO. 75 wherein the deletion-insertion polymorphism is between nucleotide No. 255 and No. 256,
SEQ ID NO. 76 wherein the deletion-insertion polymorphism is between nucleotide No. 255 and No. 261, DIP NO. 39:
SEQ ID NO. 77 wherein the deletion-insertion polymorphism is between nucleotide No. 251 and No. 252,
SEQ ID NO. 78 wherein the deletion-insertion polymorphism is between nucleotide No. 251 and No. 256, DIP NO. 40:
SEQ ID NO. 79 wherein the deletion-insertion polymorphism is between nucleotide No. 250 and No. 251,
SEQ ID NO. 80 wherein the deletion-insertion polymorphism is between nucleotide No. 250 and No. 259, DIP NO. 41:
SEQ ID NO. 81 wherein the deletion-insertion polymorphism is between nucleotide No. 251 and No. 252,
SEQ ID NO. 82 wherein the deletion-insertion polymorphism is between nucleotide No. 251 and No. 254, DIP NO. 42:
SEQ ID NO. 83 wherein the deletion-insertion polymorphism is between nucleotide No. 251 and No. 252,
SEQ ID NO. 84 wherein the deletion-insertion polymorphism is between nucleotide No. 251 and No. 254, DIP NO. 43:
SEQ ID NO. 85 wherein the deletion-insertion polymorphism is between nucleotide No. 251 and No. 252,
SEQ ID NO. 86 wherein the deletion-insertion polymorphism is between nucleotide No. 251 and No. 255, DIP NO. 44:
SEQ ID NO. 87 wherein the deletion-insertion polymorphism is between nucleotide No. 250 and No. 251,
SEQ ID NO. 88 wherein the deletion-insertion polymorphism is between nucleotide No. 250 and No. 254, DIP NO. 45:
SEQ ID NO. 89 wherein the deletion-insertion polymorphism is between nucleotide No. 250 and No. 251,
SEQ ID NO. 90 wherein the deletion-insertion polymorphism is between nucleotide No. 250 and No. 254, DIP NO. 46:
SEQ ID NO. 91 wherein the deletion-insertion polymorphism is between nucleotide No. 250 and No. 251,
SEQ ID NO. 92 wherein the deletion-insertion polymorphism is between nucleotide No. 250 and No. 254, DIP NO. 47:
SEQ ID NO. 93 wherein the deletion-insertion polymorphism is between nucleotide No. 251 and No. 252,
SEQ ID NO. 94 wherein the deletion-insertion polymorphism is between nucleotide No. 251 and No. 256, DIP NO. 48:
SEQ ID NO. 95 wherein the deletion-insertion polymorphism is between nucleotide No. 251 and No. 252,
SEQ ID NO. 96 wherein the deletion-insertion polymorphism is between nucleotide No. 251 and No. 256, DIP NO. 49:
SEQ ID NO. 97 wherein the deletion-insertion polymorphism is between nucleotide No. 247 and No. 248,
SEQ ID NO. 98 wherein the deletion-insertion polymorphism is between nucleotide No. 247 and No. 252, DIP NO. 50:
SEQ ID NO. 99 wherein the deletion-insertion polymorphism is between nucleotide No. 250 and No. 251,
SEQ ID NO. 100 wherein the deletion-insertion polymorphism is between nucleotide No. 250 and No. 256, DIP NO. 51:
SEQ ID NO. 101 wherein the deletion-insertion polymorphism is between nucleotide No. 251 and No. 252,
SEQ ID NO. 102 wherein the deletion-insertion polymorphism is between nucleotide No. 251 and No. 257, DIP NO. 52:
SEQ ID NO. 103 wherein the deletion-insertion polymorphism is between nucleotide No. 250 and No. 251,
SEQ ID NO. 104 wherein the deletion-insertion polymorphism is between nucleotide No. 250 and No. 256, DIP NO. 53:
SEQ ID NO. 105 wherein the deletion-insertion polymorphism is between nucleotide No. 250 and No. 251,
SEQ ID NO. 106 wherein the deletion-insertion polymorphism is between nucleotide No. 250 and No. 256, DIP NO. 54:
SEQ ID NO. 107 wherein the deletion-insertion polymorphism is between nucleotide No. 251 and No. 252,
SEQ ID NO. 108 wherein the deletion-insertion polymorphism is between nucleotide No. 251 and No. 258, DIP NO. 55:
SEQ ID NO. 109 wherein the deletion-insertion polymorphism is between nucleotide No. 251 and No. 252,
SEQ ID NO. 110 wherein the deletion-insertion polymorphism is between nucleotide No. 251 and No. 258, DIP NO. 56:
SEQ ID NO. 111 wherein the deletion-insertion polymorphism is between nucleotide No. 250 and No. 251,
SEQ ID NO. 112 wherein the deletion-insertion polymorphism is between nucleotide No. 250 and No. 258, DIP NO. 57:
SEQ ID NO. 113 wherein the deletion-insertion polymorphism is between nucleotide No. 246 and No. 247,
SEQ ID NO. 114 wherein the deletion-insertion polymorphism is between nucleotide No. 246 and No. 252, DIP NO. 58:
    SEQ ID NO. 115 wherein the deletion-insertion polymorphism is between nucleotide No. 250 and No. 251,
    SEQ ID NO. 116 wherein the deletion-insertion polymorphism is between nucleotide No. 250 and No. 263,
DIP NO. 59:
    SEQ ID NO. 117 wherein the deletion-insertion polymorphism is between nucleotide No. 250 and No. 251,
    SEQ ID NO. 118 wherein the deletion-insertion polymorphism is between nucleotide No. 250 and No. 266,
DIP NO. 60:
    SEQ ID NO. 119 wherein the deletion-insertion polymorphism is between nucleotide No. 251 and No. 252,
    SEQ ID NO. 120 wherein the deletion-insertion polymorphism is between nucleotide No. 251 and No. 268,
DIP NO. 61:
    SEQ ID NO. 121 wherein the deletion-insertion polymorphism is between nucleotide No. 250 and No. 251,
    SEQ ID NO. 122 wherein the deletion-insertion polymorphism is between nucleotide No. 250 and No. 277,
DIP NO. 62:
    SEQ ID NO. 123 wherein the deletion-insertion polymorphism is between nucleotide No. 251 and No. 252,
    SEQ ID NO. 124 wherein the deletion-insertion polymorphism is between nucleotide No. 251 and No. 260 and
DIP NO. 63:
    SEQ ID NO. 289 wherein the deletion-insertion polymorphism is between nucleotide No. 250 and No. 251,
    SEQ ID NO. 290 wherein the deletion-insertion polymorphism is between nucleotide No. 250 and No. 256.

The sequences may be used only in part. The use may be 90% of the sequence, 80%, 70%, 60%, 50%, 40%, 30% or 20% as long as the use encompasses DIP. That means if a sequence is disclosed herein that has 100 nucleotides and the DIP is located 30 nucleotides away from the 5' end of the sequence then a 50% use would mean, e.g. amplifying the first 50 nucleotides starting at the 5' end, it would also mean of course amplifying any 50 nucleotides as long as the encompass the DIP polymorphism. DIP NO. 31 and 32 are the amelogenin DIPs. It is preferred that these are part of those DIPs selected.

In one embodiment, the kit may further comprise components needed to carry out "real-time PCR" applications. The term "real-time PCR" describes a system based on the detection and quantitation of a fluorescent signal. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. A significant increase in fluorescence above the baseline value measured during the 3-15 cycles indicates the detection of accumulated PCR product. Components include, but are not limited to intercalation dyes, fluorescently labelled primers and probes, and derivatives of the same.

Kits of the present invention may include information pamphlets.

It is preferred if the use according to the inventive profiling assay is a ligase chain reaction assay, a hybridization assay, polymerase chain reaction assay, chip based assay. A hybridization assay, arrayed primer extension (APEX) also referred to as chip-based mini-sequencing reaction or single base extension, arrayed ligation assay, allele specific arrayed ligation assay is also preferred. A polymerase chain reaction assay is most preferred.

Other genotyping techniques which possess a high degree of multiplex capability are chip-based technologies single base primer extension (SnaPShot) or OLA-based (SNPIex) in combination with capillary electrophoresis and bead-based technologies with addressing sequences. These and the methods below may be used with the probes disclosed herein and fall within the invention.

Further detection techniques are known which allow genotyping of bi-allelic polymorphisms from multiplex DNA mixtures. For reviews see Syvänen (2001) (Syvänen AC, 2001. Accessing genetic variation: Genotyping single nucleotide polymorphisms. Nature Reviews Genetics 2: 930-941) and Kwock (2003) (Kwock P Y, 2003. Single Nucleotide Polymorphisms. Methods and Protocols. Humana Press, Totowa, N.J., USA). Of particular value for the inventive process are those techniques which allow the simultaneous genotyping of a plurality of DIPs in one reaction. Two commercial available systems which use multi-colour DNA sequencing automates in combination with capillary electrophoresis are the SNaPshot® Multiplex System and the SNPlex™ Genotyping System (both from Applied Biosystems, Foster City, Calif., USA). The first is a primer extension-based method that enables, according to the manufacturer, the detection of more than 10 biallelic polymorhisms, the second combines a multiplex allele-specific oligo ligation assay (OLA) with a PCR and enables the simultaneous genotyping of up to 48 biallelic polymorphisms. Another electrophoresis based multiplex genotyping approach is described as *Multiplex Ligation-dependent Probe Amplification* (MLPA; Schouten J P, McElgunn C J, Waaijer R, Zwijnenburg D, Diepvens F and Pals G (2002). Relative quantification of 40 nucleic acid sequences by multiplex ligation-dependent probe amplification. Nucleic Acids Res 30: e57). Furthermore, DNA-chip based technologies are of special use for the inventive process. EU Patent No. 820,524 and U.S. Pat. No. 5,679,524 (which are hereby incorporated by reference) disclose chip based allele specific hybridizations assays, arrayed primer extension (APEX, also referred to as chip-based mini-sequencing reaction or single base primer extension on a chip), arrayed ligation reaction and allele specific arrayed ligation assay. EU Patent No. 799,897 (which is hereby incorporated by reference) teaches the use of universal tag-arrays and EU Patent No. 1,186,669 897 (which is hereby incorporated by reference) addresses allele specific nested on a chip (NOC™)-PCR. Finally, U.S. Pat. No 6,287,778 897 (which is hereby incorporated by reference) describes universal tag-sequences in combination with beads.

The kit of the invention may be used for DNA profiling, in particular for forensic applications.

The kit may additionally comprise an allelic ladder.

FIGURE CAPTIONS

FIG. 1: Human DNA profiling and sex determination by multiplex PCR amplification and genotyping of one gonosomal and 30 autosomal DIPs. Electropherograms which show the relative fluorescent units (RFUs) for the dyes 6-FAM, VIC, NED, PET and LIZ over the fragment size in basepairs [bp] are depicted. The multiplex PCR and genotyping was done as explained in the text for example 1 starting from 250 pg genomic DNA of a male person. A post PCR purification step was applied prior electrophoresis as outlined in the text. An internal LIZ-labelled size standard was used to calculate the fragment size. The assignment between peaks and alleles is marked at the bottom of each electropherogram.

FIG. 2: Compilation of DIP marker codes and SEQ ID numbers of alleles and PCR primers.

EXAMPLES

Example 1

Human DNA Profiling and Sex Determination by Multiplex PCR Amplification and Genotyping of One Gonosomal and 30 Autosomal DIPs Basic protocols and DNA preparation. All reagents and other consumables used were of PCR quality, particularly free of DNA, DNA- and RNA-dependent nucleases. Basic molecular genetic experiments were done according to Sambrook et al. (1989) (Sambrook J, Fritsche E F, Maniatis T. Molecular cloning. A laboratory manual. $2^{nd}$ edition, Cold Spring Harbor Laboratory Press, 1989). Human test specimens were whole blood or sputum, the latter of which was collected with sterile buccal swabs (Nerbe Plus GmbH, Winsen/Luhe, Germany) according to the instructions of the manufacturer. DNA was extracted using the NucleoSpin® Tissue kit (Macherey & Nagel, Dueren, Germany) according to the instructions of the manufacturer. DNA quantification was done by UV VIS spectroscopy (Sambrook et al., 1989) recording the absorbancy of nucleotide bases at 260 nm or quantitative real time PCR (qPCR) using the Quantifyler™ Human DNA quantification kit (Applied Biosystems, Foster City, Calif., USA) and an ABI Prism 7000 SDS real time thermocycler (Applied Biosystems, Foster City, Calif., USA).

Selection of genetic markers and PCR primer design. A 3 bp DIP (Seq. ID NO. 61 and 62) and a 6 bp DIP (Seq. ID NO. 63 and 64) which distinguish the two paralogue copies of the human amelogenin gene that are located within the non-recombining regions of the X- and Y-chromosome were chosen for sex determination. The DIP locus defined by Seq. ID NO. 63/64 was further used within the multiplex PCR of this example. In total 61 autosomal DIP loci were used according to the following criteria: Defined and mapped single copy target sequence within the human genome, nucleotide length of the DIP 2-30 bp, location on different chromosomes or physical distance of the markers of at least 10.000.000 bp for PCR multiplexes, allele frequency of the minor allele 0.3-0.5 and heterozygosity of at least 40% reported in at least one population study. From these loci 30 DIPs which are depicted in table 2 were further used for the multiplex PCR of this example. PCR primer design was performed. The specificity of the primers was checked against the human genome sequence using the software Blastn (Basic Local Alignment Search Tool nucleotides; Altschul S F, Gish W, Miller W, Myers E W, Lipman D J. Basic local alignment search tool. J Mol Biol, Vol 215, pp 403-410, 1990). The compatibility of the primers pairs for multiplexing was controlled with the software Autodimer (Vallone P M, Butler J M. AutoDimer: a screening tool for primer-dimer and hairpin structures. Biotechniques, Vol 37, pp 226-231, 2004). For multiplexing the oligonucleotide primer pairs were further carefully selected according to their amplicon size and fluorescent dye label to guarantee optimal signal separation in capillary gel electrophoresis. The oligonucleotide primers were synthetisized by standard phosphoramidite chemistry at a service laboratory (Eurogentec S A, Seraing, Belgium; or Applied Biosystems, Foster City, Calif., USA). One primer of each primer pair was covalently labelled at its 5'-end with the fluorescent dyes 6-carboxyfluorescein (6-FAM), 2'-chloro-7'phenyl-1,4-dichloro-6-carboxyfluorescein (VIC), 2'-chloro-5'-fluoro-7', 8'-benzo-1,4-dichloro-6-carboxyfluorescein (NED) or PET (proprietary of Applied Biosystems, Foster City, Calif., USA) using standard chemistry. All primers were purified at the service laboratories by ion pair reversed phase high performance liquid chromatography according to standard protocols, dissolved in TE-buffer (10 mM Tris/HCl pH 8.0, adjusted at room temperature, 1 mM EDTA) to 100 µMolar and stored at 4° C. in the dark.

The qualification of the primers for sensitivity and specificity was first tested in monoplex PCR (see next break) at 200 nM final concentration applying different concentrations of human (0.03-5.0 ng) and non human (up to 20 ng) DNA. Furthermore, temperature gradients (55-65° C.) for the annealing step were applied. These experiments were repeated for the setup of multiplex PCR and many rounds of manual primer redesign as well as optimization of the primer concentrations were performed. The final primers and their concentration in multiplex PCR are shown in table 2.

Polymerase chain reaction (PCR). The enzyme reaction contained in a total volume of 25 µL 50 mM Tris/HCl (pH 8.8; adjusted at room temperature), 20 mM $NH_4SO_4$, 0.2 mM dNTPs (equimolar mixture of dATP, dCTP, dGTP, dTTP), 1.5 mM $MgCl_2$, 1.5 Units JumpStart™ Taq DNA polymerase (Sigma-Aldrich Chemie GmbH, Taufkirchen, Germany), 200 µg/mL bovine serum albumin (Roche Diagnostics GmbH, Mannheim, Germany), 0.01% Tween 20 and 0.1-1.0 ng human genomic DNA. The primer pairs used and their final concentration in the PCR are depicted in table 2, and their nucleotide sequences are shown in the sequence protocols (Seq. ID. 125-184 and 187-188). An ABI 9600 (Applied Biosystems, Foster City, Calif., USA) thermocycler was used. The cycling conditions consisted of an initial thermal activation of 240 s at 95 C, followed be 30 cycles of 30 s denaturation at 94 C, 120 s primer annealing at 60 C and 75 s primer extension at 72 C. The ramp speed was set to 1° C./s for all temperature changes. Afterwards a final elongation step of 3600 s at 68° C. was performed to maximize the template independent addition of one nucleotide at the 3'-end (preferentially A) due to the intrinsic terminal transferase activity of Taq DNA polymerase.

TABLE 2

Oligonucleotide primers used for multiplex PCR. The marker code of the DIP alleles (Dx defines the DIP locus whereas x is the consecutive number; appendix minus (−) refers to the deletion and plus (+) to the insertion) is used in FIG. 1 to superscribe the peaks. The corresponding Seq ID numbers are listed.

| Seq ID NO. | Primer Sequence (5-3') | 5'-Fluorescent dye label | Seq ID NO. of the target DNA | Marker Code of DIP allele | Concentration within the multiplex PCR [nM] |
|---|---|---|---|---|---|
| 125 | TAAATTCTAACCTGCACTCAAAGG | 6-FAM | 1 and 2 | D1− and D1+ | 200 |
| 126 | TTAGTCCTGGATAGCCTTAGAAAAT | no | 1 and 2 | D1− and D1+ | 200 |
| 127 | TGCTGACGAAATTGCAGTAACTA | 6-FAM | 3 and 4 | D2− and D2+ | 260 |
| 128 | CACTTCTCTAGGGTCTATCCAGCTT | no | 3 and 4 | D2− and D2+ | 260 |
| 129 | TCCGTTGAAATTCTGCCATA | 6-FAM | 5 and 6 | D3− and D3+ | 240 |
| 130 | AAACTCACTGGACTGATAGTGCTG | no | 5 and 6 | D3− and D3+ | 240 |
| 131 | CCCTCTGTCCTCATCAACATG | 6-FAM | 7 and 8 | D4− and D4+ | 140 |
| 132 | TGGTAATTTGTTACAGTAGCCCAAA | no | 7 and 8 | D4− and D4+ | 140 |
| 133 | ACACTCTATGCCATGCTCCTG | 6-FAM | 9 and 10 | D5− and D5+ | 100 |
| 134 | CTGCAACTGCTGTCTTACCTCT | no | 9 and 10 | D5− and D5+ | 100 |
| 135 | GCAATCTCTCCTTTGGCAACT | 6-FAM | 11 and 12 | D6− and D6+ | 440 |
| 136 | AGAGCGCATCAGGTTGTCTG | no | 11 and 12 | D6− and D6+ | 440 |
| 137 | AGATGACAGATATGTTCACTGGCTA | 6-FAM | 13 and 14 | D7− and D7+ | 120 |
| 138 | AGAGCCCTCAAGTTAAGAATGATTT | no | 13 and 14 | D7− and D7+ | 120 |
| 139 | AGTGGTTTGTGATCTTGCCATC | 6-FAM | 15 and 16 | D8− and D8+ | 80 |
| 140 | AATGGGTCATGTCTTCCCTTC | no | 15 and 16 | D8− and D8+ | 80 |
| 141 | GGCTGGATTGAAGTGCATT | VIC | 17 and 18 | D9− and D9+ | 120 |
| 142 | GCTGTGTCATCAGGGATGG | no | 17 and 18 | D9− and D9+ | 120 |
| 143 | ACATCAGAGCCCTAAACAAACAA | VIC | 19 and 20 | D10− and D10+ | 120 |
| 144 | AGTGGTAAATCTTTGTTTGAAGGTG | no | 19 and 20 | D10− and D10+ | 120 |
| 145 | GTTGAGAGTCGTGGGTTTATCC | VIC | 21 and 22 | D11− and D11+ | 400 |
| 146 | TATCCTTTAATCAGGAATGGGTTT | no | 21 and 22 | D11− and O11+ | 400 |
| 147 | GGAAGGAATAACAAGTACCTCAGTT | VIC | 23 and 24 | D12− and D12+ | 160 |
| 148 | AAAGTGTCACAAGACCCTTAAACTT | no | 23 and 24 | D12− and D12+ | 160 |
| 149 | CCAATGTTCATCAGAACTGTCAATA | VIC | 25 and 26 | D13− and D13+ | 90 |
| 150 | GACTCCCAAGAGCTGTGGATT | no | 25 and 26 | D13− and D13+ | 90 |
| 151 | TGAAGTTTGAAAGAATAATGTAGGC | VIC | 27 and 28 | D14− and D14+ | 200 |
| 152 | ACATGATTCAACAGAATTGATTTTC | no | 27 and 28 | D14− and D14+ | 200 |
| 153 | TCAGTCCTATTTAGTAGAAGCTCAATT | VIC | 29 and 30 | D15− and D15+ | 400 |
| 154 | GTTTAATCCTATCAAAGAAGCATTG | no | 29 and 30 | D15− and D15+ | 400 |
| 155 | CTCCTTTGTTCCTCCTAATCTCTTT | NED | 31 and 32 | D16− and D16+ | 320 |
| 156 | GAATATATGAGACTCACACTGGTCCT | no | 31 and 32 | D16− and D16+ | 320 |
| 157 | TAGGGTCATAAACCCAGTCTGC | NED | 33 and 34 | D17− and D17+ | 320 |
| 158 | GTTTTAGGTCTCAGCATCACGTAG | no | 33 and 34 | D17− and D17+ | 320 |
| 159 | GTGCTGGTCCATTCTCTTGTAA | NED | 35 and 36 | D18− and D18+ | 400 |

TABLE 2-continued

Oligonucleotide primers used for multiplex PCR. The marker code of the DIP alleles (Dx defines the DIP locus whereas x is the consecutive number; appendix minus (−) refers to the deletion and plus (+) to the insertion) is used in FIG. 1 to superscribe the peaks. The corresponding Seq ID numbers are listed.

| Seq ID NO. | Primer Sequence (5-3') | 5'-Fluorescent dye label | Seq ID NO. of the target DNA | Marker Code of DIP allele | Concentration within the multiplex PCR [nM] |
|---|---|---|---|---|---|
| 160 | CTAGGTGCAGAGAGGGATACTG | no | 35 and 36 | D18− and D18+ | 400 |
| 161 | GAGGGCGACTATAAAGAGGATTC | NED | 37 and 38 | D19− and D19+ | 440 |
| 162 | TTCACGAAGCCACAAGTATT | no | 37 and 38 | D19− and D19+ | 440 |
| 163 | AAATTAAATTCAAATGTCCAACTG | NED | 39 and 40 | D20− and D20+ | 460 |
| 164 | TGTGTAGGAGGGTGTTTTATAGACAAAT | no | 39 and 40 | D20− and D20+ | 460 |
| 165 | AATGGCAAAGATACAGGTCTGG | NED | 41 and 42 | D21− and D21+ | 200 |
| 166 | AGGTGAAGTTGAGGCTCCTG | no | 41 and 42 | D21− and D21+ | 200 |
| 167 | TTTCTAAAGGCATCTGAAATAGTGG | NED | 43 and 44 | D22− and D22+ | 200 |
| 168 | CCTACATGAGGATGTCCTTCTACTT | no | 43 and 44 | D22− and D22+ | 200 |
| 169 | AGCCCACCAGAGCACTACAG | PET | 45 and 46 | D23− and D23+ | 400 |
| 170 | AGATGCTGTCAGGGCACGAC | no | 45 and 46 | D23− and D23+ | 400 |
| 171 | TAGACTCAAGAATTGACATTGACAC | PET | 47 and 48 | D24− and D24+ | 300 |
| 172 | GAAGTCTATTCCCCTACTCCTTG | no | 47 and 48 | D24− and D24+ | 300 |
| 173 | TGGGTAGGGTGTTATGTGTATCTTT | PET | 49 and 50 | D25− and D25+ | 400 |
| 174 | GTTCCAACAGAATTTAGCTTACTGC | no | 49 and 50 | D25− and D25+ | 400 |
| 175 | AAGAGTGAAACTCCGTCTCAAA | PET | 51 and 52 | D26− and D26+ | 300 |
| 176 | CTGCCTTCCAAAATACTATTGTTATC | no | 51 and 52 | D26− and D26+ | 300 |
| 177 | CACATCCCATCAGCTTCTACAA | PET | 53 and 54 | D27− and D27+ | 600 |
| 178 | GAGCCGGGTTCTCGTCTAGT | no | 53 and 54 | D27− and D27+ | 600 |
| 179 | TTACCACCAAGAGTTACATTACATG | PET | 55 and 56 | D28− and D28+ | 400 |
| 180 | TGTTGCGAAAGGAAACGCTAG | no | 55 and 56 | D28− and D28+ | 400 |
| 181 | GAAGCGGTCTGGAAGTCAGG | PET | 57 and 58 | D29− and D29+ | 1000 |
| 182 | ACACTCTTTGCAGGGTAC | no | 57 and 58 | D29− and D29+ | 1000 |
| 183 | TTACTTGCCCAAAAGAAAACATATC | PET | 59 and 60 | D30− and D30+ | 640 |
| 184 | TGCAAGATATTCCTTGGTAATTCAG | no | 59 and 60 | D30− and D30+ | 640 |
| 187 | CGCTTTGAAGTGGTACCAGAGCA | VIC | 63 and 64 | D32− and D32+ | 400 |
| 188 | AATGCATGCCTAATATTTTCAGGGA | no | 63 and 64 | D32− and D32+ | 400 |

Capillary electrophoresis and genotyping. An aliquot of 1 µL of the PCR was withdrawn and mixed with 12 µL HiDi™ formamide (Applied Biosystems) and 0.5 µL internal length standard SST550-O (Biotype AG) which comprises a set of DNA fragment labelled with the fluorescent dye LIZ (proprietary of Applied Biosystems). Alternatively, the PCR was purified with the MiniElute® PCR purification kit (Qiagen GmbH, Hilden, Germany) and eluted in 25 µL TE-buffer prior mixing 1 µL of the eluate with HiDi™ formamide and SST550-O. The sample was denaturated for 3 min at 95° C., chilled to 10° C. and stored at room temperature prior electrophoresis. An ABI Prism 3130 Genetic Analyzer (Applied Biosystems) was used to separate PCR fragments by capillary electrophoresis. The samples were injected electrokinetically (15.000 V, 10 s). The electrophoretic run conditions were as follows: A capillary array with 4 capillaries (50 µm internal diameter, 35 cm length) filled with POP-4 [4% poly-(N,N-dimethylacrylamid), 8 M urea, 5% 2-pyrrolidone, 100 mM (hydroxymethyl)-methyl-3-aminopropan-sulfonic acid (TAPS)/NaOH pH 8.0, adjusted at room temperature; Applied Biosystems], at 60° C. and 15.000 Volt for 25 min. The filter set G5 was applied for the simultaneous detection of the 5 colours 6-FAM, VIC, NED, PET and LIZ. Fragment lengths and genotypes of the gene loci were calculated with the internal length standard and the Software Genmapper® (Applied Biosystems, Foster City, Calif., USA).

FIG. 1 shows the electropherogram of a genotyping experiment starting with 250 pg genomic DNA of a male person. The genotype of this DNA can be shortened as follows as a list of loci with the allele formula in parenthesis: D1 (+/+), D2 (+/+), D3 (−/−), D4 (−/+), D5 (−/−), D6 (+/+), D7 (−/−), D8 (−/+), D9 (−/+), D10 (−/+), D11 (−/+), D12 (−/+), D13 (−/+), D14 (+/+), D15 (−/+), D16 (−/+), D17 (−/−), D18 (−/−), D19 (−/+), D20 (−/+), D21 (−/−), D22 (−/+), D23 (−/+), D24 (−/+), D25 (−/+), D26 (−/+), D27 (−/+), D28 (−/−), D29 (−/+), D30 (−/+), D32 (−/+ or X/Y)

The invention claimed is:

1. A DNA profiling assay comprising the following steps,
(i) providing a sample to be analyzed,
(ii) providing reagents, enzyme and primer-oligonucleotides for simultaneous polymerase chain reaction amplification of at least 20 loci,
(iii) amplifying the loci,
(iv) detecting amplification products, Wherein the amplification products and the loci comprise the following features,
   (a) each locus comprises at least one deletion-insertion polymorphism, wherein two alleles from each locus differ in size by more than 1 nucleotide and less than 100 nucleotides,
   (b) a first set of at least two amplification products ranging in size from about 20 nucleotides to about 300 nucleotides stemming from at least two different loci carrying a first label,
   (c) a second set of at least two amplification products ranging in size from about 20 nucleotides to about 300 nucleotides stemming from at least two different loci carrying a second label,
   (d) a third set of at least two amplification products ranging in size from about 20 nucleotides to about 300 nucleotides stemming from at least two different loci carrying a third label,
   (e) wherein the first, second and third labels are each different fluorescent labels, and wherein
   (f) the size difference between two alleles for a given locus is larger than 1 nucleotide and smaller than 100 nucleotides,
wherein the loci are selected from the following group of sequences;
DIP NO 1:
   SEQ ID NO. 1 wherein the deletion-insertion polymorphism is between nucleotide No, 251 and No. 252,
   SEQ ID NO. 2 wherein the deletion-insertion polymorphism is between nucleotide No. 251 and No. 256,
DIP NO. 2:
   SEQ ID NO. 3 wherein the deletion-insertion polymorphism is between nucleotide No. 250 and No. 251,
   SEQ ID NO. 4 wherein the deletion-insertion polymorphism is between nucleotide No. 250 and NO. 255;
DIP NO. 3:
   SEQ ID NO. 5 wherein the deletion-insertion polymorphism is between nucleotide No. 251 and No. 252,
   SEQ ID NO. 6 wherein the deletion-insertion polymorphism is between nucleotide No, 251 and No. 256,
DIP NO. 4:
   SEQ ID. 7 wherein the deletion-insertion polymorphism is between nucleotide No. 250 and No. 251,
   SEQ ID NO. 8 wherein the deletion-insertion polymorphism is between nucleotide No. 250 and No. 262, DIP NO. 5:
SEQ ID NO. 9 wherein the deletion-insertion polymorphism is between nucleotide No, 251 and No. 252,
SEQ ID NO. 10 wherein the deletion-insertion polymorphism is between nucleotide No. 251 and No. 256,
DIP NO. 6:
SEQ ID NO. 11 wherein the deletion-insertion polymorphism is between nucleotide No. 251 and No. 252,
SEQ ID NO. 12 wherein the deletion-insertion polymorphism is between nucleotide No. 251 and No. 256,
DIP NO. 7;
SEQ ID NO. 13 wherein the deletion-insertion polymorphism is between nucleotide No. 251 and No. 252,
SEQ ID NO. 14 wherein the deletion-insertion polymorphism is between nucleotide No. 251 and No. 256,
DIP NO. 8:
SEQ ID NO. 15 wherein the deletion-insertion polymorphism is between nucleotide No.251 and No. 252,
SEQ ID NO. 16 wherein the deletion-insertion polymorphism is between nucleotide No. 251 and No. 256,
DIP NO. 9:
SEQ ID NO. 17 wherein the deletion-insertion polymorphism is between nucleotide No. 251 and No. 252,
SEQ ID NO. 18 wherein the deletion-insertion polymorphism is between nucleotide No. 251 and No. 257,
DIP NO. 10:
SEQ ID NO. 19 wherein the deletion-insertion polymorphism is between nucleotide No. 246 and No. 247,
SEQ ID NO. 20 wherein the deletion-insertion polymorphism is between nucleotide No. 246 and No. 252,
DIP NO. 11:
SEQ ID NO. 21 wherein the deletion-insertion polymorphism is between nucleotide No. 251 and No. 252,
SEQ ID NO. 22 wherein the deletion-insertion polymorphism is between nucleotide No. 251 and No. 256
DIP NO. 12:
SEQ ID NO. 23 wherein the deletion-insertion polymorphism is between nucleotide No. 250 and No. 251,
SEQ ID NO. 24 wherein the deletion-insertion polymorphism is between nucleotide No. 250 and No. 260,
DIP NO. 13:
SEQ ID NO. 25 wherein the deletion-insertion polymorphism is between nucleotide No. 251 and No. 252,
SEQ ID NO. 26 wherein the deletion-insertion polymorphism is between nucleotide No. 251 and No. 256,
DIP NO. 14:
SEQ ID NO. 27 wherein the deletion-insertion polymorphism is between nucleotide No. 251 and No. 252,
SEQ ID NO. 28 wherein the deletion-insertion polymorphism is between nucleotide No. 251 and No. 260,
DIP NO. 15:
SEQ ID NO. 29 wherein the deletion-insertion polymorphism is between nucleotide No. 251 and No. 252,
SEQ ID NO. 30 wherein the deletion-insertion polymorphism is between nucleotide No. 251 and No. 263,
DIP NO. 16:
SEQ ID NO. 31 wherein the deletion-insertion polymorphism is between nucleotide No. 251 and No. 252,
SEQ ID NO. 32 wherein the deletion-insertion polymorphism is between nucleotide No. 251 and No. 256,
DIP NO: 17:
SEQ ID NO. 33 wherein the deletion-insertion polymorphism is between nucleotide No. 251 and No. 252,
SEQ ID NO. 34 wherein the deletion-insertion polymorphism is between nucleotide No. 251 and No. 270,
DIP NO. 18:
SEQ ID NO. 35 wherein the insertion-deletion polymorphism is between nucleotide No. 251 and No. 252,
SEQ ID NO. 36 wherein the insertion-deletion polymorphism is between nucleotide No. 251 and No. 263,
DIP NO. 19:
SEQ ID NO. 37 wherein the deletion-insertion polymorphism is between nucleotide No. 251 and No. 252,
SEQ ID NO. 38 wherein the deletion-insertion polymorphism is between nucleotide No. 251 and No. 257,
DIP NO. 20:
SEQ ID NO. 39 wherein the deletion-insertion polymorphism is between nucleotide No. 251 and No. 252,
SEQ ID NO. 40 wherein the deletion-insertion polymorphism is between nucleotide No. 251 and No. 257,
DIP NO. 21:
SEQ ID NO. 41 wherein the deletion-insertion polymorphism is between nucleotide No. 251 and No. 252,
SEQ ID NO. 42 wherein the deletion-insertion polymorphism is between nucleotide No. 251 and No. 258,
DIP NO. 22:
SEQ ID NO. 43 wherein the deletion-insertion polymorphism is between nucleotide No. 250 and No. 251,
SEQ ID NO. 44 wherein the deletion-insertion polymorphism is between nucleotide No. 250 and No. 257,
DIP NO. 23:
SEQ ID NO. 45 wherein the deletion-insertion polymorphism is between nucleotide No. 251 and No. 252,
SEQ ID NO. 46 wherein the deletion-insertion polymorphism is between nucleotide No. 251 and No. 257,
DIP NO. 24:
SEQ ID NO. 47 wherein the deletion-insertion polymorphism is between nucleotide No. 251 and No. 252,
SEQ ID NO. 48 wherein the deletion-insertion polymorphism is between nucleotide No. 251 and No. 263,
DIP NO. 25:
SEQ ID NO. 49 wherein the deletion-insertion polymorphism is between nucleotide No. 250 and No. 251,
SEQ ID NO. 50 wherein the deletion-insertion polymorphism is between nucleotide No. 250 and No. 296,
DIP NO. 26:
SEQ ID NO. 51 wherein the deletion-insertion polymorphism is between nucleotide No. 251 and No. 252,
SEQ ID NO. 52 wherein the deletion-insertion polymorphism is between nucleotide No. 251 and No. 266,
DIP NO 27:
SEQ ID NO. 53 wherein the deletion-insertion polymorphism is between nucleotide No. 250 and No. 251,
SEQ ID NO. 54 wherein the deletion-insertion polymorphism is between nucleotide No. 250 and No. 273,
DIP NO. 28:
SEQ ID NO. 55 wherein the deletion-insertion polymorphism is between nucleotide No. 251 and No. 252,
SEQ ID NO. 56 wherein the deletion-insertion polymorphism is between nucleotide No. 251 and No. 260,
DIP NO. 29:
SEQ ID NO. 57 wherein the deletion-insertion polymorphism is between nucleotide No. 251 and No. 252,
SEQ ID NO. 58 wherein the deletion-insertion polymorphism is between nucleotide No. 251 and No. 267,
DIP NO. 30:
SEQ ID NO. 59 wherein the deletion-insertion polymorphism is between nucleotide No. 251 and No. 252,
SEQ ID NO. 60 wherein the deletion-insertion polymorphism is between nucleotide No. 251 and No. 270, DIP NO. 31,
SEQ ID NO. 61 wherein the deletion-insertion polymorphism is between nucleotide No. 271 and No. 272,
SEQ ID NO. 62 wherein the deletion-insertion polymorphism is between nucleotide No. 271 and No. 278,
DIP NO. 32:
SEQ ID NO. 63 wherein the deletion-insertion polymorphism is between nucleotide No. 280 and No. 281,
SEQ ID NO. 64 wherein the deletion-insertion polymorphism is between nucleotide No. 280 and No. 284,
DIP NO. 33:
SEQ ID NO. 65 wherein the deletion-insertion polymorphism is between nucleotide No. 250 and No. 251,
SEQ ID NO. 66 wherein the deletion-insertion polymorphism is between nucleotide No. 250 and No. 256,
DIP NO. 34:
SEQ ID NO. 67 wherein the deletion-insertion polymorphism is between nucleotide No. 251 and No. 252,
SEQ ID NO. 68 wherein the deletion-insertion polymorphism is between nucleotide No. 251 and No. 256,
DIP NO. 35,
SEQ ID NO. 69 wherein the deletion-insertion polymorphism is between nucleotide No. 250 and No. 251,
SEQ ID NO. 70 wherein the deletion-insertion polymorphism is between nucleotide No. 250 and No. 255,
DIP NO. 36:
SEQ ID NO. 71 wherein the deletion-insertion polymorphism is between nucleotide No. 250 and No. 251,
SEQ ID NO. 72 wherein the deletion-insertion polymorphism is between nucleotide No. 250 and No. 258,
DIP NO. 37:
SEQ ID NO. 73 wherein the deletion-insertion polymorphism is between nucleotide No. 251 and No. 252,
SEQ ID NO. 74 wherein the deletion-insertion polymorphism is between nucleotide No. 251 and No. 256,
DIP NO. 38:
SEQ ID NO. 75 wherein the deletion-insertion polymorphism is between nucleotide No. 255 and No. 256,
SEQ ID NO. 76 wherein the deletion-insertion polymorphism is between nucleotide No. 255 and No. 261,
DIP NO. 39:
SEQ ID NO. 77 wherein the deletion-insertion polymorphism is between nucleotide No. 251 and No. 252,
SEQ ID NO. 78 wherein the deletion-insertion polymorphism is between nucleotide No. 251 and No. 256,
DIP NO. 40:
SEQ ID NO. 79 wherein the deletion-insertion polymorphism is between nucleotide No. 250 and No. 251,
SEQ ID NO. 80 wherein the deletion-insertion polymorphism is between nucleotide No. 250 and No. 259,
DIP NO. 41:
SEQ ID NO. 81 wherein the deletion-insertion polymorphism is between nucleotide No. 251 and No. 252,
SEQ ID NO. 82 wherein the deletion-insertion polymorphism is between nucleotide No. 251 and No. 254,
DIP NO. 42:
SEQ ID NO. 83 wherein the deletion-insertion polymorphism is between nucleotide No. 251 and No. 252,
SEQ ID NO. 84 wherein the deletion-insertion polymorphism is between nucleotide No. 251 and No. 254,
DIP NO. 43:
SEQ ID NO. 85 wherein the deletion-insertion polymorphism is between nucleotide No. 251 and No. 252,
SEQ ID NO. 86 wherein the deletion-insertion polymorphism is between nucleotide No. 251 and No. 255,
DIP NO. 44:
SEQ ID NO. 87 wherein the deletion-insertion polymorphism is between nucleotide No. 250 and No. 251,
SEQ ID NO. 88 wherein the deletion-insertion polymorphism is between nucleotide No. 250 and No. 254,
DIP NO. 45:
SEQ ID NO. 89 wherein the deletion-insertion polymorphism is between nucleotide No. 250 and No. 251,
SEQ ID NO. 90 wherein the deletion-insertion polymorphism is between nucleotide No. 250 and No. 254,
DIP NO. 46:
SEQ ID NO. 91 wherein the deletion-insertion polymorphism is between nucleotide No. 250 and No. 251,
SEQ ID NO. 92 wherein the deletion-insertion polymorphism is between nucleotide No. 250 and No. 254,
DIP NO. 47:
SEQ ID NO. 93 wherein the deletion-insertion polymorphism is between nucleotide No. 251 and No. 252,
SEQ ID NO. 94 wherein the deletion-insertion polymorphism is between nucleotide No. 251 and No. 256,
DIP NO. 48:
SEQ ID NO. 95 wherein the deletion-insertion polymorphism is between nucleotide No. 251 and No. 252,
SEQ ID NO. 96 wherein the deletion-insertion polymorphism is between nucleotide No. 251 and No. 256,
DIP NO. 49:
SEQ ID NO. 97 wherein the deletion-insertion polymorphism is between nucleotide No. 247 and No. 248,
SEQ ID NO. 98 wherein the deletion-insertion polymorphism is between nucleotide No. 247 and No. 252,
DIP NO. 50:
SEQ ID NO. 99 wherein the deletion-insertion polymorphism is between nucleotide No. 250 and No. 251,
SEQ ID NO. 100 wherein the deletion-insertion polymorphism is between nucleotide No. 250 and No. 256,
DIP NO. 51:
SEQ ID NO. 101 wherein the deletion-insertion polymorphism is between nucleotide No. 251 and No. 252,
SEQ ID NO. 102 wherein the deletion-insertion polymorphism is between nucleotide No. 251 and No. 257,
DIP NO. 52:
SEQ ID NO. 103 wherein the deletion-insertion polymorphism is between nucleotide No. 250 and No. 251,
SEQ ID NO. 104 wherein the deletion-insertion polymorphism is between nucleotide No. 250 and No. 256,
DIP NO. 53:
SEQ ID NO. 105 wherein the deletion-insertion polymorphism is between nucleotide No. 250 and No. 251,
SEQ ID NO. 106 wherein the deletion-insertion polymorphism is between nucleotide No. 250 and No. 256,
DIP NO. 54:
SEQ ID NO. 107 wherein the deletion-insertion polymorphism is between nucleotide No. 251 and No. 252,
SEQ ID NO. 108 wherein the deletion-insertion polymorphism is between nucleotide No. 251 and No. 258,
DIP NO. 55:
SEQ ID NO. 109 wherein the deletion-insertion polymorphism is between nucleotide No. 251 and No. 252, SEQ ID NO. 110 wherein the deletion-insertion polymorphism is between nucleotide No. 251 and No. 258, DIP NO. 56:
SEQ ID NO. 111 wherein the deletion-insertion polymorphism is between nucleotide No. 250 and No. 251,
SEQ ID NO. 112 wherein the deletion-insertion polymorphism is between nucleotide No. 250 and No. 258, DIP NO. 57:
SEQ ID NO. 113 wherein the deletion-insertion polymorphism is between nucleotide No. 246 and No. 247,
SEQ ID NO. 114 wherein the deletion-insertion polymorphism is between nucleotide No. 246 and No. 252, DIP NO. 58:
SEQ ID NO. 115 wherein the deletion-insertion polymorphism is between nucleotide No. 250 and No. 251,
SEQ ID NO. 116 wherein the deletion-insertion polymorphism is between nucleotide No. 250 and No. 263, DIP NO. 59:
SEQ ID NO. 117 wherein the deletion-insertion polymorphism is between nucleotide No. 250 and No. 251,
SEQ ID NO. 118 wherein the deletion-insertion polymorphism is between nucleotide No. 250 and No. 266, DIP NO. 60:
SEQ ID NO. 119 wherein the deletion-insertion polymorphism is between nucleotide No. 251 and No. 252,
SEQ ID NO. 120 wherein the deletion-insertion polymorphism is between nucleotide No. 251 and No. 268, DIP NO. 61:
SEQ ID NO. 121 wherein the deletion-insertion polymorphism is between nucleotide No. 250 and No. 251,
SEQ ID NO. 122 wherein the deletion-insertion polymorphism is between nucleotide No. 250 and No. 277, DIP NO. 62:
SEQ ID NO. 123 wherein the deletion-insertion polymorphism is between nucleotide No. 251 and No. 252,
SEQ ID NO. 124 wherein the deletion-insertion polymorphism is between nucleotide No. 251 and No. 260, and DIP NO. 63:
SEQ ID NO. 289 wherein the deletion-insertion polymorphism is between nucleotide No. 250 and No. 251,
SEQ ID NO. 290 wherein the deletion-insertion polymorphism is between nucleotide No. 250 and No. 256, and wherein the primer pairs are each specific for a different DIP sequence.

2. The profiling assay according to claim 1, wherein at least 25 loci are amplified simultaneously.

3. The profiling assay according to claim 1, wherein at least 30 loci are amplified simultaneously.

4. The profiling assay according to claim 3, wherein each of the three sets b) to d) of amplification products comprises at least ten amplification products.

5. The profiling assay according to claim 1, wherein the two alleles from each locus differ in size by more than 1 nucleotide and less than 40 nucleotides.

6. The profiling assay of claim 1 wherein two or more of the amplification products ranging in size from about 20 nucleotides to about 300 nucleotides stemming from at least two different loci carry a fourth label.

7. The profiling assay of claim 1, wherein the detection step is carried out with a capillary gel electrophoresis device.

8. The profiling assay of claim 1, wherein additionally one or more short tandem repeat sequences (STR) are amplified and/or one or more variable number tandem repeat sequences (VNTR) are amplified and/or one or more single nucleotide polymorphisms (SNP) are amplified.

9. The profiling assay of claim 1, wherein additionally one or more sex specific short tandem repeat sequences (STR) and/or sex specific non variant DNA segments are amplified and/or one or more sex specific, variable number tandem repeat sequences (VNTR) are amplified and/or one or more sex specific single nucleotide polymorphisms (SNP) are amplified.

10. The profiling assay of claim 1, wherein the primer-oligonucleondes are primer-oligonucleotide pairs are selected from the group of nucleic acid molecules with the following sequences:
(a) DIP NO. 1: SEQ ID NO. 125 and SEQ ID NO. 126 or SEQ ID NO. 267 and SEQ ID NO. 268
(b) DIP NO. 2: SEQ ID NO. 127 and SEQ ID NO. 128
(c) DIP NO. 3: SEQ ID NO. 129 and SEQ ID NO. 130
(d) DIP NO. 4: SEQ ID NO. 131 and SEQ ID NO. 132
(e) DIP NO. 5: SEQ ID NO. 133 and SEQ ID NO. 134
(f) DIP NO. 6: SEQ ID NO. 135 and SEQ ID NO. 136
(g) DIP NO. 7: SEQ ID NO. 137 and SEQ ID NO. 138
(h) DIP NO. 8: SEQ ID NO. 139 and SEQ ID NO. 140 or SEQ ID NO. 287 and SEQ ID NO. 288
(i) DIP NO. 9: SEQ ID NO. 141 and SEQ ID NO. 142
(j) DIP NO. 10: SEQ ID NO. 143 and SEQ ID NO. 144
(k) DIP NO. 11: SEQ ID NO. 145 and SEQ ID NO. 146
(l) DIP NO. 12: SEQ ID NO. 147 and SEQ ID NO. 148
(m) DIP NO. 13: SEQ ID NO. 149 and SEQ ID NO. 150
(n) DIP NO. 14: SEQ ID NO. 151 and SEQ ID NO. 152
(o) DIP NO. 15: SEQ ID NO. 153 and SEQ ID NO. 154 or SEQ ID NO. 281 and SEQ ID NO. 282
(p) DIP NO. 16: SEQ ID NO. 155 and SEQ ID NO. 156
(q) DIP NO. 17: SEQ ID NO. 157 and SEQ ID NO. 158 or SEQ ID NO. 273 and SEQ ID NO. 274
(r) DIP NO. 18: SEQ ID NO. 159 and SEQ ID NO. 160 or SEQ ID NO. 277 and SEQ ID NO. 278
(s) DIP NO. 19: SEQ ID NO. 161 and SEQ ID NO. 162 or SEQ ID NO. 279 and SEQ ID NO. 280
(t) DIP NO. 20: SEQ ID NO. 163 and SEQ ID NO. 164 or SEQ ID NO. 275 and SEQ ID NO. 276
(u) DIP NO. 21: SEQ ID NO. 165 and SEQ ID NO. 166
(v) DIP NO. 22: SEQ ID NO. 167 and SEQ ID NO. 168
(w) DIP NO. 23: SEQ ID NO. 169 and SEQ ID NO. 170
(x) DIP NO. 24: SEQ ID NO. 171 and SEQ ID NO. 172
(y) DIP NO. 25: SEQ ID NO. 173 and SEQ ID NO. 174
(z) DIP NO. 26: SEQ ID NO. 175 and SEQ ID NO. 176
(aa) DIP NO. 27: SEQ ID NO. 177 and SEQ ID NO. 178
(ab) DIP NO. 28: SEQ ID NO. 179 and SEQ ID NO. 180
(ac) DIP NO. 29: SEQ ID NO. 181 and SEQ ID NO. 182 or SEQ ID NO. 271 and SEQ ID NO. 272
(ad) DIP NO. 30: SEQ ID NO. 183 and SEQ ID NO. 184 or SEQ ID NO. 283 and SEQ ID NO. 284

(ae) DIP NO. 31: SEQ ID NO. 185 and SEQ ID NO. 186
(af) DIP NO. 32: SEQ ID NO. 187 and SEQ ID NO. 188 or SEQ ID NO. 269 and SEQ ID NO. 270
(ag) DIP NO. 33: SEQ ID NO. 189 and SEQ ID NO. 190 or SEQ ID NO. 285 and SEQ ID NO. 286
(ah) DIP NO. 34: SEQ ID NO. 191 and SEQ ID NO. 191
(ai) DIP NO. 35: SEQ ID NO. 193 and SEQ ID NO. 194
(aj) DIP NO. 36: SEQ ID NO. 195 and SEQ ID NO. 196
(ak) DIP NO. 37: SEQ ID NO. 197 and SEQ ID NO. 198
(al) DIP NO. 38: SEQ ID NO. 199 and SEQ ID NO. 200
(am) DIP NO. 39: SEQ ID NO. 201 and SEQ ID NO. 202
(an) DIP NO. 40: SEQ ID NO. 203 and SEQ ID NO. 204
(ao) DIP NO. 41: SEQ ID NO. 205 and SEQ ID NO. 206 or SEQ ID NO. 251 and SEQ ID NO. 252
(ap) DIP NO. 42: SEQ ID NO. 207 and SEQ ID NO. 208 or SEQ ID NO. 253 and SEQ NO. 254
(aq) DIP NO. 43: SEQ ID NO. 209 and SEQ ID NO. 210 or SEQ ID NO. 255 and SEQ ID NO. 256
(ar) DIP NO. 44: SEQ ID NO. 211 and SEQ ID NO. 212 or SEQ ID NO. 257 and SEQ ID NO. 258
(as) DIP NO. 45: SEQ ID NO. 213 and SEQ ID NO. 214 SEQ ID NO. 259 and SEQ ID NO. 260
(at) DIP NO. 46: SEQ ID NO. 215 and SEQ ID NO. 216 or SEQ ID NO. 261 and SEQ ID NO. 262
(au) DIP NO. 47: SEQ ID NO. 217 and SEQ ID NO. 218 or SEQ ID NO. 263 and SEQ ID NO. 264
(av) DIP NO. 48: SEQ ID NO. 219 and SEQ ID NO. 220
(aw) DIP NO. 49: SEQ ID NO. 221 and SEQ ID NO. 222
(ax) DIP NO. 50: SEQ ID NO. 223 and SEQ ID NO. 224
(ay) DIP NO. 51: SEQ ID NO. 225 and SEQ ID NO. 226 or SEQ ID NO. 265 and SEQ ID NO. 266
(az) DIP NO. 52: SEQ ID NO. 227 and SEQ ID NO. 228
(ba) DIP NO. 53: SEQ ID NO. 229 and SEQ ID NO. 230
(bb) DIP NO. 54: SEQ ID NO. 231 and SEQ ID NO. 232
(bc) DIP NO. 55: SEQ ID NO. 233 and SEQ ID NO. 234
(bd) DIP NO. 56: SEQ ID NO. 235 and SEQ ID NO. 236
(be) DIP NO. 57: SEQ ID NO. 237 and SEQ ID NO. 238
(bf) DIP NO. 58: SEQ ID NO. 239 and SEQ ID NO. 240
(bg) DIP NO. 59: SEQ ID NO. 241 and SEQ ID NO. 242
(bh) DIP NO. 60: SEQ H) NO. 243 and SEQ ID NO. 244
(bi) DIP NO. 61: SEQ ID NO. 245 and SEQ ID NO. 246
(bj) DIP NO. 62: SEQ ID NO. 247 and SEQ ID NO. 248 and
(bk) DIP NO. 63: SEQ ID NO. 249 and SEQ ID NO. 250.

\* \* \* \* \*